US012377286B2

(12) United States Patent
Miskin et al.

(10) Patent No.: US 12,377,286 B2
(45) Date of Patent: Aug. 5, 2025

(54) ANTI-INFECTIVE AND THERAPEUTIC ELECTROMAGNETIC EMISSION METHODS AND DEVICES

(71) Applicant: SunInLyf Bio Inc., Sleepy Hollow, IL (US)

(72) Inventors: Mike Miskin, Sleepy Hollow, IL (US); Robert Kottritsch, Wixams (GB); Charles F. Huber, Lake Forrest, IL (US); Allan Brent York, Langley (CA)

(73) Assignee: SuninLyf Bio Inc., Sleepy Hollow, IL (US)

( * ) Notice: Subject to any disclaimer, the term of this patent is extended or adjusted under 35 U.S.C. 154(b) by 0 days.

(21) Appl. No.: 18/424,513

(22) Filed: Jan. 26, 2024

(65) Prior Publication Data

US 2024/0261591 A1    Aug. 8, 2024
US 2025/0082962 A9    Mar. 13, 2025

Related U.S. Application Data

(60) Provisional application No. 63/630,055, filed on Dec. 26, 2023, provisional application No. 63/457,039, (Continued)

(51) Int. Cl.
*A61N 5/06* (2006.01)
*A61N 5/067* (2006.01)
*G06F 3/01* (2006.01)

(52) U.S. Cl.
CPC ........... *A61N 5/0624* (2013.01); *A61N 5/067* (2021.08); *G06F 3/013* (2013.01); *A61N 2005/0626* (2013.01); *A61N 2005/0648* (2013.01); *A61N 2005/0651* (2013.01); *A61N 2005/0659* (2013.01); *A61N 2005/0663* (2013.01)

(58) Field of Classification Search
CPC ..... A61N 5/06–2005/073; G06F 3/013; A61B 18/20–18/28
See application file for complete search history.

(56) References Cited

U.S. PATENT DOCUMENTS 4,595,491 A    6/1986 Berns
5,259,380 A    11/1993 Mendes et al.
(Continued)

FOREIGN PATENT DOCUMENTS

AU    2021374233    6/2023
CN    109417841    3/2019
(Continued)

OTHER PUBLICATIONS

European Office Action—Application No. 21792152.7 dated Mar. 22, 2024—9 pages.

*Primary Examiner* — Jonathan T Kuo
(74) *Attorney, Agent, or Firm* — K&L Gates LLP

(57) ABSTRACT

A light emitting device for video displays with anti-infective and therapeutic electromagnetic emission methods and devices is disclosed. The light emitting device for video displays with anti-infective and therapeutic electromagnetic emission methods and devices uses non-visible and/or visible electromagnetic radiation on living species, including but not limited to people and animals, to provide treatments against infections and/or provide photobiomodulation treatments to improve health and wellness.

30 Claims, 45 Drawing Sheets

Related U.S. Application Data filed on Apr. 4, 2023, provisional application No. 63/489,139, filed on Mar. 8, 2023, provisional application No. 63/481,742, filed on Jan. 26, 2023.

(56) References Cited

U.S. PATENT DOCUMENTS

| | | | |
|---|---|---|---|
| 5,445,146 | A | 8/1995 | Bellinger |
| 5,500,009 | A | 3/1996 | Mendes et al. |
| 5,766,233 | A | 6/1998 | Rolf |
| 5,913,883 | A | 6/1999 | Alexander et al. |
| 6,019,482 | A | 2/2000 | Randall |
| 6,269,818 | B1 | 8/2001 | Harvey et al. |
| 6,350,275 | B1 | 2/2002 | Vreman et al. |
| 6,488,698 | B1 | 12/2002 | Hyman |
| 6,673,095 | B2 | 1/2004 | Nordquist |
| 6,875,225 | B1 | 4/2005 | Pederson |
| 7,348,736 | B2 | 3/2008 | Piepgras et al. |
| 7,517,344 | B2 | 4/2009 | Vam Hal et al. |
| 7,559,945 | B2 | 7/2009 | Breden et al. |
| 7,648,649 | B2 | 1/2010 | Radkov |
| 7,686,839 | B2 | 3/2010 | Parker |
| 8,506,612 | B2 | 8/2013 | Ashdown |
| 9,079,022 | B2 | 7/2015 | Baird et al. |
| 9,289,622 | B2 | 3/2016 | Feng et al. |
| 9,410,664 | B2 | 8/2016 | Krames |
| 9,415,237 | B2 | 8/2016 | Giovanna et al. |
| 9,440,090 | B2 | 9/2016 | Jo et al. |
| 9,526,860 | B2 | 12/2016 | Baaijens et al. |
| 9,579,521 | B2 | 2/2017 | Ferraz Rigo et al. |
| 9,844,116 | B2 | 3/2017 | Soler et al. |
| 9,662,067 | B2 | 5/2017 | Gimenez et al. |
| 9,719,660 | B1 | 8/2017 | Petluri et al. |
| 9,808,644 | B2 | 11/2017 | Daffer |
| 9,867,255 | B2 | 1/2018 | Wouter et al. |
| 9,927,097 | B2 | 3/2018 | Lalicki et al. |
| 10,009,974 | B2 | 6/2018 | Bremser et al. |
| 10,322,297 | B1 | 6/2019 | Hinds et al. |
| 10,357,582 | B1 | 7/2019 | Barron et al. |
| 10,471,231 | B2 | 11/2019 | Moore-Ede et al. |
| 10,492,264 | B2 | 11/2019 | Petluri et al. |
| 10,632,214 | B2 | 4/2020 | David et al. |
| 10,660,182 | B2 * | 5/2020 | Tsubota ............... H05B 47/105 |
| 10,750,591 | B2 | 8/2020 | Petluri et al. |
| 10,900,615 | B2 | 1/2021 | Krames et al. |
| 11,168,250 | B2 | 1/2021 | Petluri et al. |
| 11,198,813 | B2 | 2/2021 | Raghuram et al. |
| 11,073,727 | B2 | 7/2021 | David |
| 11,102,863 | B2 | 8/2021 | Raghuram et al. |
| 11,191,140 | B2 | 11/2021 | Petluri et al. |
| 11,198,020 | B2 | 12/2021 | Petluri et al. |
| 11,265,983 | B2 | 3/2022 | Raghuram et al. |
| 11,287,692 | B1 | 3/2022 | Pickard et al. |
| 11,308,849 | B2 | 4/2022 | Petluri et al. |
| 11,338,107 | B2 | 5/2022 | Allen et al. |
| 11,371,660 | B2 | 6/2022 | Raghuram et al. |
| 11,511,071 | B2 | 11/2022 | Krames et al. |
| 11,552,278 | B2 | 1/2023 | Hack et al. |
| 11,783,748 | B2 | 10/2023 | Petluri et al. |
| 2002/0015013 | A1 | 2/2002 | Ragle |
| 2003/0009158 | A1 | 1/2003 | Perricone |
| 2003/0189829 | A1 | 10/2003 | Shimizu et al. |
| 2004/0011132 | A1 | 1/2004 | Netzel |
| 2004/0030370 | A1 | 2/2004 | Lytle |
| 2004/0147984 | A1 | 7/2004 | Altshuler et al. |
| 2004/0162549 | A1 | 8/2004 | Altshuler |
| 2004/0210277 | A1 | 10/2004 | Becker et al. |
| 2004/0225339 | A1 | 11/2004 | Yaroslavsky et al. |
| 2004/0230259 | A1 | 11/2004 | De Matteo |
| 2005/0128751 | A1 | 6/2005 | Roberge et al. |
| 2005/0177139 | A1 | 8/2005 | Yamazaki et al. |
| 2005/0222555 | A1 | 10/2005 | Manstein et al. |
| 2006/0009822 | A1 | 1/2006 | Savage et al. |
| 2006/0030908 | A1 | 2/2006 | Powell et al. |
| 2006/0200212 | A1 | 9/2006 | Brawn |
| 2006/0217586 | A1 | 9/2006 | Van Hal et al. |
| 2007/0027510 | A1 | 2/2007 | Rodrigues et al. |
| 2007/0086912 | A1 | 4/2007 | Dowling et al. |
| 2007/0115658 | A1 | 5/2007 | Mueller et al. |
| 2007/0219605 | A1 | 9/2007 | Yaroslavsky et al. |
| 2008/0275533 | A1 | 11/2008 | Powell |
| 2009/0054953 | A1 | 2/2009 | Whitehurst |
| 2009/0204185 | A1 | 8/2009 | De Kok et al. |
| 2009/0281604 | A1 | 11/2009 | Do Boer et al. |
| 2009/0326616 | A1 | 12/2009 | Aarts et al. |
| 2010/0105022 | A1 | 4/2010 | Kuiper et al. |
| 2010/0171441 | A1 | 7/2010 | Schlangen et al. |
| 2010/0174345 | A1 | 7/2010 | Ashdown |
| 2012/0088204 | A1 | 4/2012 | Ho et al. |
| 2012/0095534 | A1 | 4/2012 | Schlangen et al. |
| 2012/0253432 | A1 | 10/2012 | Loveland |
| 2013/0147400 | A1 | 1/2013 | Van Herpen et al. |
| 2013/0131762 | A1 | 5/2013 | Oversluizen et al. |
| 2013/0190845 | A1 | 7/2013 | Liu et al. |
| 2013/0218240 | A1 | 8/2013 | Feng et al. |
| 2013/0238060 | A1 | 9/2013 | Nevins |
| 2014/0128941 | A1 | 5/2014 | Williams |
| 2014/0265926 | A1 | 9/2014 | Hu et al. |
| 2015/0039060 | A1 | 2/2015 | Paulussen et al. |
| 2015/0039061 | A1 | 2/2015 | Hong et al. |
| 2015/0051672 | A1 | 2/2015 | Jo et al. |
| 2015/0231408 | A1 | 8/2015 | Williams et al. |
| 2015/0238120 | A1 | 8/2015 | Shan et al. |
| 2015/0283399 | A1 | 10/2015 | Guglielmi et al. |
| 2015/0343235 | A1 | 12/2015 | Blanche et al. |
| 2016/0076736 | A1 | 3/2016 | Van Bommel et al. |
| 2016/0116124 | A1 | 4/2016 | Podowitz et al. |
| 2016/0317833 | A1 | 11/2016 | Tedford et al. |
| 2017/0231058 | A1 | 8/2017 | Sadwick |
| 2017/0361124 | A1 | 12/2017 | Parker et al. |
| 2018/0077767 | A1 | 3/2018 | Soler et al. |
| 2018/0092521 | A1 | 4/2018 | Nolan et al. |
| 2018/0154172 | A1 | 6/2018 | Kalmeta |
| 2018/0160491 | A1 | 6/2018 | Biery et al. |
| 2018/0296851 | A1 * | 10/2018 | Carlin ................. A61M 16/00 |
| 2018/0318599 | A1 | 11/2018 | Van Bommel et al. |
| 2019/0167400 | A1 | 6/2019 | Barnes et al. |
| 2019/0280717 | A1 | 9/2019 | Jeong et al. |
| 2019/0348628 | A1 | 11/2019 | Hack et al. |
| 2020/0092971 | A1 * | 3/2020 | Tsubota ............... A61N 5/0613 |
| 2020/0146120 | A1 | 5/2020 | Petluri et al. |
| 2020/0260546 | A1 | 8/2020 | Petluri et al. |
| 2020/0298016 | A1 | 9/2020 | Yoon et al. |
| 2021/0060353 | A1 | 3/2021 | Raghuram et al. |
| 2021/0125907 | A1 | 4/2021 | Huang et al. |
| 2021/0136887 | A1 | 5/2021 | Raghuram et al. |
| 2021/0227657 | A1 | 7/2021 | Petluri et al. |
| 2021/0242182 | A1 | 8/2021 | Yamakawa et al. |
| 2021/0251060 | A1 | 8/2021 | Petluri et al. |
| 2021/0290973 | A1 | 9/2021 | Moore-Ede et al. |
| 2021/0315083 | A1 | 10/2021 | Harrison et al. |
| 2021/0338861 | A1 | 11/2021 | Harrison et al. |
| 2021/0402210 | A1 | 12/2021 | Raghuram et al. |
| 2022/0001200 | A1 | 1/2022 | Petluri et al. |
| 2022/0005404 | A1 | 1/2022 | Raghuram et al. |
| 2022/0036793 | A1 | 2/2022 | Raghuram et al. |
| 2022/0180803 | A1 | 6/2022 | Raghuram et al. |
| 2022/0264717 | A1 | 8/2022 | Parker et al. |
| 2022/0272806 | A1 | 8/2022 | Petluri et al. |
| 2022/0272820 | A1 | 8/2022 | Raghuram et al. |
| 2022/0288412 | A1 | 9/2022 | Honold et al. |
| 2022/0323785 | A1 * | 10/2022 | Petluri ................. G09G 3/342 |
| 2022/0334305 | A1 | 10/2022 | Harrison et al. |
| 2022/0404667 | A1 | 12/2022 | Pickard et al. |
| 2023/0285771 | A1 | 9/2023 | Petluri et al. |
| 2023/0324035 | A1 | 10/2023 | Maa et al. |

FOREIGN PATENT DOCUMENTS

| | | |
|---|---|---|
| DE | 202018005328 | 1/2019 |
| DK | 2874701 | 6/2018 |
| EP | 3504942 | 1/1990 |
| EP | 2094064 | 8/2009 |
| EP | 2164568 | 3/2010 |
| EP | 2348246 | 7/2011 |

(56) References Cited

FOREIGN PATENT DOCUMENTS

| | | |
|---|---|---|
| EP | 2905544 | 8/2015 |
| EP | 3427660 | 1/2019 |
| EP | 3668276 | 6/2020 |
| EP | 4067729 | 10/2022 |
| EP | 4190367 | 6/2023 |
| JP | 5937016 | 5/2013 |
| JP | 2020505787 | 2/2020 |
| KR | 20070043085 | 4/2007 |
| KR | 20070045382 | 5/2007 |
| KR | 100973078 | 7/2010 |
| KR | 20110081213 | 7/2011 |
| KR | 20120050781 | 5/2012 |
| KR | 102571122 | 8/2023 |
| KR | 102571168 | 8/2023 |
| KR | 102571173 | 8/2023 |
| KR | 102571180 | 8/2023 |
| KR | 102571189 | 8/2023 |
| KR | 102571194 | 8/2023 |
| KR | 102571272 | 8/2023 |
| KR | 102571273 | 8/2023 |
| KR | 102571274 | 8/2023 |
| KR | 102571275 | 8/2023 |
| KR | 102571277 | 8/2023 |
| KR | 102592001 | 10/2023 |
| KR | 102592005 | 10/2023 |
| SU | 155992 | 10/1985 |
| WO | 9000458 | 1/1990 |
| WO | 2008069101 | 3/2010 |
| WO | 2012021243 | 2/2012 |
| WO | 2015184019 | 12/2015 |
| WO | 2016037994 | 3/2016 |
| WO | 2016146688 | 9/2016 |
| WO | 2017210461 | 12/2017 |
| WO | 2016208683 | 4/2018 |
| WO | 2018130403 | 7/2018 |
| WO | 2019139635 | 7/2019 |
| WO | 2019140306 | 7/2019 |
| WO | 2020097575 | 5/2020 |
| WO | 2022200131 | 9/2022 |

* cited by examiner

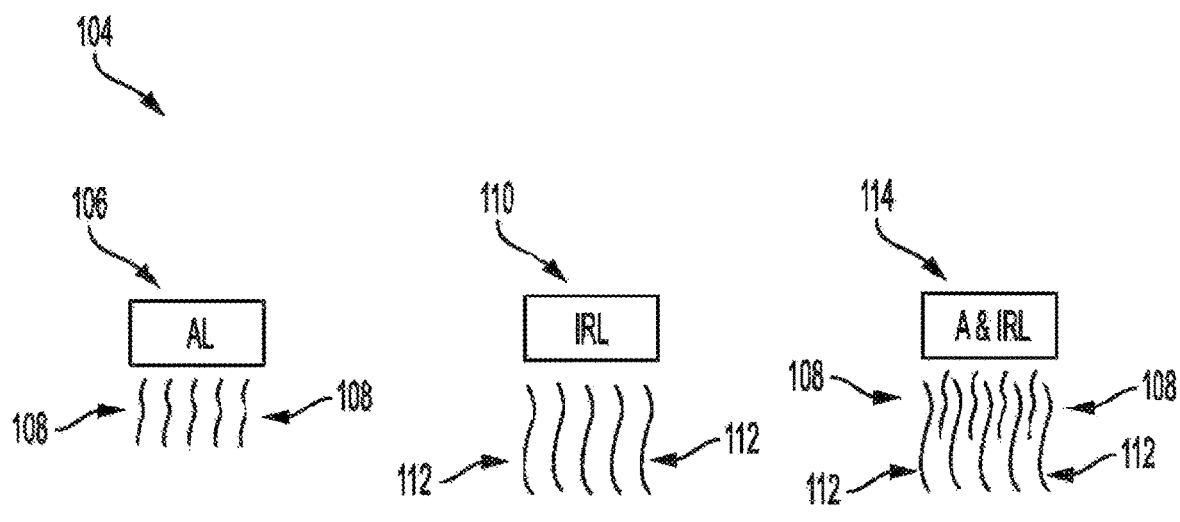

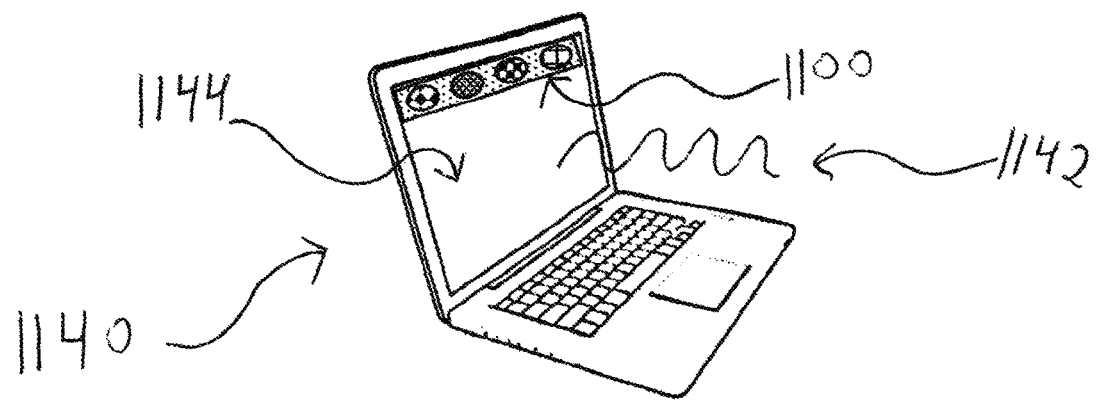
19A
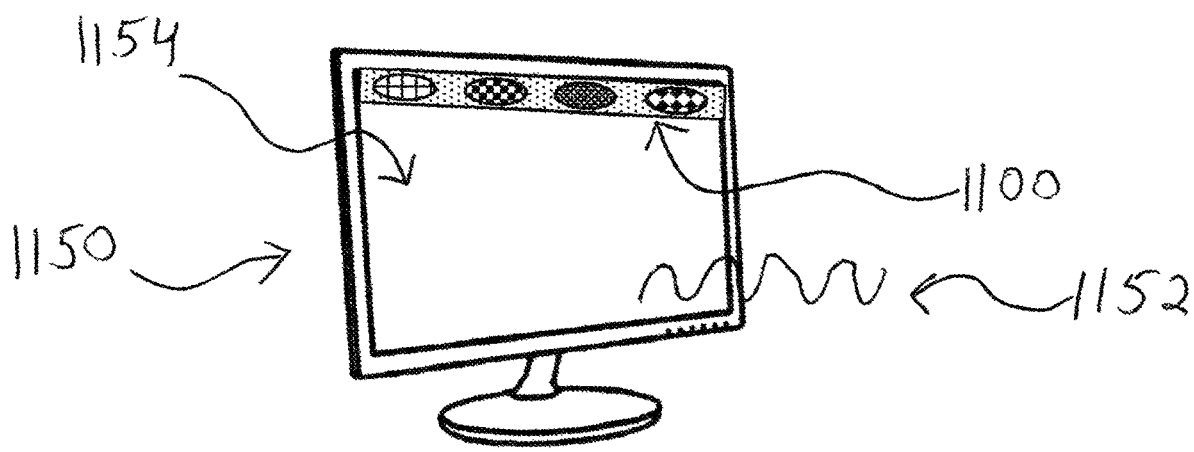
19B

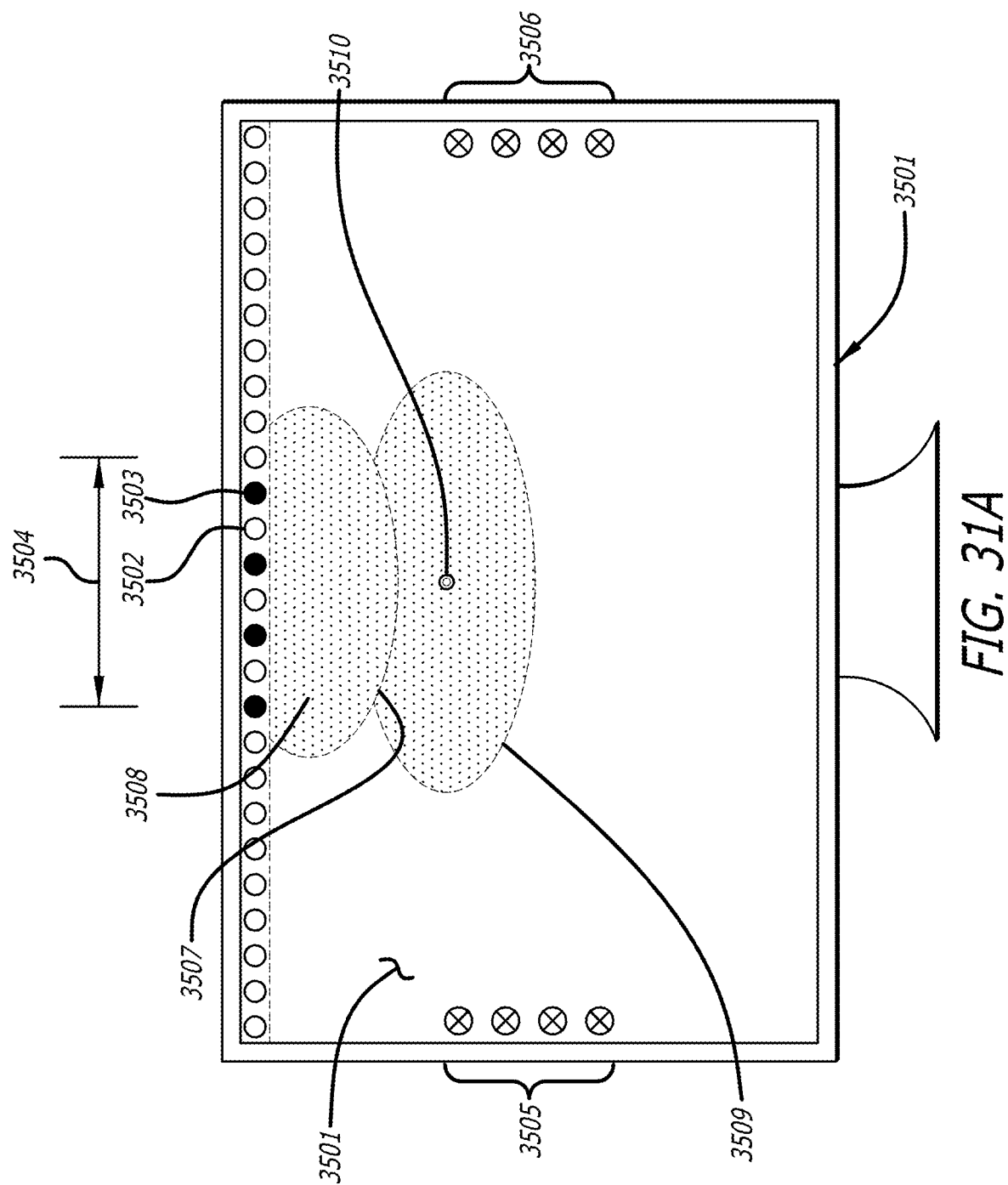

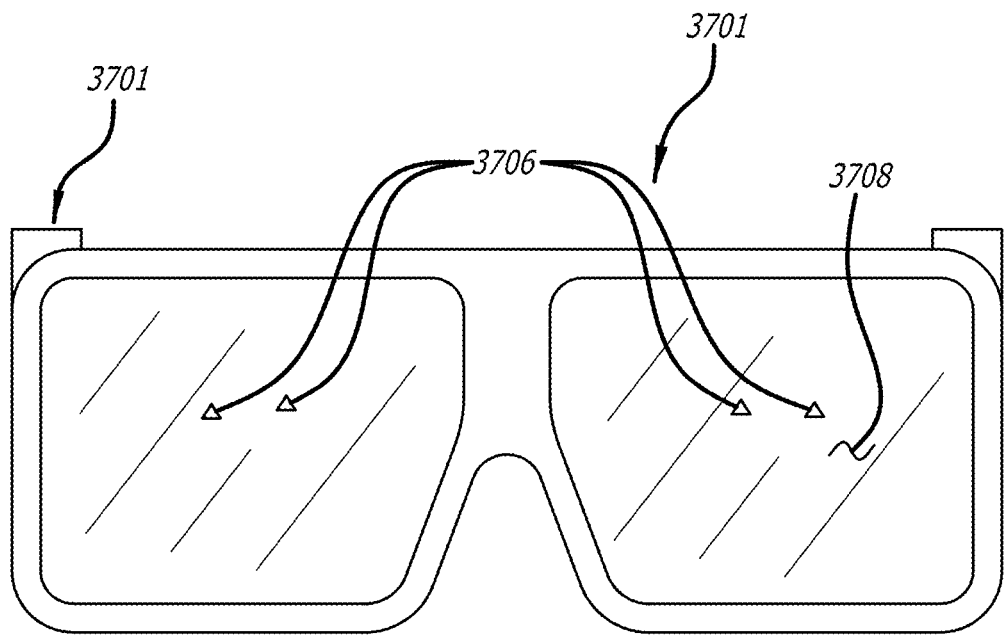
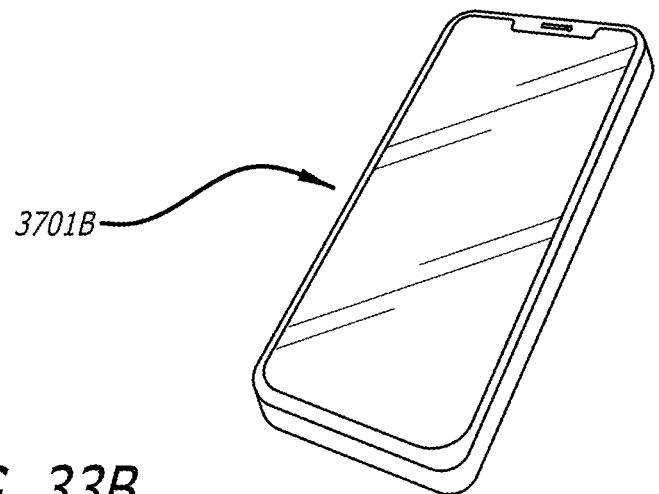
FIG. 33B

ANTI-INFECTIVE AND THERAPEUTIC ELECTROMAGNETIC EMISSION METHODS AND DEVICES

PRIORITY CLAIM

The present application claims priority to and the benefit of U.S. Provisional Patent Application No. 63/481,742, filed on Jan. 26, 2023, U.S. Provisional Patent Application No. 63/489,139, filed on Mar. 8, 2023, and U.S. Provisional Patent Application No. 63/457,039, filed on Apr. 4, 2023, the entirety of which are incorporated herein by reference and relied upon.

TECHNICAL FIELD

The present invention generally relates to anti-infective light radiation and/or therapeutic electromagnetic emission methods and devices. More specifically, the present invention relates to devices configured to emit visible and/or non-visible electromagnetic radiation and/or emissions "light radiation" of at least one or a combination of two or more wavelengths of red, green, and blue ("RGB"), blue, ultraviolet ("UV"), near-UV, orange, cyan, red, and/or infrared light wavelengths that are directed towards and/or concentrated towards or inside of a specific portion or body part of a person and/or other living species. The therapeutic electromagnetic emission methods and devices are configured to deliver one or a combination of beneficial results including but not limited to reducing or killing an infection, providing photobiomodulation treatments, delivering and/or providing heat, accelerating healing, disinfecting, and other treatments near on or within living species including but not limited to humans, animals, mammals and other living species and/or organisms.

BACKGROUND

Electromagnetic radiation including in the microwave spectrum has been used to treat cancer and is known to be dangerous. In addition to treating cancer, radiation oncologists may use ionizing radiation to treat benign tumours that are unresectable (unable to be removed by surgery), such as certain types of tumours occurring in the brain (e.g., craniopharyngiomas and acoustic neuromas). Until the significant long-term consequences of ionizing radiation were recognized, radiation therapy was sometimes used for conditions such as acne, tinea capitis (ringworm of the scalp and nails), and lymph node enlargement. However, those uses were abandoned following the discovery of ionizing radiation injury. Early radiation therapy machines produced X-rays that were in the orthovoltage range (between about 140 and 400 kilovolts). That treatment caused serious and often intolerable skin burns. Modern radiation therapy machines produce beams that are in the high-energy megavoltage range (more than 1,000 kilovolts), which allows the beam to penetrate tissues and treat deep-seated tumours. The dosage to the skin, however, is lower than with orthovoltage treatment.

The majority of modern radiation therapy treatments are external beam teletherapy, or long-distance therapy (sometimes also called external beam radiotherapy). External beam machines produce ionizing radiation either by radioactive decay of a nuclide, most commonly cobalt-60, or through the acceleration of electrons or other charged particles, such as protons. Most radiation therapy treatments use irradiation generated by linear accelerators, which impart a series of relatively small increases in energy to particles such as protons, carbon ions, or neutrons. The accelerated particles bombard a target, which then produces the therapeutic beam of radiation. The energy of the beam is determined by the energy of the accelerated particles. Two commonly used approaches to external beam teletherapy are intensity-modulated radiation therapy ("IMRT") and particle beam therapy.

Another technique used for the delivery of radiation is known as brachytherapy. In that form of therapy, radiation is implanted directly into a tumour or tumour-bearing tissue. The encapsulated radioactive sources are inserted into the tumour via catheters or needles. A catheter can be placed into a tumour bed after tumour resection, whereas a needle can be inserted into the affected tissue directly or into the body cavity housing the affected tissue. In both cases, radioactive sources are carefully threaded into the delivery device. Brachytherapy is valuable in particular because it can deliver a high dose of radiation to the tumour tissue or tumour bed while sparing the surrounding healthy tissue.

It has been known for several decades that the use of light can give a positive therapeutic effect in the treatment of a wide spectrum of diseases. In the 1960's the use of narrow wavelength light was investigated in vivo/in vitro experiments. It was found that light of wavelength greater than 440 nm did not work. Further investigations were carried out with light having a wavelength of from 300 to 350 nm (UV light) but it was found that infection was exacerbated/promoted rather than ameliorated/eliminated. Some attempts have been made to treat individuals affected with the herpes virus by treatment with light of the wavelength 660 nm, as described in U.S. Pat. No. 5,500,009.

Additionally, it is known from the prior art to use a laser to produce coherent radiation and to focus it on the area to be treated. Nd YAG laser treatment at a fundamental wavelength of 1064 nm is associated with decreased pain, scarring and improved healing (U.S. Pat. No. 5,445,146). Additionally, it has been reported that diodes emitting light at the red wavelength, 940±25 nm can be used to treat a range of essentially musculoskeletal ailments (U.S. Pat. No. 5,259,380). However, there is no indication that light of a wavelength above this would be of any therapeutic use.

It has now been surprisingly established that low intensity electromagnetic radiation of small bandwidth is effective in the treatment of infectious diseases, inflammatory-type diseases, and other conditions, including the alleviation of pain. It is postulated that the way in which the electromagnetic radiation affects its action is by way of energy transmission through cellular components/organelles.

A water molecule that has a range of electromagnetic radiation wavelengths passed through it will produce several transmission peaks. These transmission peaks can be associated with the preferred therapeutic electromagnetic radiation wavelengths and/or ranges used in the invention and thus implies there may be a role for the water molecule in the general mechanism of action.

Ultraviolet ("UV") light has been used to reduce and/or kill unwanted microorganisms and/or bacteria. UV radiation is electromagnetic radiation with a wavelength (100-400 nm) shorter than that of visible light (400-700 nm), but longer than x-rays (<100 nm). UV irradiation is divided into four distinct spectral areas including vacuum UV (100-200 nm), UVC (200-280 nm), UVB (280-315 nm), and UVA (315-400 nm). The mechanism of UVC inactivation of microorganisms is to damage the genetic material in the nucleus of the cell or nucleic acids in the virus. The UVC spectrum, especially the range of 250-270 nm, is strongly absorbed by the nucleic acids of a microorganism and, therefore, is the most lethal range of wavelengths for microorganisms. This range, with 262 nm being the peak germicidal wavelength, is known as the germicidal spectrum. The light-induced damage to the DNA and RNA of a microorganism often results from the dimerization of pyrimidine molecules. In particular, thymine (which is only found only in DNA) produces cyclobutane dimers. When thymine molecules are dimerized, it becomes very difficult for the nucleic acids to replicate and if replication does occur it often produces a defect that prevents the microorganism from being viable.

Although it has been known for the last 100 years that UVC irradiation is highly germicidal, the use of UVC irradiation for prevention and treatment of infections is still in the very early stages of development. Most of the studies are confined to in vitro and ex vivo levels, while in vivo animal studies and clinical studies are much rarer. Studies that have examined UVC inactivation of antibiotic-resistant bacteria have found them to be as equally susceptible as their naive counterparts. Within the UVC range, 254 nm is easily produced from a mercury low-pressure vapor lamp, or more recently light emitting diode "LED" technology and has been shown to be close to the 262 nm optimal wavelength for germicidal action. Because the delivery of any UV light, including UVC irradiation to living tissue is a localized process and introduces added risk of damaging and/or destroying good, healthy living cells similar to that of microwave, UVC for infectious diseases is likely to be applied exclusively to localized infections more often as a last resort solution.

Blue light wavelengths fall within the range of 380 nm to 500 nm. Blue light, particularly in the morning, has several benefits including but not limited to promoting alertness. Blue light stimulates parts of the brain that make us feel alert, elevating our body temperature and heart rate which can boost alertness and mental sharpness. Blue light can additionally boost memory and cognitive function, help elevate mood. Blue light can additionally regulate a person's natural sleep and wake cycle and/or circadian rhythm. In the morning blue light suppresses sleep inducing hormones which help a person wake up. However, it is recommended to manage exposure to blue light and too much blue light, especially late in the day can interfere with a person's sleep by blocking the hormone called melatonin which makes a person sleepy.

The infrared ("IR") radiation energy spectrum falls within the range of approximately 700 nm to 1 mm and is often broken into categories and referred to as one of either near infrared ("NIR"), mid-infrared ("MIR"), or far-infrared ("FIR") energy. One or more of these IR energies are often used in various types of light therapy including but not limited to dermatology, hair growth, and saunas.

NIR energy is cooler than MIR and FIR, so it may be much easier for some people to handle. It has a detoxing effect on the body and includes some of the additional following benefits: heals wounds by causing regeneration of mitochondria cells, especially in skin, muscles, and tendons; anti-aging due to regeneration of mitochondria cells and its antioxidant properties; improves oxygen delivery to cells; and improves overall health because it enables the body to perform metabolic processes better.

MIR energy reaches deeper into a body providing some other benefits including: better blood circulation; reduced pain and inflammation due to increased blood circulation and oxygen delivery; quicker recovery from injury; and weight loss.

FIR energy reaches the deepest and heats up a person's core. It includes the following benefits: detoxification due to producing sweat that comes from deep within removing the toxins; relaxation due to the heat penetrating deeply; and lower blood pressure because the heat allows arteries to dilate.

Adenosine triphosphate ("ATP") is an energy-carrying molecule known as "the energy currency of life" or "the fuel of life," because it's the universal energy source for all living cells. Every living organism consists of cells that rely on ATP for their energy needs. ATP is made by converting the food into energy. It's an essential building block for all life forms. Without ATP, cells wouldn't have the fuel or power to perform functions necessary to stay alive, and they would eventually die. All forms of life rely on ATP to do the things they must do to survive.

Red and/or IR light improve the efficiency of the cellular respiration process and help a body make and use ATP energy more effectively. Red and/or IR wavelengths of electromagnetic energy do this by stimulating and/or impacting mitochondria, the powerhouses of the cell. Red and/or IR light therapy can increase the number of mitochondria, and also boost their function in the cell and can be integrated into medical devices, general lighting devices, and devices with electronic video displays and in some cases and/or product applications may include UV and/or near UV light emitters to kill infectious diseases and/or unwanted bacteria with the UV and/or near UV as well as simultaneously stimulate mitochondria cells to regenerate and/or increase production of ATP.

LED lighting devices have been developed to emit near UV and/or visible light that also kill bacteria and is safer on living species cells but require more time to kill microorganisms than conventional UV light sources, as taught by Lalicki et al. in U.S. Pat. Nos. 9,927,097 and 10,357,582. These devices emit a majority of light/peak of light within the 380-420 nm wavelength range rather than wavelengths within the conventional range of visible light at approximately 450-495 nm, which would be perceived as blue and then coated and/or covered with a phosphor to enable the blue to be converted to a more natural white light.

Light in the 380-420 nm wavelength is capable of killing or deactivating microorganisms such as but not limited to Gram positive bacteria, Gram negative bacteria, bacterial endospores, and yeast and filamentous fungi. Some Gram positive bacteria that can be killed or deactivated include *Staphylococcus aureus* (incl. MRSA), *Clostridium perfringens, Clostridium difficile, Enterococcus faecalis, Staphylococcus epidermidis, Staphyloccocus hyicus, Streptococcus pyogenes, Listeria monocytogenes, Bacillus cereus,* and *Mycobacterium terrae*. Some, Gram negative bacteria include *Acinetobacter baumannii, Pseudomonas aeruginosa, Klebsiella pneumoniae, Proteus vulgaris, Escherichia coli, Salmonella enteritidis, Shigella sonnei,* and *Serratia* spp. Some bacterial endospores include *Bacillus cereus* and *Clostridium difficile*. Some yeast and filamentous fungi include *Aspergillus niger, Candida albicans,* and *Saccharomyces cerevisiae*. Light in the 380-420 nm wavelength has been effective against every type of bacteria tested, although it takes different amounts of time or dosages dependent on species. Based on known results it is expected to be effective against all gram-negative and gram-positive bacteria to some extent over a period of time. It can also be effective against many varieties of fungi, although these will take longer to show an effect.

LED lighting systems that use 405 nm and/or in the range of 380-420 nm antimicrobial properties have recently been tested and implemented into products available in the market for general lighting purposes. These devices and/or systems use wavelengths between 380-420 nm, 405 nm for example and coat the 405 nm LEDs with phosphor so that both white light and antimicrobial light is delivered from the lighting system. The rate at which these lighting systems kill unwanted microbes varies based on the level of light and or lux output being projected onto a specific surface. Although these LED lights take longer to kill microbes compared to the lower UV wavelength alternatives, they are safer for people. An important variable in testing the efficacy of 405 nm light is the lux level of lights being used. Lux is the standard unit of measure of illuminance and luminous emittance, measuring the perceived power of light per unit area. It is equal to one lumen per square meter and is used as a measure of brightness, as perceived by the human eye, of light that hits or passes through a surface, and similarly would be in the case of the proposed invention described herein, onto and/or through living tissue to reduce and or eliminate microbial infections.

LEDs are also available in various IR wavelengths and can likely be manufactured to offer any wavelength in the range of 700 nm to 1 mm in the IR spectrum. The benefit of LEDs is that they can be manufactured to deliver very specific wavelengths.

Short-wave infrared (SWIR-/NIR-II) LEDs ("SWIR-LEDs") used in imaging have received increased attention and fall within the near-IR wavelength bands.

LEDs are semiconductor devices that produce light when a current is supplied to them. LEDs are intrinsically DC devices that only pass current in one polarity and have historically been powered and/or driven with constant current or constant voltage DC power supplies however recently LEDs have also been driven with AC voltages and/or rectified high voltage AC. LEDs can therefore be driven with AC and/or DC using complex, or simple power supplies and/or drivers, as well as with batteries as they have been in flashlights and other battery backup lighting systems. With the recent high growth and use of LED technology, LEDs have more recently often been designed into human centric lighting systems, plant growth systems, dermatology lighting systems and are more often being tested and developed for medical applications.

The epitaxial growth process of LEDs is reasonably precise and allows LED chip manufacturers to provide many various wavelength options. LED chips can be packaged with or without phosphors based on the designer light output color (ie. red, green, blue, violet) and/or visible or non-visible wavelength. Phosphors and/or nano-crystals can be used to convert the original output color and/or wavelength of a LED chip to a white and/or near white light color temperature. White light color temperatures are often measured in Kelvins "K" and can range from 1500K (in the red and/or candlelight range) to 7500K (more blue Ultra Daylight) range. Wavelengths, colors and/or color temperatures of light can be combined, mixed and/or modulated to produce net resultant outputs of different wavelengths, colors and/or color temperatures of light. This can be done with various types of software and/or hardware including but not limited to artificial intelligence "AI", electronic and/or software drivers, microprocessors, controllers, modulation methods, pulsed outputs and other such methods and/or devices that could be integrated in various types of lighting devices or systems according to the inventions described herein including but not limited to the proposed antimicrobial lighting devices for eliminating microbial infections in living species and/or living tissue, lighting devices and/or systems or devices comprising video displays as described herein.

LED chips are most often packaged with similar types of wavelengths if more than one chip is integrated in a single package, assembly or substrate such as blue/blue, red/red and so on. However red, green, and blue ("RGB") is also a common LED package. The RGB LEDs and/or lighting systems are often used in LEDs signs, displays, theater lighting and other lighting systems where color changing is a requirement. Some LED packages and/or assemblies have included blue and red chips or LED packages mixed together to increase the quality of the light and/or color rendering index ("CRI"). An alternative to using red LEDs is to just use blue and adjust the phosphor coating on the blue LED chips so that the white light output from the LED package and/or assembly has an increased red color.

In recent months, the world has been affected with a global pandemic resulting in a significant number of rapidly increasing infections and loss of life as a result of the Coronavirus, more specifically COVID-19. COVID-19 is another dangerous respiratory infection that can lead to pneumonia and death similar to SARS and MERS. Doctors and scientists around the world are working fast to develop treatments, vaccines, equipment and more to help combat the global pandemic. Some of the proposed solutions being used include already approved medications such as hydroxychloroquine however many others are not yet tested and can have negative effects on the human living species they're being designed for.

Past viral pandemics and now COVID-19 have proven to put the worlds populations and economies at risk. Unfortunately, it's likely that this can occur again one day in the future. Other infections, for example kidney, diabetic limb and more occur on a regular basis and often lead to undesirable negative results. New solutions are needed for current and future microbial infectious diseases. It is contemplated to use a non-pharmaceutical technology-based solution using light to kill microbial infections within living species and/or tissue.

Therefore, it would be advantageous to provide antimicrobial lighting devices and methods for eliminating microbial infections in living species including but not limited to humans, animals, mammals and other living species.

There is growing medical evidence that too much exposure to blue light may cause permanent eye damage, contribute to the destruction of the cells in the center of the retina; and play a role in causing age-related macular degeneration, which can lead to vision loss. Melanin is the substance in the skin, hair, and eyes that absorbs harmful UV and blue light rays. It's the body's natural sunscreen protection. Higher amounts of melanin afford greater protection, but as a person ages, the person loses melanin, so that by age 65 half of the protection is gone making us more susceptible to eye disease such as macular degeneration. The retina is a very thin, multi-layered tissue covering the inner eyeball. The retina can be harmed by high-energy visible radiation of blue/violet light that penetrates the macular pigment found in the eye. A low macular pigment density may represent a risk factor for age-related macular degeneration by permitting greater blue light damage to the retina.

A Harvard medical study states that "High Energy Visible ("HEV") blue light has been identified for years as the most dangerous light for the retina. After chronic exposure, one can expect to see long range growth in the number of macular degenerations, glaucomas, and retinal degenerative diseases". And a paper published by the American Macular Degeneration Foundation ("AMDF") reports that "the blue rays of the spectrum seem to accelerate age-related macular degeneration ("AMD") more than any other rays in the spectrum".

Red light therapy is a safe, natural way to protect vision and heal eyes from damage and strain, as shown in numerous peer-reviewed clinical studies. Wavelengths of both red light (in the mid-600 nm range) and near infrared light (in the mid-800 nm range) have been tested in multiple clinical trials and found to be safe and effective for ocular health and vision protection. People with age-related macular degeneration and glaucoma have shown significantly improved vision with the aid of light therapy treatments, and people with eye injuries have experienced faster healing, with less inflammation.

Adenosine triphosphate ("ATP") is an energy-carrying molecule known as "the energy currency of life" or "the fuel of life," because it's the universal energy source for all living cells. Every living organism consists of cells that rely on ATP for their energy needs. ATP is made by converting food into energy. It's an essential building block for all life forms. Without ATP, cells wouldn't have the fuel or power to perform functions necessary to stay alive, and they would eventually die. All forms of life rely on ATP to do the things they must do to survive.

Red and NIR light improves the efficiency of the cellular respiration process and helps a body make and use ATP energy more effectively. Light does this by impacting the mitochondria. Red light therapy can increase the number of mitochondria, and also boost their function in the cell.

Age-related macular degeneration affects nearly 200 million people worldwide. It's a common condition that occurs as eyes age and core ATP energy production decreases in the cells of eyes. Declining ocular cells lead to inflammation, cell degeneration, and eventually visual decline and the day-to-day problems that come with it. There is currently not a cure.

One of the primary mechanisms of action for red light therapy is that natural light stimulates the mitochondria in cells to produce more ATP energy. Red light therapy works against the main factor in macular degeneration, helping the cells in eyes work efficiently and produce energy, even as an eye ages. Therefore, red, near-IR, mid-IR, and far-IR light and/or wavelengths deliver safe therapeutic wavelengths of natural light directly to the mitochondria in cells. These red, near-infrared, mod-infrared and far infrared wavelengths reduce oxidative stress, so a body is able to make more usable ATP energy to power itself. This increases function, speeds healing, and lowers inflammation & pain, as demonstrated in numerous peer-reviewed studies.

It has been reported that people who received red light and IR treatments experienced significant increases in visual acuity, or vision sharpness as measured by how well they could make out distant letters and numbers. Significant decreases in edema and hemorrhaging, which means less distorted vision and broken blood vessels. No negative side effects, as is common in nearly every study about red light.

Retinitis pigmentosa is the most common cause of inherited blindness. This degenerative disease breaks down retinal cells and leads to difficulty seeing at night, a loss of peripheral vision, and can eventually lead to blindness. Researchers in 2012 examined the use of red light therapy in a mammal model of retinitis pigmentosa, finding that natural light treatments promoted mitochondrial integrity and function, prevented photoreceptor cell death, and preserved retinal function. To establish the safety of red light therapy, researchers conducted the trial with 670 nm red light and 830 nm near infrared light. They found both to be safe for clinical use, and even found the near infrared light "exerted a robust retino-protective effect."

Research shows red and or IR Light Therapy is an effective natural glaucoma treatment. Glaucoma is a group of eye diseases that results in optic nerve injuries and cause vision loss over time. Glaucoma affects more than 60 million people, and chances of developing it increase as you age. Because there is no cure for glaucoma, managing symptoms and vision loss is the focus of current treatments, often for many years. Fortunately, red light therapy is proving in recent trials to be a safe, effective, and natural treatment for glaucoma, with none of the discomfort or side effects of prescription medications, eye drops, or surgery. Red and/or IR light treatments improve the effects of glaucoma and prevent vision loss by protecting the cornea and retina, especially against the ocular pressure and fluid buildup, which is one of the main complications that occurs with glaucoma cases. Clear liquid builds up in the front of the eye, and can cause damage to the optic nerve, which leads to the death of eye cells and with it the gradual loss of vision. Corneal cells, the ones tasked with keeping the cornea transparent so light can enter, are especially at risk from this pressure buildup. A 2017 study determined that red light therapy treatments absorbed by patients' eyes reduced this damage to corneal cells and even promoted their growth, enhancing the cells' survival chances and protecting against glaucoma-related vision loss. Protecting the Retina: Similar results were reported in a 2016 trial that analyzed retinal cells. A retina is responsible for creating visual perception, and sending messages to the brain. Without this cellular function, a person is unable to make sense of the world visually. In laboratory models of mammal vision, researchers found that red light therapy helps protect retinal cells when they were threatened by ocular pressure.

Therefore it would be advantageous to provide a lighting device configured to provide and/or emit at least one or more of red light and/or IR wavelengths including but not limited to at least one or more of near-IR, mid-IR, and/or far-IR wavelengths of energy and have such a lighting device be configured to mount to a video display, and/or have at least one or more (including all) of the red and/or IR wavelength light sources be integrated into the video display such that the red and/or IR wavelengths emitted can be directed toward the eyes of the display viewer for controlled and/or constant periods of time while looking at the display for the purposes of providing therapeutic red and/or IR wavelength emissions and health benefits to the viewers vision and/or other portions of the body. The lighting device may be configured to receive data and/or control signals from the video display device to control the light emissions of the lighting device.

It would further be advantageous to combine phosphor coated near-UV light sources and/or lighting devices with the red and/or IR wavelength emissions such that the near-UV light sources could provide both lighting onto a surface or to an area and simultaneously kill bacteria on the surface and/or on the area.

It would further be advantageous to provide a lighting device configured to provide and/or emit at least one or more of red light and/or IR wavelengths including but not limited to at least one or more of near-IR, mid-IR, and/or far-IR wavelengths of energy and have such a lighting device be configured to mount to a display, and/or have at least one or more (including all) of the red and/or IR wavelength light sources be integrated into the display as a part of the display light sources used to produce moving or still video images on the display, or integrated into the display housing, such that the red and/or IR wavelengths emitted can be directed to the eyes of the display viewer for controlled and/or constant periods of time at specific times of the day for improving and/or providing health benefits to the viewers vision.

It would further be advantageous to provide such a lighting device that can be powered with a separate power source, a battery, or with the power source from a video display.

It would further be advantageous to provide electronic displays, including but not limited those using one or more of the following display technologies: LED Displays, OLED Displays, Micro-LED Displays, Quantom-Dot "QLED" Displays, Organic Light Emitting Transistor "OLET" Displays, Nano Cell and LCD displays or other display technologies, with methods and devices that provide at least one or more of constant, pulsed (at low or high frequency) and/or timed outputs of red and/or IR wavelength emissions to the human eye independently and/or simultaneously with conventional display lighting and/or backlighting used for lighting such displays in applications and markets where displays are used including but not limited to in handheld devices, portable communications devices, monitors, portable computers, desktop computers, head mounted displays, electronic signs and more.

It would further be advantageous to provide displays using at least one of OLED Displays, Micro-LED Displays, Quantom-Dot "QLED" Displays, Organic Light Emitting Transistor "OLET" Displays, Nano Cell and LCD displays or other display technologies along with Dynamic Pixel Tuning "DPT" of such display technologies including but not limited to Micro-LEDs that can emit wavelengths of red, green, blue, and IR wavelengths of light.

It would further be advantageous to provide a display that can either provide backlighting using red light and/or IR emissions, or provide red light and/or IR light emission that can be controlled in level of brightness and/or or intensity, duration of emission time, time of day the emission occurs with such time of day being related to the GPS location of the device and/or the display device and it's clock within a given geographical location, direction of the emission and/or focus of the emission on a person and/or a person's eye. It would be advantageous to use at least one or more of optics, dynamically and/or electronic controlled optics, lenses, lasers, is contemplated that using processors and/or controllers, hardware and software drivers, sensors including but not limited to camera sensors and/or sensors that can detect the movement of a person, sensors within the display that can be at least one of pre-set by the manufacturer, controlled by the user, or controlled by information received by the device having the display with red and/or IR wavelength emission.

It would further be advantageous to have first and second devices in communication with each other to provide information to at least one of the device displays to enable the device to activate when red and/or IR wavelengths should be emitted from a display towards the eye of a person looking at the display. The first device may be a portable telecommunications device and the second device may be a computer, sensor, clock, timer, or a wearable device including but not limited to wearables that sync to another electronic device and or wearables that provide biofeedback information and can transmit such information to a device using wireless and/or wired communications.

It would further be advantageous to use the light emitting devices and/or pixels used to provide display image lighting, as light sources that also provide red and/or IR wavelength emission to the viewers eyes.

It would also be advantageous to design circuits, devices and lighting systems that use LEDs, OLEDs, laser, halogen, xenon, mercury vapor, or any other lighting technology that can be used to achieve and deliver the desired results described herein.

It would further be advantageous to provide a wearable and/or eyewear device configured be worn on the face and/or head of a person and/or user to provide and/or emit at least one or more of red light and/or IR wavelengths including but not limited to at least one or more of near-IR, mid-IR, and/or far-IR wavelengths of energy into and/or in the direction of the person's eyes and/or temple region to provide retinal and PBM light therapy to the person and/or user. Such a wearable lighting device be configured to be a solid, semi-solid or flexible or combination of solid, semi-solid and/or flexible wearable device such as glasses and/or eyewear including but not limited to smart eyewear which may include one of more of prescription vision lenses, non-prescription magnification lenses, sun reduction and/or blocking lenses, video display features, audio input and/or output features. Such a device may further be configured to include a microphone and audio speakers, including but not limited to bone conduction technology speakers such that the red, IR and/or combination of red and IR wavelengths emitted can be directed toward and/or into the eyes and/or temple region of the person and/or user. By use of software or other methods known to those skilled in the art, the wavelength emissions can be automatically or user selectively provided at a specific time of day (with such time of day being related to the GPS location of the device and/or the display device and it's clock within a given geographical location) for a controlled and/or constant periods of time while wearing the device to provide one or more of the health benefits described herein according to the invention. It is contemplated by the inventors that such an eyewear device may further be configured to emit blue light at a specific time of the day such as the morning, for a specific controlled period of time to provide a person with light that will stimulate waking up, alertness and other health benefits of blue light. Such blue light could be emitted independently or in conjunction with one of more of the other red and/or IR wavelengths that will counteract any of the negative effects of blue light on the retina and provide health benefits to the retina as described herein.

It is further contemplated by the inventors that a simpler form of an eyewear device may be configured to include the combination bone conduction speakers and a microphone along with prescription lenses and/or magnification lenses, sunglass lenses and/or smart lenses as a replacement for hearing aids for people that wear eyewear. The microphone may be configured to detect sound that is then output from the bone conduction speakers. Such an eyewear device may further be configured to provide light emission of red and/or IR as described herein according to the inventions described herein.

It would further be advantageous to provide a wearable anti-infective lighting radiation device configured to provide and/or emit at least one or more of UV, near-UV, red, near-IR, mid-IR, and/or far-IR wavelengths of energy into the esophagus of a person and/or living species, or onto the front of the neck, chest and/or neck and chest of a person and/or living species such that the wavelengths of energy emitted pass through the tissue of the person and/or living species to reach the esophagus and provide therapeutic benefits of PBM as well as other benefits including but not limited to anti-inflammatory, vasodilation, localized and/or focused heating which according to the invention may provide benefits for anti-cancer, anti-asthma, Chronic obstructive pulmonary disease ("COBD"), chronic cough, and other breathing and/or esophageal type ailments that could be treated with such a wearable Anti-Infective Radiation device according to the invention. Such a device would be configured to include one or more of the other following features including but not limited to providing different levels of brightness and/or intensities of output wavelengths of visible and/or non-visible light by switching or controlling the wavelengths in response to one or more control devices and/or methods including but not limited to sensors, controllers, microprocessors, biofeedback, integrated circuits, and/or other wavelength management and/or control circuitry or user or operator of the device. The sensors can include but not be limited to sensors and/or camera sensors capable of sensing one or more of movement or location of a person and/or person's eyes and/or face, temperature sensors including but not limited to ambient or body temperature, sound, vibration, electrical signals including but not limited to a person's electrical signals, the infrared emissions of a person, humidity, blood, blood pressure, blood oxygen levels, microorganisms, organisms, biofeedback, bio-resonance, proximity and/or location of a person and/or device including but not limited to an electronic device, oxygen, enzymes, fluids and/or minerals.

The present invention is provided to solve these and other issues.

SUMMARY

The present invention relates to methods and devices for delivering and projecting antimicrobial and/or infrared "IR" lighting radiation (anti-infective light radiation or "ALR") for eliminating infections internal to living species including but not limited to humans, animals, mammals and other living species. The present invention uses lighting devices, that from the exterior of a living species and/or when integrated or placed within the interior of a living species, project sufficient levels of visible light and/or IR radiation directly onto and/or through one or more layers of living tissue so that the visible light and/or JR radiation energy reaches infectious organisms.

The present invention may also use antimicrobial lighting devices that produce one or a combination and/or group of electromagnetic radiation energy wavelengths in the range of 350-450 nm, and more specifically 380-420 nm, and/or use red and/or infrared electromagnetic radiation ("IR") lighting and/or devices that produce one or a combination and/or group of electromagnetic radiation energy wavelengths in the range of 625-1200 nm. In some instances, the present invention individually uses the IR radiation and/or wavelengths to increase heat onto and/or near the infectious organisms. The invention may simultaneously apply and/or project the antimicrobial lighting and the Red and/or IR lighting radiation and/or wavelengths onto and/or near the infections to reduce and/or kill invading and/or unwanted infectious organisms, on and/or within a living species.

Some disclosed inventions are directed to anti-infective lighting radiation ("ALR") methods and devices "ALRMD") for eliminating infections in living species. ALRMD can include, but is not limited to, using light emitting diodes, fluorescent, halogen, or any other light sources that can emit any single wavelength or combination of wavelengths in the range of visible and/or non-visible light spectrums such as wavelengths including but not limited to UV, near UN, and/or other visible and/or non-visible wavelengths at Various levels of constant, pulsed and/or modulated energy intensities that may be used to harm, destroy and/or prevent infectious organisms from multiplying on environmental surfaces, and more specifically as described herein, on or within living species.

Such ALRMD may be powered with AC mains voltage sources, low voltage power supplies, batteries and/or any form of power source sufficient to power a specific ALRMD and/or system. The ALRMD may provide different levels of brightness and/or intensities of output wavelengths of visible and/or non-visible light by switching or controlling the wavelengths in response to one or more control devices and/or methods including but not limited to sensors, controllers, microprocessors, biofeedback, integrated circuits and/or other wavelength management and/or control circuitry or user or operator of the ALRMD. The sensors can include but not be limited to sensors capable of sensing one or more of movement or location of a person and/or person's eyes and/or face, temperature including but not limited to ambient or body temperature, electrical signals including but not limited to a person's electrical signals, the infrared emissions of a person, humidity blood, blood pressure, blood oxygen levels, microorganisms, organisms, biofeedback, bio-resonance, proximity and/or location of a person and/or device including but not limited to an electronic device, oxygen, enzymes, fluids and/or Minerals.

Such ALRMD may also include circuitry to allow for controlling and/or programming the output wavelengths for timing, duration, which wavelengths to be used and when as well as the intensity levels of such wavelengths. The ALRMD may include, wired and/or wireless communication and/or control, by medical personnel and/or other practitioners, operators and/or users of the ALRMD.

According to one aspect, the present invention provides methods and devices including but not limited to anti-infective light radiation and/or antimicrobial lighting devices for eliminating microbial infections in living species and/or living tissue. The present invention specifically relates to anti-infective light radiation ("AILR") methods and devices ("AILR-MD") for eliminating microbial, parasitic, cancerous and other infections on the exterior and/or interior of living species including but not limited to humans, animals, mammals and other living species by:

a.) providing and using lighting devices and/or systems, that from the exterior of a living species and/or when integrated or placed within the interior of a living species, will project and/or radiate sufficient levels of electromagnetic radiation of light and/or IR energy directly onto and/or through one or more layers of living tissue so that the light and/or IR energy reaches unwanted infectious organisms, with such devices and methods including but not being limited to:

b.) providing and using antimicrobial lighting devices that produce one or a combination and/or group of electromagnetic radiation wavelengths in the range of 350-450 nm, and more specifically 380-420 nm, and/or using red and/or infrared ("IR") lighting and/or devices that produce one or a combination and/or group of electromagnetic radiation wavelengths in the range of 625-1200 nm, and;

c.) individually using the IR electromagnetic radiation wavelengths to increase heat onto and/or near the infectious organisms, and/or;

d.) simultaneously or by alternating turns, applying and/or projecting the antimicrobial lighting as a first set of electromagnetic radiation wavelength(s) and the red and/or IR lighting electromagnetic radiation wavelength(s) as a second set of electromagnetic radiation wavelength(s) that are focused onto and/or near the microbial type and other infections within a living species to reduce and/or kill invading and/or unwanted infections and/or microorganisms on and/or within a living species, individually and/or in combination hereinafter AILR and/or AILR-MD.

According to another aspect of the invention, the antimicrobial lighting devices and/or systems of the invention can be used to kill unwanted parasites, organisms and/or microorganisms and/or infections, hereinafter "infections", (for example COVID-19, MERSA, cancer, or other infections) infecting a living species, and the red and/or IR lighting devices and/or systems can be used to increase heat directly onto and/or near the targeted, unwanted infections similar to a fever thereby slowing down the infections ability to multiply and/or infect more healthy cells and/or tissue. The antimicrobial light and/or in conjunction with the IR heat delivered as a targeted, focused and/or localized fever effect would support and/or assist the immune systems white blood cells to better surround the infectious organisms thereby eventually slowing and/or killing off the infection within the living species just as they do when a living species produces a fever.

Using 100-350 nm UV lighting can be more dangerous and challenging than using 350-1400 nm lighting in medical devices and/or applications where energy using these wavelengths on or within living beings and/or species requiring rapid elimination of infectious microbial diseases that are creating risk of damaging and/or loss of limbs, organs and/or life.

According to one aspect of the invention, with proper considerations relating to process, implementation, system design, time/duration and/or energy levels, concentration and/or placement of such energy and other criteria, antimicrobial lighting devices that deliver 380-420 nm, and potentially wavelength ranges of 350-450 nm that are still within the outer edge or just outside of the UV spectrum, and/or devices that deliver red and/or IR light and/or energy separately and/or simultaneously with the antimicrobial lighting devices, would therefore be much safer to use in medical lighting devices and/or systems designed for eliminating microorganisms and/or infections that are invading living species, organs and/or tissue. Such devices and/or systems could be used in medical treatments for reducing and/or eliminating unwanted microorganisms within living species and/or living tissue without the same negative effects of UV lighting below 350 nm wavelengths.

According to another aspect of the invention, since light wavelengths in the 380 nm to 420 nm range have proven to be effective in killing over 99% of bacteria over time based on intensity of light and specific wavelengths, it is contemplated that placing light internally into a living species organ, or by projecting sufficient levels of light energy and/or intensity needed to pass through living tissue and reach the specific infectious organisms, would effectively and rapidly reduce and/or kill the invading infectious organisms over a shorter period of time compared to not treating the infection with the AILR-MD.

According to another aspect of the invention, with IR light/energy wavelengths in the 700-1400 nm range being proven to increase heat, improve oxygen levels, increase circulation, reduce inflammation and deliver other health benefits, it is contemplated that placing such light and/or wavelength energy(s) internally into a living species organ, or by projecting sufficient levels of light energy needed to pass through living tissue and reach the specific infectious organisms, would aid in effectively and rapidly reducing and/or killing the invading infections over a shorter period of time compared to not treating the infection with light AILR-MD.

According to another aspect of the invention, it is further contemplated that by concentrating and/or projecting such light wavelengths of 350-450 nm and more specifically 380-420 nm, with or without phosphor conversion of such wavelengths, (hereinafter visible anti-infective lighting or "VAIL"), and/or by concentrating and/or projecting red 650-720 nm, and more specifically IR light/energy wavelengths of 700-1200 nm (hereinafter infrared fever lighting or "IFL"), and placing, projecting and/or concentrating such light and/or electromagnetic radiation wavelength energy(s) onto and/or internally into a living species organ, or by projecting sufficient levels of such electromagnetic radiation energy(s) needed to pass through living tissue and reach the specific infectious organisms, would effectively and rapidly reduce and/or kill the invading infections over a shorter period of time compared to not treating the infection with AILR-MD.

According to another aspect of the invention, it is contemplated that:
a. one or a combination and/or group of VAIL wavelengths could be used in devices according to the invention, and/or;
b. one or a combination and/or group of IFL wavelengths could be used in devices according to the invention, and/or;
c. one or a combination and/or group of both VAIL and IFL wavelengths could be used in alternating modes and/or simultaneously in separate and individual, or single medical lighting devices and/or systems, in either respect together or separately considered ALRMD, according to the invention.

According to another aspect of the invention, VAIL and/or IFL light sources and/or devices could be integrated together and/or combined into a single device to provide an output of both forms and/or categories of antimicrobial light (VAIL) for reducing and killing infectious organisms, and IR wavelength energy(s) (IFL) to reduce inflammation and/or create and/or induce a targeted fever effect on certain cells simultaneously for the purposes of proving ALRMD procedures and devices for killing unwanted infections and/or organisms within a living species. The VAIL and IFL light sources and/or devices could provide one or a combination of a constant output, pulsed output, modulated output, sensor responsive output, time based output or variable output of one or more light and/or wavelengths of radiation energy from one of both VAIL and IFL light sources and/or devices.

According to another aspect of the invention, VAIL and IFL light sources and/or devices could operate on constant voltage, constant current, AC voltage, DC voltage, pulse width modulation "PWM", battery power, universal voltage input power supplies, inverters, solar power or any other form of power that could power and/or drive electronic circuits and/or lighting devices.

According to another aspect of the invention, ALRMD and/or treatments could be used and/or provided separately, or in conjunction with other medical procedures and/or treatments including but not limited to drug therapy, surgery, sensing, photo imaging, bronchoscopy, ultrasound, measuring, monitoring, oxygen delivery, sonic, nano-medical robots and other procedures. A single device could provide and/or deliver one or a combination of VAIL and/or IFL energy treatment. VAIL and/or IFL devices could be integrated and/or combined with other medical devices and/or non-medical items including but not limited to nano-medical robots, endoscopes, bronchoscope, cameras, ventilators, electrical stimulators, implanted devices, wearable devices, full and/or partial patient enclosures, medical rooms, ceilings, walls, floors, patient beds and/or tables, chairs, prosthetics, ceiling lights, light bulbs, portable devices, communications devices, video displays, handheld devices, and more.

According to another aspect of the invention, one example method of treatment could include but not be limited to a person partially or completely sitting, laying, being covered, wrapped and/or enclosed within a ALRMD procedure device for a period of time for killing unwanted infections and/or organisms within a living species.

According to another aspect of the invention the ALRMD wavelengths could be set and/or tuned at one or more specific selected wavelengths 405 nm and/or 850 nm for example, that fall within the range of 350 nm-450 nm and/or 700 nm-1400 nm based on the infection, information, feedback data and/or response of the infectious cells, amount and/or depth of tissue needing to be penetrated, or other factors. The setting, control and/or tuning of the AILMD output wavelengths could be done manually, electronically and/or automatically according to the invention and the setting, control and/or tuning of such wavelengths could be at one or more similar or different levels of output energy levels per output wavelength. Planck's equation $\lambda=hc/e$ could be used to calculate the electromagnetic radiation output energy and or to set the desired output wavelength energy(s). An output VAIL wavelength of 405 nm could be provided at 10 watts or 100 lux, while an IFL output wavelength of 850 nm could be provided at 20 watts for example, but not limited to these specific power levels and/or wavelengths. One or more wavelengths and/or output energy levels from the ALRMD could also be set to be delivered in various ways including but not limited to a constant, pulsed, pulse width modulated, modulated or timed and such outputs could be controlled, set and/or programmed by the user of the ALRMD and/or systems.

According to another aspect of the invention, one example method of treatment could include but not be limited to the following: In the case of a respiratory infection such as SARS or COVID-19 were to invade the respiratory track or lungs of a human, or a staphylococcal infection were to invade a diabetic person's leg, or travel to another organ, using one wavelength, or a combination of radiation wavelengths and/or light energy between the ranges of 350-1400 nm could be used to reduce and/or kill microbial infections on and/or within living species. For example, 405 nm of light energy at specific desired and controlled durations of time, power, distribution and/or beam angles, and/or intensity levels could be administered to reduce and/or kill the microbial infection inside the lungs or other parts of the body, or within other living species and/or tissues or organs according to the inventions and methods described herein. Another option would be to use and deliver IR energy somewhere in the ranges of 700 nm-1 mm in conjunction with such antimicrobial light energy. The IR lighting devices and/or wavelengths can be used to reduce inflammation and/or increase heat directly onto and/or near the targeted, unwanted infections similar to a natural fever response thereby slowing down the infections ability to multiply and/or infect more healthy cells and/or tissue. The antimicrobial light along with the heat/fever delivered as a targeted, focused and/or localized area would support and/or assist the immune systems white blood cells and/or antimicrobial light energy, to better and more successfully fight off the infectious cells thereby eventually slowing and/or killing off the microbial infection within the living species.

According to another aspect of the invention, such treatments and/or devices could include for example but not be limited to, a flexible fiber optic and/or quartz fiber optic type cable having sidewall emission of light along at least a portion of the length of cable, or a bronchoscope having an outer layer that would be illuminated with one or more wavelengths somewhere within the range of 350-450 nm, and more specifically 380-420 nm, could be inserted into the lungs and light up the inside of the lungs with antimicrobial light to reduce and/or kill harmful infectious diseases. Simultaneously or alternatively a light source could be placed inside the living species under the skin and near the exterior walls of an organ such as the lung, or outside of the living species facing into the skin and a specific targeted organ and/or area, and project a sufficient level of wavelength energy needed to penetrate layers of living tissue and reach the microorganisms would effectively and rapidly reduce and/or eliminate unwanted microbial infections.

According to another aspect of the invention, many various forms of lighting devices and/or systems could be designed and produced to be optimized for various medical requirements where antimicrobial lighting devices for eliminating such infections in living species would be used and applied including but not limited to flexible, rigid, flat, linear, tubular, round, rectangular, stranded, flat panels or other structures that can be designed to deliver light at the desired ALR wavelengths.

According to another aspect of the invention, as long as the desired ALR wavelengths and energy levels could be achieved and controlled, and devices could be designed to achieve the desired objective for their applications of use, technologies used in such lighting devices and/or systems for eliminating microbial infections in living species could include but not be limited to LEDs, OLEDs, micro-LEDs, laser diodes, bioluminescent organisms, incandescent, halogen, xenon, mercury vapor, fluorescent or other light sources, devices or materials that can emit one or more of the required wavelength including but not limited to graphene. Our bodies radiate far-infrared energy from 3 to 50 microns through the skin, with most output at 9.4 microns. The wavelength of graphene's "far-infrared" is 4~16 microns, which is compatible with the human body and is easily absorbed. Far infrared rays are energy waves that help activate body systems and functions.

According to another aspect of the invention, devices and/or techniques to deliver one or more wavelengths of AIL and/or IR energy from devices and/or lighting devices designed to provide the benefits and features proposed herein may include but not be limited to one or more of one or a combination of housings, electrical conductors, thermal and/or heat conductors, optics, lenses and/or lens covers, powered optics and or lenses, heat sinks made of in whole or in part, and/or coated in whole or in part with graphene materials that may be energized in one form or another including but not limited to with resonance, ambient heat, heat transfer, heat conversion, pulses of light pulsed at time intervals of in the range of more than one minute to time intervals of one or more femtoseconds, and or electric power such that one or more of one or a combination of such housings, optics, lenses and/or lens covers, heat sinks made of in whole or in part, and/or coated in whole or in part with graphene materials provide an emission of one or more "far-infrared" wavelengths within the range of 4~16 microns.

Another aspect of the invention is to combine the emission of one or more "far-infrared" graphene generated wavelengths within the range of 4~16 microns with one or a combination of more than one of the devices described below in Claims or as What is Claimed.

According to another aspect of the invention, devices and/or techniques to deliver light from lighting devices for eliminating such infections in living species could include but not be limited to fiber optics, laser, edge lit and/or light piping, optics, solid state controllable optics, reflectors and more. The antimicrobial light could be delivered in broad distribution covering large areas of infected and/or non-infected having tissue and/or cells, or concentrated with optics to focus the light onto a specific area of infected and/or non-infected tissue and/or cells.

According to another aspect of the invention, placing such ALR on and/or near living tissue and/or cells, where the amount of light radiation is sufficient enough to penetrate through one or more layers of living tissue and reach infections, such threatening infections could effectively be reduced and/or eliminated with and/or without the added support of unproven and/or undesired pharmaceutical drugs that may require more time to test, approve, don't work, or introduce risk and/or side effects.

According to another aspect of the invention, lighting devices including but not limited to LEDs may or may not use a phosphor to provide a phosphor converted output wavelength and/or color of light from the original output wavelength produced by the lighting device. If white light converted by phosphor is desired, it could be assembled similarly to a "blue-phosphor" LED device which includes a semiconductor LED that emits a majority of light/peak of light within the 380-420 nm wavelength range rather than wavelengths within the conventional range of approximately 450-495 nm, which would be perceived as blue. Light in the 380-420 nm wavelength is capable of killing or deactivating microorganisms such as but not limited to Gram positive bacteria, Grain negative bacteria, bacterial endospores, and yeast and filamentous fungi. Some Gram positive bacteria that can be killed or deactivated include *Staphylococcus aureus* (incl. MRSA), *Clostridium perfringens, Clostridium difficile, Enterococcus faecalis, Staphylococcus epidermidis, Staphylococcus hyicus, Streptococcus pyogenes, Listeria monocytogenes, Bacillus cereus*, and *Mycobacterium terrae*. Some, Gram negative bacteria include *Acinetobacter baumannii, Pseudomonas aeruginosa, Klebsiella pneumoniae, Proteus vulgaris, Escherichia coli, Salmonella enteritidis, Shigella sonnei*, and *Serratia* spp. Some bacterial endospores include *Bacillus cereus* and *Clostridium difficile*. Some yeast and filamentous fungi include *Aspergillus niger, Candida albicans*, and *Saccharomyces cerevisiae*, Light in the 380-420 nm wavelength has been effective against every type of bacteria tested, although it takes different amounts of time or dosages and/or energy levels dependent on species. Based on known results it is expected to be effective against all gram-negative and gram-positive bacteria to some extent over a period of time. It can also be effective against many varieties of fungi, although these will take longer to show an effect. The LED, according to embodiments of the disclosure, may be surrounded by a phosphor material capable of absorbing and convening some portion of that anti-microbial light emitted from the LED (380-420 nm) to an alternative wavelength or wavelengths. This LED device can have a combination of selected phosphors, such as but not limited to Lutetium Aluminum Garnet and Nitride, that when combined at the proper ratios can emit a light perceived as white or a hue of white. This example LED device can have a CRI equal to or greater than 70. In some embodiments, this example LED device can have a CRI equal to or greater than 80. A percentage of spectral content of light emitted from the example LED device with approximately 380-420 in wavelength can be equal to or greater than 20% In some embodiments, light with wavelengths in the range from approximately 380-420 nm may comprise at least approximately 25%, 30%, 35%, 40%, 45%, or 50% of the total combined light emitted from the example LED device.

Another aspect of the invention is to combine at least one 380-420 nm blue LED chip and at least one 700 nm to 1 mm IR LED chip into a single blue/IR LED package ("BIR") LED package. The BIR LED package may include input and output and/or positive and negative "+/−" electrical connections to deliver a voltage and/or current to both of the LED chips at the same time, or alternately may have separate positive and negative electrical connections to each of the blue LED chip(s) sections and IR LED chip(s) sections allowing for different voltage and/or current levels to be delivered to the blue and IR LEDs chips in the single package. When more than one blue LED chip(s) is packaged and/or more than one IR LED chip(s) is packaged in a single package, the blue may be one or more different wavelengths (405 nm and 410 nm for example), and the IR LED chips may be one or more different wavelengths (750 nm, 800 nm, and 850 nm for example). In addition to having the option of delivering different voltage and/or current levels to the different LED chips, different drive methods could be used for a single package. For example, the blue LED chips could be powered with a constant voltage or constant current, while the IR LED chips in the same package could be powered with the same/or different voltage or current level, but be pulsed on and off, or be pulsed at higher currents for a given period of time. Various drivers and/or power supplies as well as drive schemes could be used to drive such LED packages including but not limited to constant voltage, constant current, PWM, high frequency AC, high voltage AC or high voltage rectified AC, linear step drive, buck boost, or other LED driver and/or methods known to those skilled in the art. One or more of the blue LED chips inside the BIR package may or may not be surrounded and/or coated with a phosphor and more than one BIR chips and/or packages may be integrated into a single assembly and/or substrate. The assembly and/or substrate may be made of various material including but not limited to printed circuit board "PCB, metal core PCB "MCPCB", GaN, Sapphire, Silicon, aluminum, metal, glass, copper or other metals. Additionally, these and/or other materials may be used individually or in combination for heat sinking the BIR LED packages, assemblies and or AILR devices and systems.

Another aspect of the invention is to combine at least one LED package having at least one 380 nm-420 nm blue LED chip(s), and at least one LED package having at least one 700 nm-1 mm IR LED chip(s) onto separate substrates and/or printed circuit boards "PCBs" or a single substrate and/or PCB with such separate and/or or single substrates being capable of being integrated into separate and/or a single lighting device and/or system assembly thereby providing a Blue/IR Assembly or "BIR assembly". The BIR assembly may include input and output and/or positive and negative "+/−" electrical connections to deliver voltage and/or current to both blue and IR wavelength options at the same time, or alternately may have separate positive and negative electrical connections individually to one or more of the blue LED package(s) and IR LED package(s) allowing for different voltage and/or current levels to be delivered to the blue and IR LED chips and/or packages on the BIR assembly(s). When more than one blue LED package and/or more than one IR LED package is placed on a substrate, the blue may be one or more different wavelengths (405 nm and 410 nm for example), and the IR LED chips may be one or more different wavelengths (750 nm, 800 nm and 850 nm for example). In addition to having the option of delivering different voltage and/or current levels to the different LED chips, different drive methods could be used for a single package. For example, the blue LED chips could be powered with a constant voltage or constant current, while the IP LED chips in the same package could be powered with the same/or different voltage or current level, but be pulsed o and off, or be pulsed at higher currents for a given period of time. Various drivers and/or power supplies as well as drive schemes could be used to drive such LED packages including but not limited to constant voltage, constant current, PWM, high frequency AC, high voltage AC or high voltage rectified AC, linear step drive, buck boost, or other LED driver and/or methods known to those skilled in the art.

Another aspect of the invention is to combine at least one LED chip configured to have an peak emission of at least one wavelength between 585-700 nm (orange/red and/or red emission chip) with at least one LED chip having a peak emission of at least one wavelength between 700 nm-1 mm (IR LED chip) into a single red/IR LED package ("RIR") LED package. The RIR LED package may include input and output and/or positive and negative "+/−" electrical connections to deliver a voltage and/or current to both of the LED chips at the same time, or alternately may have separate positive and negative electrical connections to each of the red LED chip(s) sections and IR LED chip(s) sections allowing for different voltage and/or current levels to be delivered to the red and IR LEDs chips in the single package. When more than one red LED chip(s) is packaged and/or more than one IR LED chip(s) is packaged in a single package, the red emission from the package may be one or more different wavelengths (610 nm and 630 nm for example), and the IR emission from the package may be one or more different wavelengths (750 nm, 830 nm, and 850 nm for example). In addition to having the option of delivering different voltage and/or current levels to the different LED chips, different drive methods could be used for a single package. For example, the red LED chips could be powered with a constant voltage or constant current, while the IR LED chips in the same package could be powered with the same/or different voltage or current level, but be pulsed on and off, or be pulsed at higher currents for a given period of time. Various drivers and/or power supplies as well as drive schemes could be used to drive such LED packages including but not limited to constant voltage, constant current, PWM, high frequency AC, high voltage AC or high voltage rectified AC, linear step drive, buck boost, or other LED driver and/or methods known to those skilled in the art. One or more of the blue LED chips inside the RIR package may or may not be surrounded and/or coated with a phosphor and more than one RIR chips and/or packages may be integrated into a single assembly and/or substrate. The assembly and/or substrate may be made of various material including but not limited to printed circuit board "PCB, metal core PCB "MCPCB", GaN, Sapphire, Silicon, aluminum, metal, glass, copper or other metals. Additionally, these and/or other materials may be used individually or in combination for heat sinking the RIR LED packages, assemblies and or devices and systems.

Another aspect of the invention is to combine at least one LED package having at least one LED chip configured to have an peak emission of at least one wavelength between 585-700 nm (orange/red and/or red emission chip), and at least one LED package having at least LED chip having a peak emission of at least one wavelength between 700 nm to 1 mm (IR LED chip) onto separate substrates and/or printed circuit boards ("PCBs") or a single substrate and/or PCB with such separate and/or or single substrates being capable of being integrated into separate and/or a single lighting device and/or system assembly thereby providing a red/IR Assembly or ("RIR assembly"). The RIR assembly may include input and output and/or positive and negative "+/−" electrical connections to deliver voltage and/or current to both red and IR wavelength options at the same time, or alternately may have separate positive and negative electrical connections individually to one or more of the red LED package(s) and IR LED package(s) allowing for different voltage and/or current levels to be delivered to the red and IR LED chips and/or packages on the RIR assembly(s). When more than one red LED package and/or more than one IR LED package is placed on a substrate, the red may be one or more different wavelengths (610 nm and 630 nm for example), and the IR LED chips may be one or more different wavelengths (750 nm, 830 nm and 850 nm for example). In addition to having the option of delivering different voltage and/or current levels to the different LED chips, different drive methods could be used for a single package. For example, the red LED chips could be powered with a constant voltage or constant current, while the IR LED chips in the same package could be powered with the same/or different voltage or current level, but be pulsed on and off, or be pulsed at higher currents for a given period of time. Various drivers and/or power supplies as well as drive schemes could be used to drive such LED packages including but not limited to constant voltage, constant current, PWM, high frequency AC, high voltage AC or high voltage rectified AC, linear step drive, buck boost, or other LED driver and/or methods known to those skilled in the art.

It would further be advantageous to provide a lighting device configured to provide and/or emit at least one or more of red light and/or IR wavelengths including but not limited to at least one or more of near-IR, mid-IR, and/or far-IR wavelengths of energy and have such a lighting device be configured to mount to a display, and/or have at least one or more (including all) of the red and/or IR wavelength light sources be integrated into the display as a part of the display light sources producing moving and/or still video images (video images) on the display, or integrated into the display housing such that the red and/or IR wavelengths emitted can be directed to the eyes of the display viewer for controlled and/or constant periods of time for improving and/or providing health benefits to the viewers vision. It is contemplated by the inventors that a portion and/or the entire video display may be configured to emit only red, near-IR, mid-IR, and/or far-IR wavelengths of PBM light energy from for a controlled period of time independent of the display producing and/or generating any video images.

It would further be advantageous to provide such a lighting device that can be powered with a separate power source, or with the power source from the display including a battery, an electronic LED driver, a power supply connected to a battery and/or main power source.

It would be advantageous to use short-wave infrared (SWIR-/NIR-II) LEDs ("SWIR-LEDs") and/or ("SWIR-OLEDs") in some embodiments of the invention to provide IR wavelengths of light.

Another aspect of the invention is to add a plurality of IR wavelength light emitters to a quantum dot display and configure the IR wavelength emitters to emit IR and/or visible light at controlled levels of power and/or durations of time that the display is in use and viewed by a person. A quantum dot display is a display device that uses quantum dots ("QDs"), semiconductor nanocrystals which can produce pure monochromatic red, green, and blue light. Photo-emissive quantum dot particles are used in LCD backlights or display color filters. Quantum dots are excited by the blue light from the display panel to emit pure basic colors, which reduces light losses and color crosstalk in color filters, improving display brightness and color gamut. Light travels through QD layer film and traditional RGB filters made from color pigments, or through QD filters with red/green QD color converters and blue passthrough. Although the QD color filter technology is primarily used in LED-backlit LCDs, it is applicable to other display technologies which use color filters, such as blue/UV active-matrix organic light-emitting diode (AMOLED) or QNED/MicroLED display panels. LED-backlit LCDs are the main application of photo-emissive quantum dots, though blue OLED panels with QD color filters are being researched. Electro-emissive or electroluminescent quantum dot displays are a type of display based on quantum-dot light-emitting diodes (QD-LED; also EL-QLED, ELQD, QDEL). These displays are similar to AMOLED and MicroLED displays, in that light would be produced directly in each pixel by applying electric current to inorganic nano-particles. Manufacturers asserted that QD-LED displays could support large, flexible displays and would not degrade as readily as OLEDs, making them good candidates for flat-panel TV screens, digital cameras, mobile phones and handheld game consoles.

It would further be advantageous to provide electronic displays, including but not limited those using one or more of the following display technologies: LED displays, OLED displays, micro-LED displays, quantum-Dot ("QLED") displays, organic light emitting transistor ("OLET") displays, nano cell and LCD displays or other display technologies, with methods and devices that provide at least one or more of constant, pulsed (at low or high frequency) and/or timed outputs of red and/or IR wavelength emissions to the human eye independently and/or simultaneously with conventional display lighting and/or backlighting used for lighting such displays in applications and markets where displays are used including but not limited to in handheld devices, portable communications devices, monitors, portable computers, desktop computers, head mounted displays, electronic signs and more.

It would further be advantageous to provide a display that can either provide backlighting using red light and/or IR emissions, or provide red light and/or IR light emission that can be controlled in level of brightness and/or or intensity, duration of emission time, total time within a day, time of day the emission occurs with such time of day being related to the GPS location of the device and/or the display device and it's clock within a given geographical location, direction of the emission and/or focus of the emission on a person and/or a person's eye. It would be advantageous to use at least one or more of optics, dynamically and/or electronic controlled optics, lenses, lasers, is contemplated that using processors and/or controllers, hardware and software drivers sensors, within the display that can be at least one of pre-set by the manufacturer, controlled by the user, or controlled by information received by the device having the display with red and/or IR wavelength emission.

It would further be advantageous to have first and second devices in communication with each other to provide information to at least one of the device displays to enable the device to activate when red and/or IR wavelengths should be emitted from a display towards the eye of a person looking at the display or towards the temple of a person's head. The first device may be a portable telecommunications device and the second device may be a computer, sensor, clock, timer, wearable device including but not limited to wearables that sync to another electronic device and or wearables that provide biofeedback and/or bio-resonance information and can transmit such information to a device using wireless and/or wired communications.

It would further be advantageous to use the light emitting devices and/or pixels used to provide display image lighting, as light sources that also provide red and/or IR wavelength emission to a viewer's eyes.

It would further be advantageous to design a circuits, devices and lighting systems that use LEDs, OLEDs, laser, halogen, xenon, mercury vapor, or any other lighting technology that can be used to produce and/or emit the desired wavelengths needed to achieve the objections of the inventions described herein.

It would further be advantageous to provide a light bulb, luminaire, light fixture and/or ceiling light that includes at least one of a UV and an IR light emitter.

It would further be advantageous to combine the use of any of the light and/or wavelength emitting devices described herein in conjunction with photoreactive pharmaceuticals when delivering the AILR emissions into or onto a living species.

It would further be advantageous to provide a device that is configured to provide at least two, or more, wavelength ranges of electromagnetic emission and two or more distinctly configured spatial delivery functions. By combining these functions, the device could provide enhanced utility to person's within a space that exceeds those provided by conventional lighting or other single purpose conventional electromagnetic emission devices such as luminaires. Embodiments of such devices according to the invention can further combine the delivery of three or more distinct electromagnetic wavelength ranges within the human visible and non-visible spectrum to support both human visual needs and other needs within a space including but not limited to providing treatment for health and wellness and/or personal space heating by emitting visible light for visual reasons and providing other visible and/or non-visible wavelengths of electromagnetic energy such as near-UV, red, NIR, MIR, and/or FIR for treatment of health conditions and/or benefits as well as optionally providing personal space heating using targeting and/or focused FIR energy directed to a person and/or the personal space of a person(s).

One example embodiment of a device according to the invention may be designed to at least provide visible light in the wavelength region of 380 nanometers to about 700 nanometers for illumination which may be divided further into providing an overall ambient illumination function and a directed task function or other special purpose lighting function including, but not limited to anti-bacterial and/or anti-infective lighting, circadian entrainment and/or therapeutic lighting including but not limited to red light therapy and/or photobiomodulation. The light sources used for visible light could advantageously have different levels of emitting etendue that will match to the spatial optical and distribution patterns needed for their end purpose. For example, the overall ambient illumination may be provided by distributed light sources or arrays of light sources that have a much higher etendue such that they are easily adapted to being directed in a wider distribution and to provide the general illumination. For task, therapeutic and/or other special purpose lighting, the electromagnetic emission sources would ideally have a lower etendue, or alternatively, a higher concentration of light at their source such that they can be used efficiently with optical systems to precisely direct the light to suit the task or specific purpose, either statically or dynamically.

Dynamic changes to this light could, for example, be controlled and directed actively by inputs from sensors, occupant location data or wearable devices including wearable displays and/or wearable devices that provide biofeedback information of a person to such devices. Control systems can be coupled to active arrays of electromagnetic emitting devices with high-speed device switching and adaptive optics such as liquid crystal lenses, metamaterial devices or DMD (digital micromirror device) systems or other active optical apparatus designed to tailor light in response to occupant location, orientation, or the timing of specific tasks being performed. Directed task illumination ideally uses light sources with lower etendue such that they utilize compact optics for more precise light delivery applications such as spotlights or high gradient so called key lighting or tailored lighting. In contrast, ambient illumination in a space will typically be provided by higher etendue light sources such as linear or areal arrays of emitters since the concentration of light for optical control is usually not as important for wider dispersion lighting applications that provide ambient light within a space. An important consideration related to these dynamic changes is that the overall effectiveness of the lighting and other functions provided can be optimized for the space and the occupants such that the overall efficiency of the system will be enhanced and save energy.

The wavelengths of visible light emitted by the device could also be tunable in relative output and/or energy emission levels at different wavelengths such that it could be biologically active and selected by the control system for assisting with therapeutic light therapy, circadian entrainment or other visible light biological needs. For example, illumination wavelengths of light coming from elements of the lighting system that are directed correctly can affect the intrinsically photosensitive retinal ganglion cells ("ipRGC") of the eye to help with human circadian functions or provide photobiomodulation ("PBM") treatments. For a seated individual, this is usually characterized as being received from a zone above the horizon upwards so that it typically needs to enter the eye from a higher elevation. The device is also capable of emitting and directing red, NIR, and/or IR radiation in the space at different levels of intensity for different wavelengths at different durations of time and/or times of day. The preferred wavelength ranges could include a source of radiation that is in the red to near-infrared range such as from 630 nm to about 1300 nm and that is suited to human physiological purposes.

Studies show that mitochondria cells follow the body's circadian rhythm and tend to be most responsive to light and/or light therapy such as PBM treatments in the morning. Some embodiments may be configured to include the ability to emit red and/or IR (NIR, MIR, and/or FIR) at specific times of day such as before 12 noon or at a more narrowed time of day such as between 6 am to 9 am, and in some cases depending on the sleep habits of a person the emissions may need to occur at completely different times of day such as after 12 noon or specifically at 6 pm to 9 pm, or even when someone is actually asleep at different levels of sleep including but not limited to in a rapid eye movement "REM" state of sleep. It is contemplated by the inventors that the emissions of such electromagnetic energy and/or wavelengths may provide further enhanced benefits to certain people by modulating and/or pulsing the energy levels and/or durations of emission in response to certain biofeedback information. One such example may be to provide a specifically controlled modulation and/or pulsing of such emissions in response to one or more of the rate of REM, blood pressure, blood oxygen levels, nitric oxide levels, sugar and/or insulin levels, temperature levels, physical position of one of more body parts of a person, or any other measurable biological information that could be provided to a device according to the invention.

Infrared sources in the infrared regions in longer wavelengths from about 3,000 nanometers to about 10,000 nanometers or even further to 18,000 nanometers in the far infrared can also be included. Certain wavelengths within this range are well suited to providing efficient radiant heating of objects and other physiological benefits to people within the space. FIG. 30B is the typical atmospheric radiation transmission curve for radiation in our atmosphere and shows clear bands or windows of transmission and other wavelengths where absorption by carbon dioxide and water are known to attenuate the transmission of radiation. Typical sources of infrared radiation that are useful are known to transmit well through the atmospheric window regions and are well suited to providing benefits at a distance without attenuation. The radiation sources for the shorter infrared wavelengths, within the near-infrared ("NIR") region, will preferably be compact sources such as light emitting diodes ("LEDs"), vertical cavity surface emitting lasers ("VCSELs"), carbon nanotubes, or other devices such as tunable silicon-based devices or plasmonic grids that are configured to emit electromagnetic radiation into these wavelength regions. These sources could also have a smaller etendue that can be conveniently directed, and potentially steered, into narrower spatial distributions that can target specific areas of the body, either passively or actively, via known optical methods with potential assistance from vision systems, or location tracking, to direct amounts and optimize timing for this range of electromagnetic radiation.

Ultraviolet radiation can also be provided by sources that are ideally in the range of about 200 nm through to about 440 nm and these wavelengths can slightly overlap within the visible region of the electromagnetic spectrum above about 390 nanometers. Light sources in this range can be used for both physiological purposes and potential disinfection and anti-infective purposes.

The selection of Far Infrared emitting materials could be relatively large planar, linear or volumetric sources with electrical conversion efficiencies into the far infrared of over 80% and where over 90% of the emission spectrum is in the far Infrared region between approximately 3000 nm and 10,000 nm, or even up to 18,000 nanometers. The types of devices used for the Far Infrared region will typically include devices such as resistive wires or fibers, planar emitting sheets or volumetric designs or other sources of far infrared radiation such as ceramics, or ceramic oxides that are known in the art and that ideally operate at high conversion efficiency and with low surface temperatures and good radiant outcoupling to the space to provide effective heat transfer. The design of such devices is such that the maximum surface temperature of the device in proximity to humans should generally be less than about 140° Fahrenheit to comply with personal safety requirements. Additionally, such devices should efficiently radiate more than 80% of their energy into the space with less than 20% of the energy lost to areas around the device where less value is obtained. Such devices can be either flat or curved and conveniently attached to walls, office dividers and/or horizontally aimed downwards from ceiling locations, or at other orientations within the space such as being suspended at some angle from the vertical or horizontal planes.

Ambient lighting can also be conveniently co-located with these devices to provide illumination for occupants. Since these devices may be relatively large, they are also well suited to providing ambient illumination since the luminance of such surfaces can be kept low enough to not introduce excessive glare or veiling luminance into the space such that they are compatible with displays and visual tasks common within office, institutional or educational settings. While these devices can be stand-alone they can also be embedded within other popular devices as described herein such as displays, monitors, televisions, furniture, dividers, ceiling sound dampeners, transportation vehicles, building materials or even artwork in the space. They can also be designed to operate separately and optimized in terms of their optical, mechanical or electrical architectures to perform as an integrated design within a single device.

Other advantages and aspects of the present invention will become apparent upon reading the following description of the drawings and detailed description of the invention.

BRIEF DESCRIPTION OF THE DRAWINGS

FIGS. 2A, 2B, and 2C show schematic views of embodiments according to the invention.

FIGS. 19A and 19B show schematic views of embodiments according to the invention.

FIG. 31A shows a schematic view of an embodiment according to the invention.

FIG. 33B shows a schematic view of an embodiment according to the invention.

DETAILED DESCRIPTION

Figure 1A:
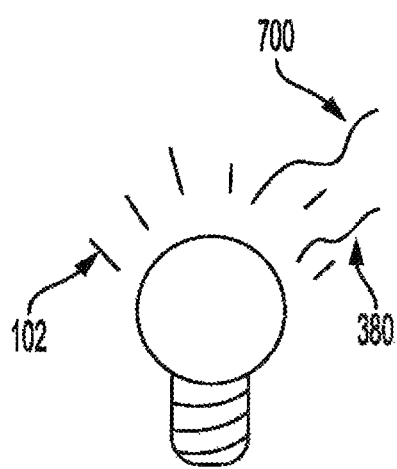
FIGS. 1A, 1B, and 1C show schematic views of embodiments according to the invention.

While this invention is susceptible to embodiments in many different forms, there is described in detail herein, various embodiments of the invention with the understanding that the present disclosures are to be considered as exemplifications of the principles of the invention and are not intended to limit the broad aspects of the invention to the embodiments illustrated.

The present invention is directed to multiple anti-infective lighting methods, devices and/or systems for eliminating infections in living species. The lighting devices and/or systems may or may not be integrated with other devices. As discussed herein, a lighting device may include any device capable of emitting light no matter the intention. Examples of lighting devices which are contemplated by this invention include, but are not limited to LEDs. OLEDs, micro-LEDs, laser diodes, incandescent, halogen, xenon, mercury vapor, fluorescent, or other light producing devices, and can potentially one das include bioluminescent living species, organisms and/or cells that could be engineered, genetically modified and/or developed to support the technologies and methods that produce the wavelength energy(s) and used in ways according to the inventions described herein. The devices and/or systems may also include one or more of power connections or leads, contacts, drivers, transistors, resistors, capacitors, inductors, diodes, integrated circuits "IC"s, antennas, fuses, sensors, feedback, firmware, software, or other devices required to provide, control and/or manage power to circuits and device in order to emit the AIRL. A lighting system may include multiple such devices, and some or all of the required parts to drive such a device or multiple devices, including but not limited to, power supplies, transformers, inverters, rectifiers, sensors or light emitting circuitry discussed herein. While a lighting device according to the invention may be incorporated into one or more of a lighting system, a lamp, a light bulb, a room, medical devices and/or non-medical devices/items including but not limited to nano-medical robots, endoscopes, bronchoscope, cameras, ventilators, electrical stimulators, implanted devices, wearable devices, full and/or partial patient enclosures, medical rooms, ceilings, walls, floors, patient beds and/or tables, chairs, prosthetics, ceiling lights, portable devices, communications devices, video displays, handheld devices, and more.

The purposes of the devices described herein are multi-fold and may be accomplished independent of each other. One intention of the methods and devices described herein is to provide anti-infective and/or antimicrobial light near and/or directly onto infectious living cells on and/or within a living species. Another intention of the methods and devices described herein is to provide IR light and/or energy(s) directly near and/or onto infectious living cells on and/or within a living species. Another intention of the methods and devices described herein is to provide antimicrobial light and IR light near and/or directly onto living cells on and/or within a living species. Another intention of the methods and devices described herein is integrated such light delivery devices into lighting systems and/or together with and/or in other devices and/or items as described in some examples herein.

In order to achieve any of the goals of the devices described herein, it may be necessary to include one or more additional medical processes and/or procedures prior to, after and/or in conjunction with the methods and/or devices according to the invention including but not limited to medications in conjunction with the operation of the devices.

Figure 1B:
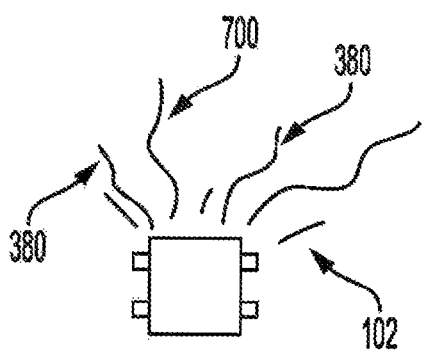
Figure 1C:
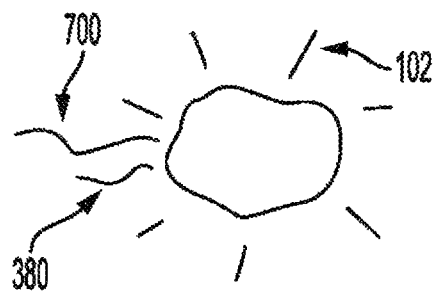

FIGS. 1A to 1C show example light sources 100 according to the invention with such example light sources including but not limited to a light bulb and/or lamp 1.A, at least one an LED 1.B, and an organic light source 1.C, the example light sources are configured to provide an output of at least one or more wavelengths 102 of one or a combination of VAICL wavelengths 380 and ICTFL wavelengths 700 (anti-infective light radiation) needed to effectively provide anti-infective lighting methods & devices and/or ("AILMD") according to the invention.

FIGS. 2A to 2C example lighting devices and/or systems 104 according to the invention. The example lighting devices and/or system in FIG. 2.a, FIG. 2.b, and FIG. 2.c provide one or a combination of output wavelengths. FIG. 2.a shows a VAICL lighting device 106 that produces at least one VAICL output wavelength(s) 108 according to the invention. FIG. 2.b. shows an ICTFL lighting device 110 that produces at least one ICTFL output wavelength(s) 112 according to the invention. FIG. 2.c shows a lighting device 114 that produces a combination of one of more VAICL output wavelength(s) 108 and ICTFL output wavelengths 112 according to the invention. One or more of any of the lighting devices and/or systems 106, 110, and/or 114, one or a combination of being an example of AILMD, may be used for eliminating infections on the exterior and/or interior of living species including but not limited to humans, animals, mammals and other living species by:

providing lighting devices, that from the exterior of a living species and/or when integrated or placed within the interior of a living species, will project sufficient levels of light and/or IR energy directly onto and/or through one or more layers of living tissue so that the light and/or IR energy reaches microbial infections, using antimicrobial lighting devices that produce one or a combination and/or group of wavelengths in the range of 350-450 nm, and more specifically 380-420 nm, and/or using red and/or infrared radiation ("IR") lighting and/or devices that produce one or a combination and/or group of wavelengths in the range of 625-1200 nm, individually using the antimicrobial lighting and/or wavelengths to increase heat onto and/or near the microbial infections, and/or simultaneously applying and/or projecting the antimicrobial lighting as a first set of electromagnetic energy wavelength(s) and the red and/or IR lighting and/or wavelength(s) as a second set of electromagnetic energy wavelength(s) that are focused onto and/or near the microbial infections within a living species to reduce and/or kill invading and/or unwanted infections and/or microorganisms on and/or within a living species.

Figure 3:
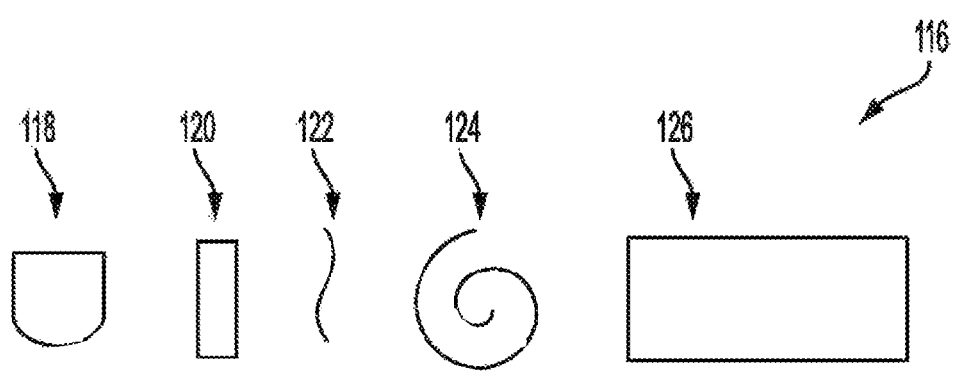
FIG. 3 shows a schematic view of an embodiment according to the invention.

FIG. 3 shows various example AILMD lighting devices and/or systems 116 according to the invention. The AILMD devices and/or systems 118, 120, 122, 124, and 126 shown depict how the various example AILMD devices and/or systems 116 may be made in different shapes and sizes or various materials including but not limited to flexible, rigid, flat, linear, tubular, completely or partially round, rectangular, stranded, flat panels, metal plastic, silicone, organic material, biodegradable material and/or other shapes, sizes and structures that can be designed as needed to deliver light at the desired wavelengths according to the design requirements of the AILMD devices and/or systems.

Figure 4:
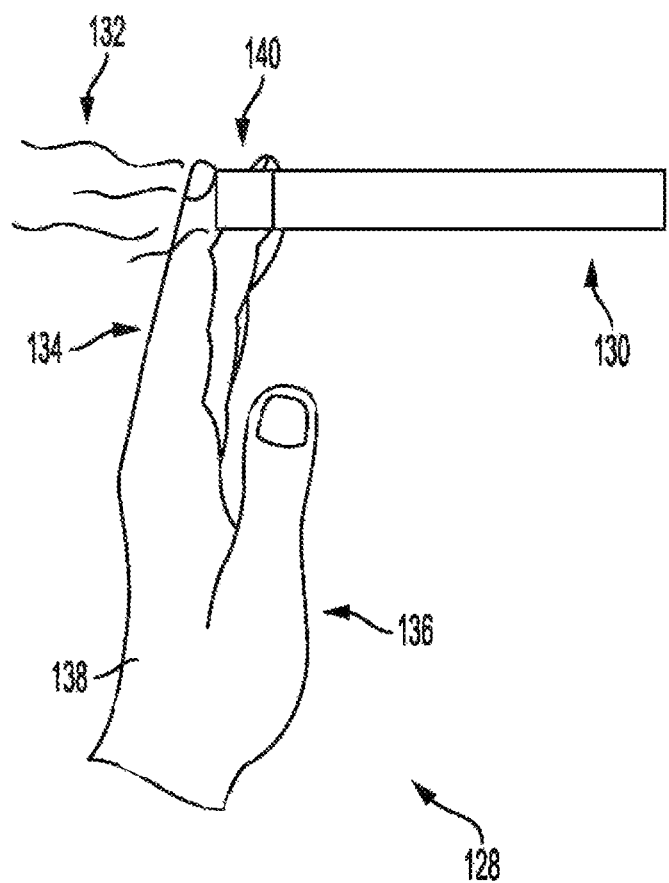
FIG. 4 shows a schematic view of an embodiment according to the invention.

FIG. 4 shows an example image 128 of how VAICL, ICTFL, and/or AILMD lighting devices and/or systems could work on a living species according to the invention. At certain levels of power and/or brightness, electromagnetic energy wavelengths (anti-infective lighting) can pass through living species and/or living species tissue. Many living species and/or one or more layers of living species tissue can be translucent. In this example a flashlight 130 is shown projecting waveforms 132 of light through a living species and/or finger 134 of a human hand 136. It is known that if you take a light sources such as a flashlight 130 and press firmly enough into a finger 134 or other areas of living tissue 138 on a living species while pointing the output wavelengths 132 of light into one side of a finger 134 or other living tissue 138, the wavelengths 132 of light energy will pass through one or more layers of the finger 134 and/or other living tissue 138.

Figure 5:
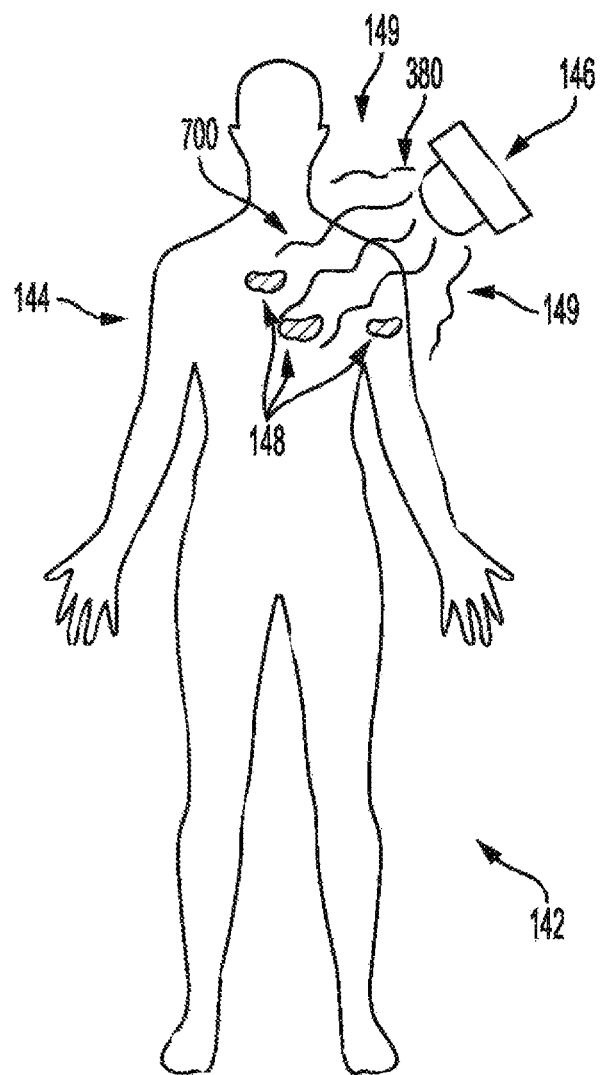
FIG. 5 shows a schematic view of an embodiment according to the invention.

FIG. 5 shows an example image 142 of human and/or living species 144 and an AILMD lighting device and/or system 146 being placed and operating from the exterior of the living species 144 to reduce and/or eliminate unwanted infectious organisms 148 on and/or within the living species 144 by radiating one or more wavelengths 149 onto, into and/or through the tissue of the living species, according to an embodiment of the present disclosure. The AILMD lighting device and/or system 146 may provide one of more output wavelengths of energy(s) of at least one or more wavelengths 149 of one or a combination of VAICL wavelengths 380 and/or ICTFL wavelengths 700 needed to effectively provide anti-infective lighting methods & devices ("AILMD") 146 according to the invention. By providing sufficient levels of output wavelength energy, the wavelengths 149 would be delivered directly onto and/or through one or more layers of living tissue so that the electromagnetic wavelength energy(s) reach near or directly onto unwanted infectious living cells similar to radiation therapy when used on cancer yet substantially safer for living cells surrounding the infectious cells 148. It is contemplated that the AILMD wavelengths 149 could be set and/or tuned at one or more specific selected wavelengths 380 and/or 700 for example, that fall within the range of 350 nm-450 nm and/or 700 nm-1400 nm based on the infection, information, feedback data and/or response of the infectious cells, amount and/or depth of tissue needing to be penetrated, or other factors. The tuning of the AILMD output wavelengths 149 could be done manually and/or automatically according to the invention and the setting and/or tuning of such wavelengths 149 could be at one or more similar or different levels of output energy levels per output wavelength. One or more wavelengths could also be set to be delivered and/or output energy from the AILMD devices in various ways including but not limited to a constant, pulsed, pulse width modulated, modulated, timed and that such outputs could be controlled, set and/or programmed by the user of the AILMD devices and/or systems 146.

Figure 6:
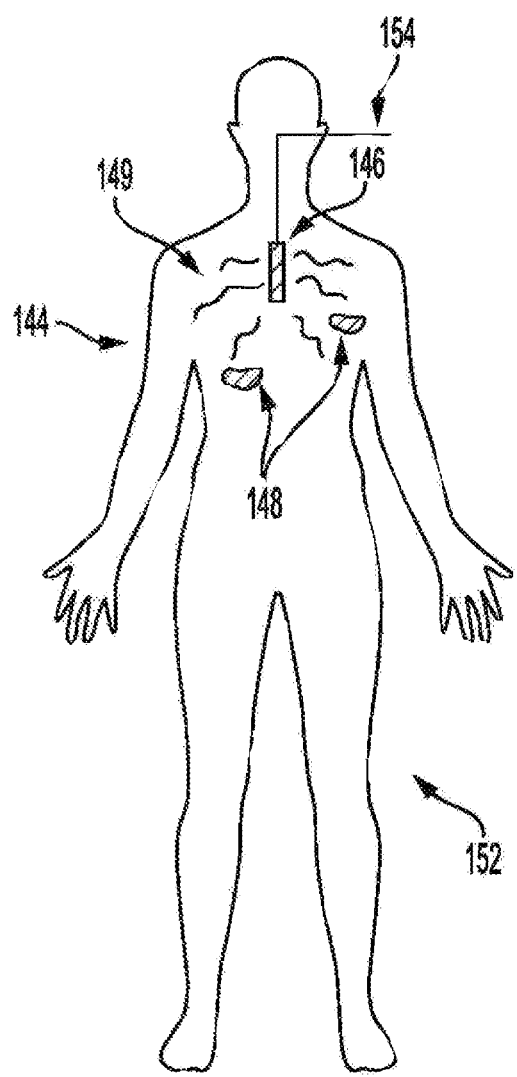
FIG. 6 shows a schematic view of an embodiment according to the invention.

FIG. 6 shows an example image 152 of human and/or living species 144 and an AILMD lighting device and/or system 146 being placed and operating from the interior of the living species 144 to reduce and/or eliminate unwanted infectious organisms 148 on and/or within the living species 144 by radiating one or more wavelengths 149 onto, into and/or through the tissue of the living species, according to an embodiment of the present disclosure. The AILMD lighting device and/or system 146 may provide one of more output wavelengths of energy(s) of at least one or more wavelengths 149 of one or as described in FIG. 5, a combination of VAICL wavelengths 380 and/or ICTFL wavelengths 700 needed to effectively provide anti-infective lighting methods & devices ("AILMD") 146 according to the invention. By providing sufficient levels of output wavelength energy, the wavelengths 149 would be delivered directly onto and/or through one or more layers of living tissue so that the electromagnetic wavelength energy(s) reach near or directly onto unwanted infectious living cells similar to existing radiation therapies used in cancer treatment however using electromagnetic radiation in the visible spectrum of wavelengths in the range of 380-450 nm and/or IR wavelengths in the range of 700-1200 nm is substantially different and safer for living species and or living cells surrounding the infectious cells 148 one would wish to eliminate. It is contemplated that the AILMD wavelengths 149 could be set and/or tuned at one or more specific selected wavelengths 380 and/or 700 for example as described in FIG. 5 that fall within the range of 350 nm-450 nm and/or 700 nm-1400 nm based on the infection, information, feedback data and/or response of the infectious cells, amount and/or depth of tissue needing to be penetrated, or other factors. The tuning of the AILMD output wavelengths 149 could be done manually and/or automatically according to the invention and the setting and/or tuning of such wavelengths 149 could be at one or more similar or different levels of output energy levels per output wavelength. One or more wavelengths could also be set to be delivered and/or output energy from the AILMD devices in various ways including but not limited to a constant, pulsed, pulse width modulated, modulated, timed and that such outputs could be controlled, set and/or programmed by the user of the AILMD devices and/or systems 146. The AILMD devices and/or systems 146 could include and/or be connected to at least one or a combination of a wire, hose, tube, fiber optic cable and/or antenna for example, such examples collectively shown in 154 and 154 could be accessible from the interior and/or exterior of the living species 144.

Figure 7:
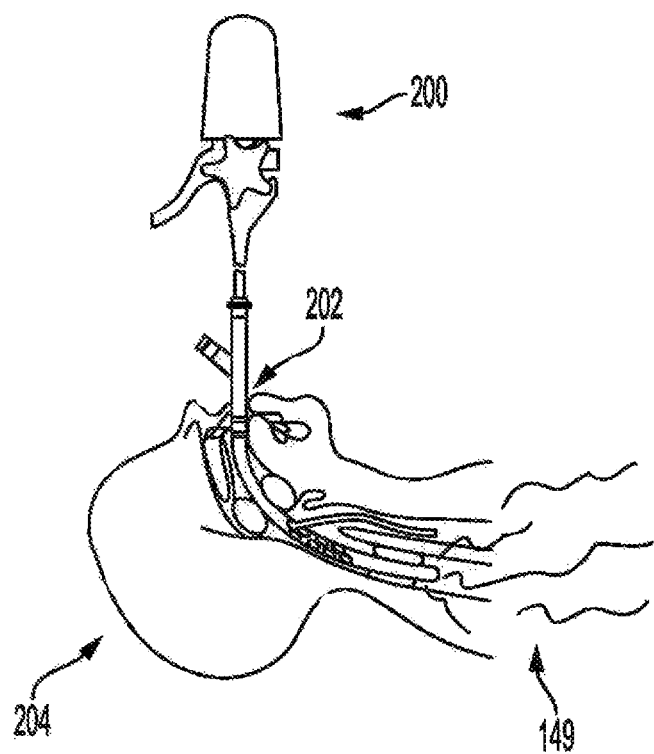
FIG. 7 shows a schematic view of an embodiment according to the invention.

FIG. 7 shows an example AILMD lighting device and/or system 200 inserted through and into the mouth of a living species 204, according to an embodiment of the present disclosure. The AILMD device 200 can have a light source 100 as described in FIGS. 1A to 1C as part of AILMD device 200. The AILMD device 200 may be integrated with other devices including but not limited to a bronchoscope, a respirator and other devices. The devices could include a light emitting section and/or material 204 that emits and/or radiates one or a combination of wavelengths 149 inside a living species as described above in FIG. 6.

Figure 8:
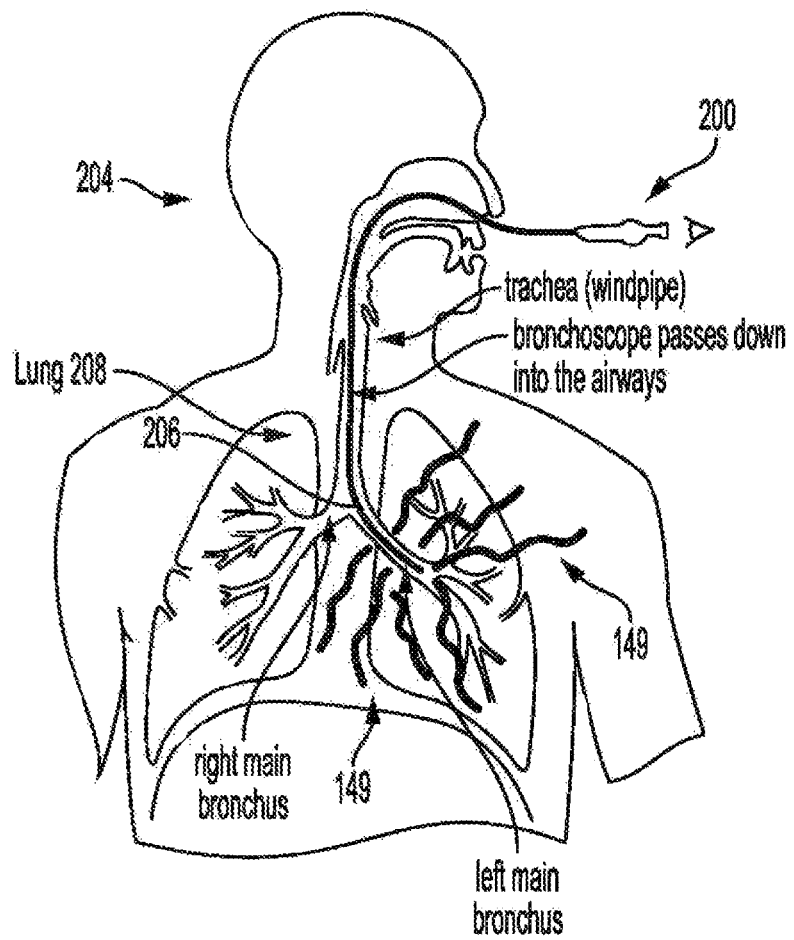
FIG. 8 shows a schematic view of an embodiment according to the invention.

FIG. 8 shows an example AILMD lighting device and/or system 200 inserted through and/or into a living species 204 according to the invention. The AILMD device 200 includes a light emitting section and/or material 206 that is placed near and/or into the lungs and emits and/or radiates one or a combination of wavelengths 149 inside a living species as described above in FIG. 6. In this example, a device such as a bronchoscope could include the ability to deliver AILMD wavelength 149 radiation directly inside of a living species lungs 208 that may be infected with a life threatening infectious disease such as Influenza, Covid-19 or other infectious diseases that could be reduced and/or killed using the AILMD devices and/or systems as described herein according to the invention.

Figure 9:
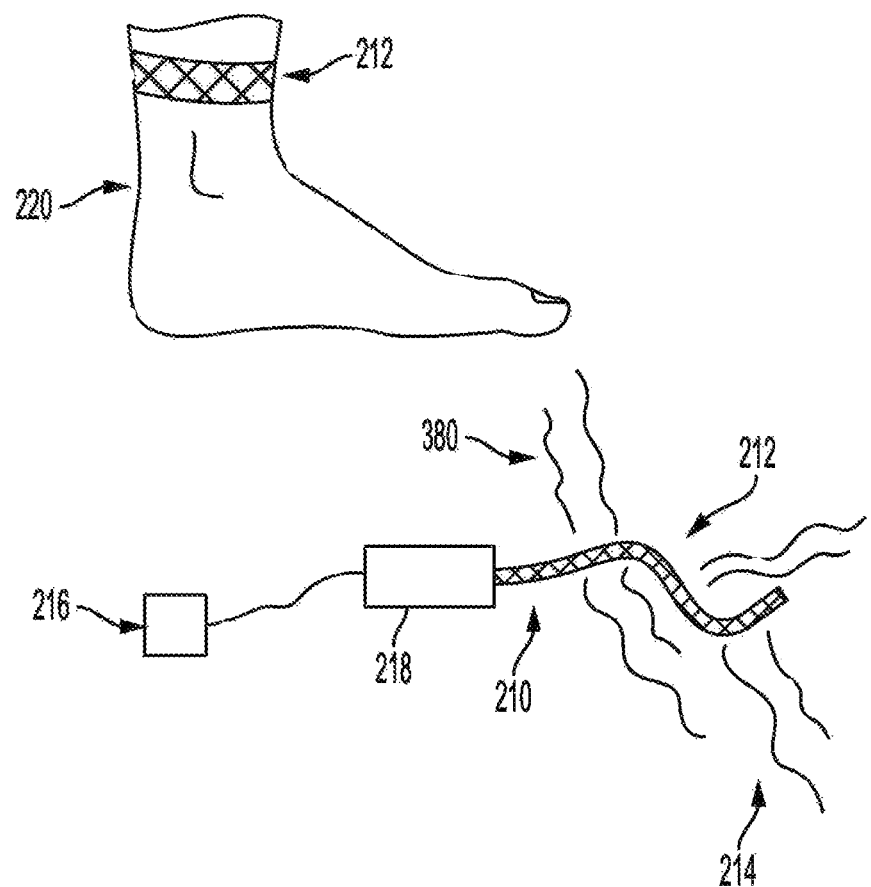
FIG. 9 shows a schematic view of an embodiment according to the invention.

FIG. 9 shows one example embodiment image of an AILMD lighting device and/or system 210 wherein the AILMD device 210 may have a flexible section 212 that provides output of one of more wavelengths of energy(s) of at least one or more wavelengths 214 of one or a combination of VAICL wavelengths 380 and/or ICTFL wavelengths 700 needed to effectively provide anti-infective lighting radiation methods & devices ("AILRMD") 210 according to the invention. The AILRMD device 210 may have a remote power supply and/or source 216 or an integral power supply and/or source 218. The power supply and/or source may be any form of power supply and/or source that can power electronic devices. The AILRMD device may be placed on and/or wrapped directly onto a body part such as a limb 220 of a human and/or living species to deliver anti-infective light radiation near and/or directly onto the infectious organisms which can be delivered onto and/or through one or more layers of living tissue so that the electromagnetic wavelength energy(s) reaches near or directly onto unwanted infectious living cells. It is also contemplated that many other types of wearables can be designed as AIRLMD devices and/or systems including but not limited to hats, helmets, wraps and/or pads, vests jackets and/or boots.

Figure 10:
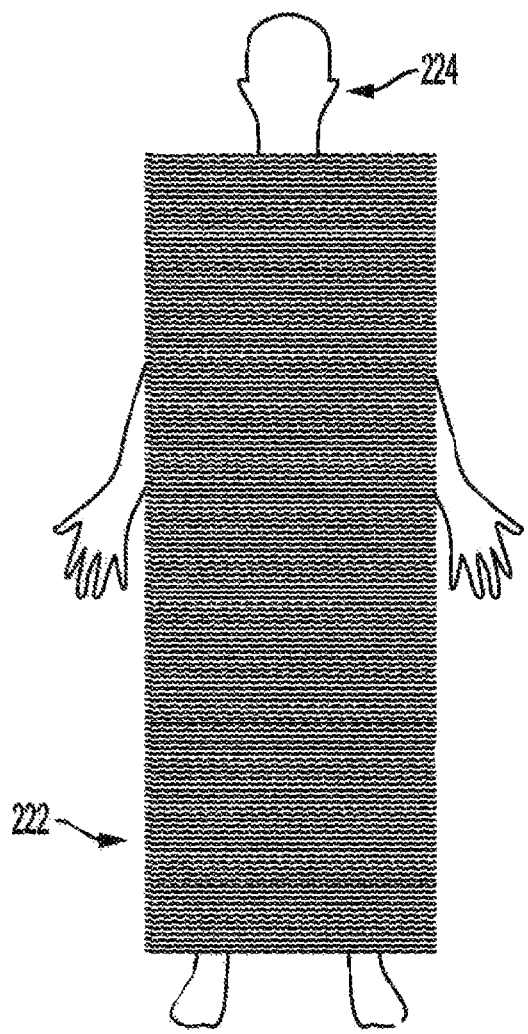
FIG. 10 shows a schematic view of an embodiment according to the invention.

FIG. 10 shows one example embodiment image of an AILRMD lighting device and/or system 222 wherein a living species 224 may be completely or partially covered and/or enclosed within an AILMD device 222 and receive treatments using anti-infective lighting radiation methods & devices ("AILRMD") according to the invention.

Figure 11:
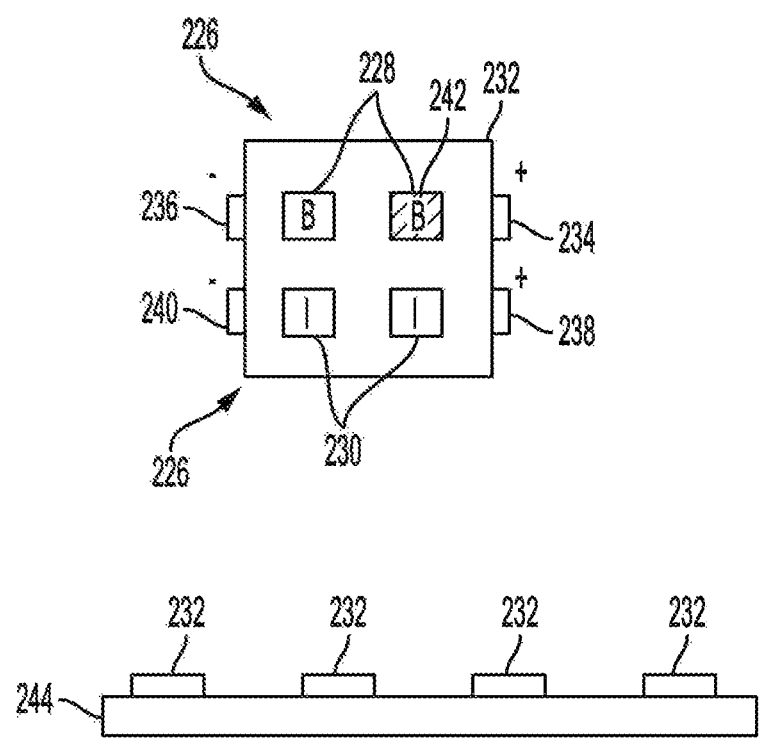
FIG. 11 shows a schematic view of an embodiment according to the invention.

FIG. 11 shows one example embodiment image of an anti-infective lighting device ("AILD") 226 for use in AILRMD devices and/or systems as described above in previous figures according to the invention. In this example, the AILD 226 is combines at least one 380-420 nm blue LED chip 228 (as an optional light source technology) and at least one 700 nm to 1 mm IR LED chip 230 into a single blue/IR LED package ("BIR") LED package 232. The BIR LED package 232 may include input and output and/or positive 234 and negative 236 "+/−" electrical connections to deliver voltage and/or current to both of the LED chips at the same time, or alternately may have separate positive 238 and negative 240 electrical connections individually to each of the blue LED chip(s) 228 and IR LED chip(s) 230 allowing for different voltage and/or current levels to be delivered to the blue and IR LEDs chips in the single package. The LED chips may be connected in series, parallel and/or series/parallel within the BIR LED package 232. When more than one blue LED chip 228 is packaged and/or more than one IR LED chip 230 is packaged in a single BIR LED package, the blue output wavelengths may be one or more different wavelengths (405 nm and 410 nm for example), and the IR LED chips may be one or more different wavelengths (750 nm, 800 nm and 850 nm for example). In addition to having the option of delivering different voltage and/or current levels to the different LED chips, different drive methods could be used for a single package. For example, the blue LED chips 228 could be powered with a constant voltage or constant current, while the IR LED chips 230 in the same package could be powered with the same/or different voltage or current level, be pulsed on and off, or be pulsed at higher currents for a given period of time compared to the blue. Various drivers and/or power supplies as well as drive schemes could be used to drive such BIR LED packages including but not limited to constant voltage, constant current, PWM, high frequency AC, high voltage AC or high voltage rectified AC, linear step drive, buck boost, or other LED driver and/or methods known to those skilled in the art. One or more of the blue LED chips 228 inside the BIR LED package 232 may or may not be surrounded and/or coated with a phosphor 242 and more than one BIR LED package 232 may be integrated into a single assembly 244 which may be a printed circuit board "PCB" material or other substrate and/or receptacle that can house the specific light source technology being used to create the AILRMD devices and/or systems.

Figure 12:
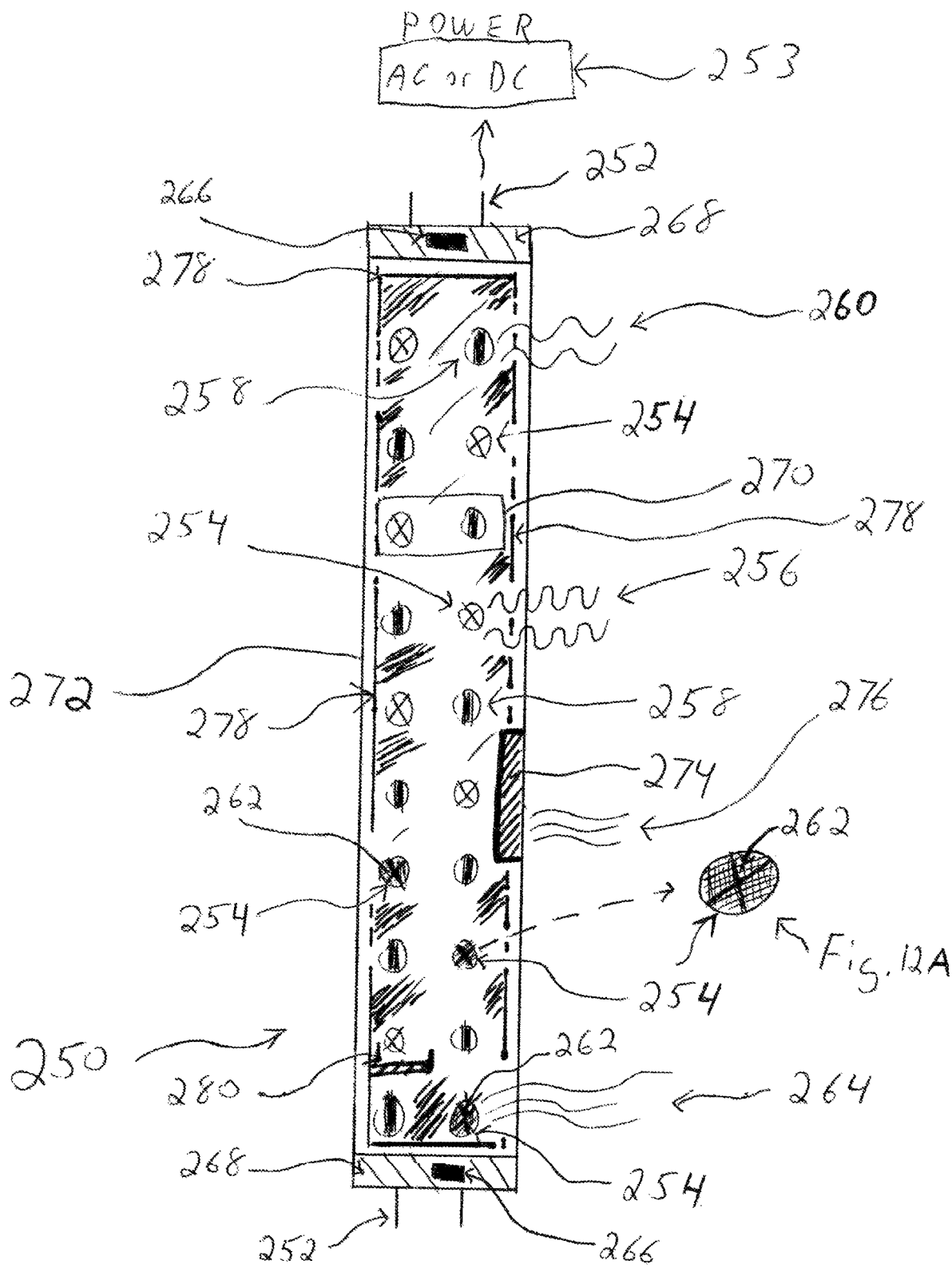
FIG. 12 shows a schematic view of an embodiment according to the invention.

FIG. 12 shows another embodiment of the invention that describes one example lighting device 250 according to the invention, and for this FIG. 12 example the lighting device 250 has a structure similar to a fluorescent tube or LED tube light bulb that is electrically and mechanically configured to be installed into a new light fixture or be used as a direct replacement for such an existing light bulb within an existing light fixture. The lighting device 250 is configured to comprise at least one electrical connector 252 for connecting the lighting device 250 to at least one or a combination of an AC or DC power source 253 which may be at least one of an AC mains voltage power source, a low voltage AC power source or a DC voltage power source distributed throughout at least a portion of a home, a building or a transportation vehicle and in this light bulb example, it would be connected to an electrical socket that is part of a new or existing light fixture which is not shown. The lighting device 250 also includes at least one or a combination of at least one VAIL source 254 configured to provide an output of at least one or more VAIL wavelengths 256 and at least one IFL source 258 configured to provide an output of at least one or more IFL wavelengths 260 thereby providing a lighting device 250 such as the example light bulb, that emits a combination of VAIL (UV and/or near-UV light) and IFL (infrared wavelengths) wavelengths simultaneously, at different times and/or or at different durations of time from a single lighting device 250. The VAIL source 254 may comprise a wavelength convertor 262 as shown in FIG. 12 and FIG. 12A, such as a phosphor or other wavelength conversion material for coating, covering and/or impregnating a portion or the entire VAIL source 254 so that the output wavelength 256 produced by the VAIL source 254 causes the VAIL source 254 to emit a converted wavelength 264 of white light that is perceived as a white color temperature of light by the human eye and measurable in Kelvin as white light by a person of ordinary skill in the art. The lighting device 250 may include integrated power supply and/or light source driver circuitry and components 266 integrated within it, such as within the end caps 268 or other location within the lighting device 250 such as the example light bulb shown in FIG. 12. The integrated power supply and/or light source driver circuitry and components 266 may include software and/or firmware and such circuitry or components 266 and programs may support at least one of know drive schemes for light sources such as LEDs, Lasers or OLEDs (or other light source and IR source devices described herein), for example including but not limited to constant voltage, constant current, PWM, high frequency AC, high voltage AC or high voltage rectified AC, linear step drive, buck boost, power delivered and controlled by time, or other LED, OLED and/or light source driver and/or methods known to those skilled in the art. At least one of or a combination of the VAIL light sources 254 and/or IFL light sources 258 may be integrated individually or together onto at least one or more circuit and/or light source substrates or packages 270 such as a printed circuit board material or LED packaging material known in the art. It is contemplated by the inventor that the substrate and/or package 270 may be a BIR LED package and may comprise a wavelength convertor such as a phosphor or other wavelength conversion material for coating, covering and/or impregnating a portion or the entire BIR LED package. The lighting device 250 may comprise a fixture and/or housing 272 to contain and support one or more of the VAIL and IFL light sources and other components needed for the complete assembly of the lighting device 250. The fixture and or housing may be made of one or a combination of glass, plastic, graphene, aluminum, copper, ceramic, metal, or other materials know in the art and may include one or more manufacturing processes including but not limited to molding, extruding, forming, stamping, printing, electronic assembly, robotic assembly, and other methods or processes know in the art. It is contemplated by the inventor that at least one or a combination of more than one FIR wavelength emission source 274 such as graphene, graphene heating elements, graphene pads, a graphene lens or optic over at least one more of the VAIL and/or IFL sources 254 and 258, LEDs or other devices and/or materials that can be configured to emit one or more Far-Infrared "FIR" wavelengths 276 can be combined and/or integrated within the device 250 enabling the device 250 to provide one or a combination of one or more output wavelengths in the range of UV, near-UV, near-IR, mid-IR, and/or far-IR simultaneously or at different controlled times, durations and/or energy levels. It is contemplated by the inventor that a lens or optic 278 may be included as part of the device 250 and mounted to the fixture and/or housing 272 to cover at least one of the VAIL or IFL sources 254 and/or 258 and that the lens and/or optic 278 may be made of at least one of glass, polymer, or graphene that such a graphene lens could be excited and/or powered with at least one of electrical, EMP, RF, audio signals, or photonic energy to produce an output of one or more FIR energy wavelengths. Red and/or JR light therapy can increase the number of mitochondria, and also boost their function in the cell and can be integrated into medical devices or general lighting devices along with UV and/or near UV light emitters to kill infectious diseases and/or unwanted bacteria with the UV and/or near UV as well as deliver IR wavelengths of energy to a living species to stimulate mitochondria cells to regenerate and/or increase production of ATP and provide one or more of the many other health benefits that can be achieved with UV, red, and/or IR light therapy provided to a person and/or other living species.

It is further contemplated by the inventor that a lens and/or optic 278 made of graphene may be used to cover and be placed over one or more of the output wavelengths emitted from one or more of the VAIL and/or IFL sources 254 and/or 258 in the lighting device 250 could be pulsed at a frequency rate that would excite the graphene lens and/or optic 278 covering the VAIL and/or IFL sources to cause the lens and/or optic to emit a far-IR wavelength output from the device 250 in addition to the wavelengths being emitted from the VAIL and/or IFL 254 and 258 sources in the device 250. The graphene lens and/or optic 278 may also include at least one conductor 280 that can be used to receive at least one or a combination of electrical signals, EMF or RF energy at frequencies that excite at least a portion of the lens thereby causing the lens to emit a Far-IR wavelength output from the lens. The conductor 280 may also be an antenna. It is further contemplated that the lens and/or optic 278 may be an electronic optic that may be dynamically controlled by information to adjust its beam angle of emission and/or repositioning its location of focus in response to data information received.

In another embodiment of the graphene material, it is contemplated that a graphene material including but not limited to a transparent graphene lens may be used in lenses used in eyewear and/or glasses or in wearable devices each of which may comprise a display and the lens and/or display, or the transparent graphene material may be used as a window, a window shield on a vehicle, a face shield on a helmet, the lens of goggles used for various activities including but not limited to work or sports and that such lenses could be configured to block unwanted wavelengths of light from a person's face and/or eyes while emitting specific desired IR and/or UV wavelengths of light towards a person's face and/or eyes by either powering the graphene lens or exiting the graphene lens with constant or pulsed various wavelengths of light, audio signals, electrical signals, RF signals or other energy that can be delivered to the graphene lens devices described herein.

It is further contemplated by the inventor that the output wavelengths from the lighting device 250 can be controlled in response to one or more of any combination of various sensors including but not limited to daylight sensors, human centric sensors, internal and/or external body temperature sensors, biofeedback sensors, bio-resonance sensors, motion sensors, occupancy sensors, plasma sensors, optical sensors, proximity sensors, sound and/or audio signal sensors, electrical signal sensors of a person, object or device, location sensors and other sensors, IR sensors that can sense the IR emissions of a living species.

Figure 13:
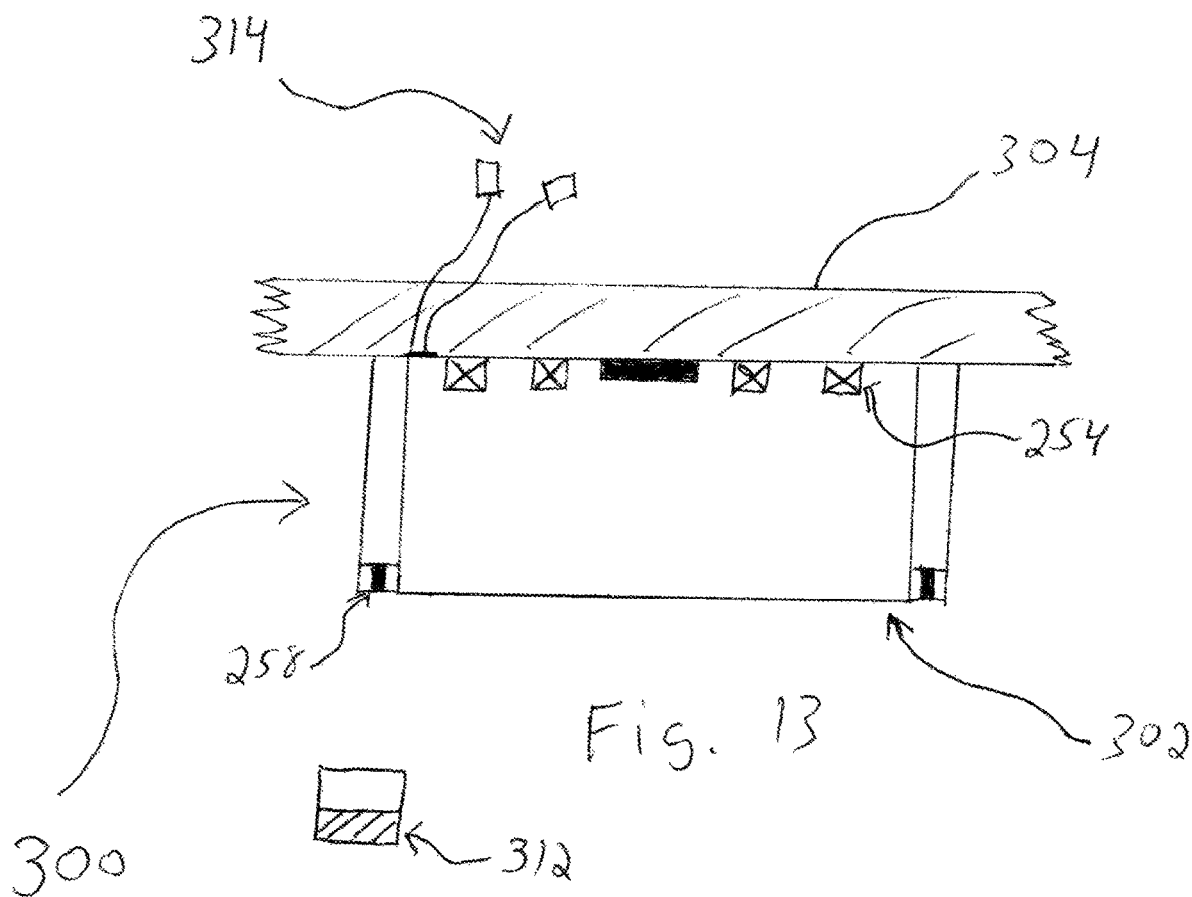
FIG. 13 shows a schematic view of an embodiment according to the invention.
Figure 13A:
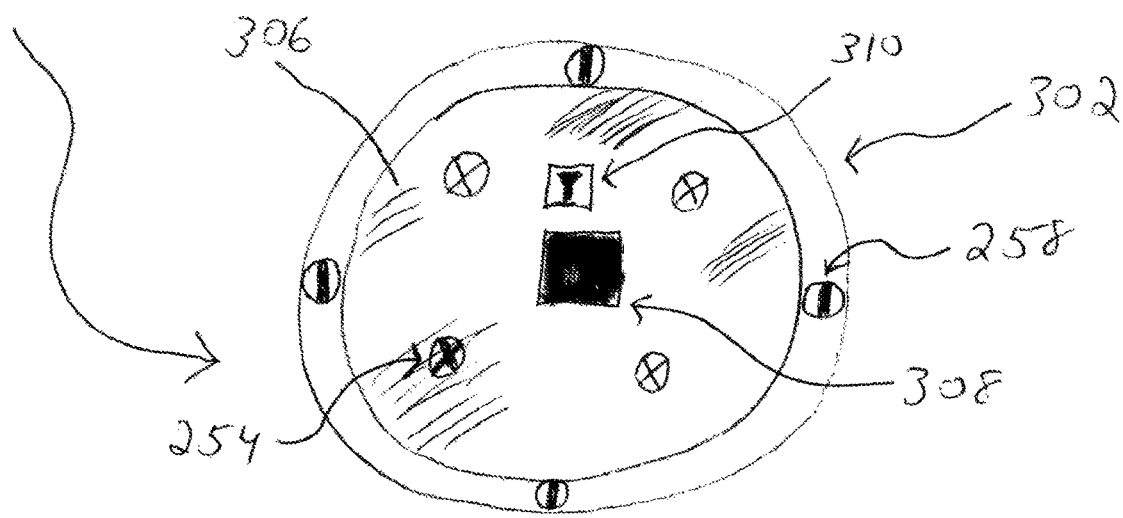
FIG. 13A shows a schematic view of an embodiment according to the invention.

FIGS. 13 and 13A. show another embodiment of the invention showing another example device 300 similar to the device 250 shown in FIG. 12 above according to the invention with device 300 having a different shape and/or mechanical structure, which in this case is an example of a ceiling light having similar components, devices and technical functionality as the device 250 described above in FIG. 12, with the exception that the device 300 has a different type and form factor of a fixture and/or housing 302. FIG. 13 is a side view of the fixture and/or housing 302 mounted to or integrated into a section of a ceiling or wall and FIG. 13A provides a view looking into the device 300 through a first lens and/or optic 306. In this example embodiment at least one of the VAIL sources 254 are covered with the lens and/or optic 306 while the IFL sources 258 may or may not be covered with the first, and/or a second optic. The lens and/or optic 306 in this example may also be made of at least one or a combination of the lens and/or optic materials as described above in FIG. 12 including but not limited to a graphene material which could be excited and or powered as described above in FIG. 12. It is contemplated that aluminum reflectors could be used to efficiently reflect and/or direct the near and/or far IFL wavelengths. The device 302 may include similar integrated power supply and/or driver electronics 308, a data communications device and/or circuit 310 configured to receive data from a wireless and/or wired network from at least one of at least one stationary and/or or portable communications and/or telecommunications device 312. The device 300 also comprises at least one set of conductors 314 configured to connect the device 300 to at least one of an AC mains voltage power source, a low voltage AC power source or a DC voltage power source distributed throughout at least a portion of a home, a building or a transportation vehicle. Red and/or IR light therapy can increase the number of mitochondria, and also boost their function in the cell and can be integrated into medical devices or general lighting devices along with UV and/or near UV light emitters to kill infectious diseases and/or unwanted bacteria with the UV and/or near-UV as well as stimulate mitochondria cells to regenerate and/or increase production of ATP with red and/or IR light.

Figure 14:
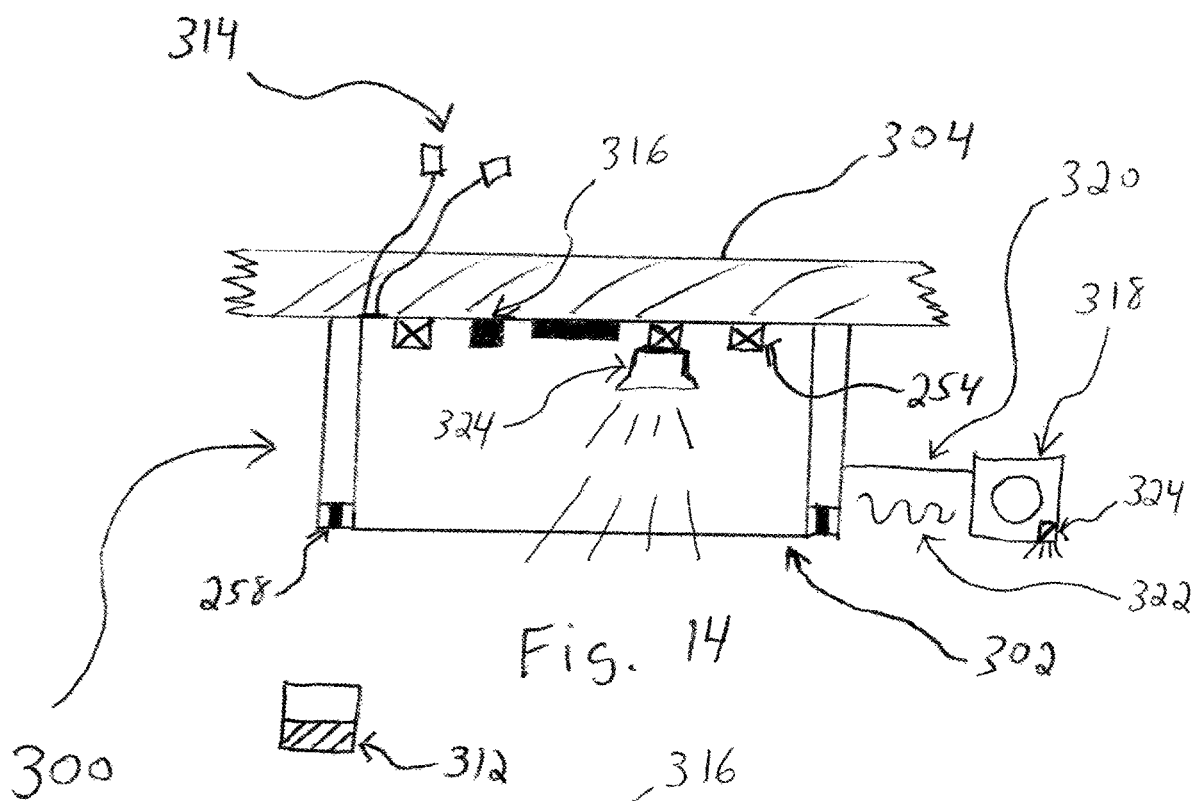
FIG. 14 shows a schematic view of an embodiment according to the invention.
Figure 14A:
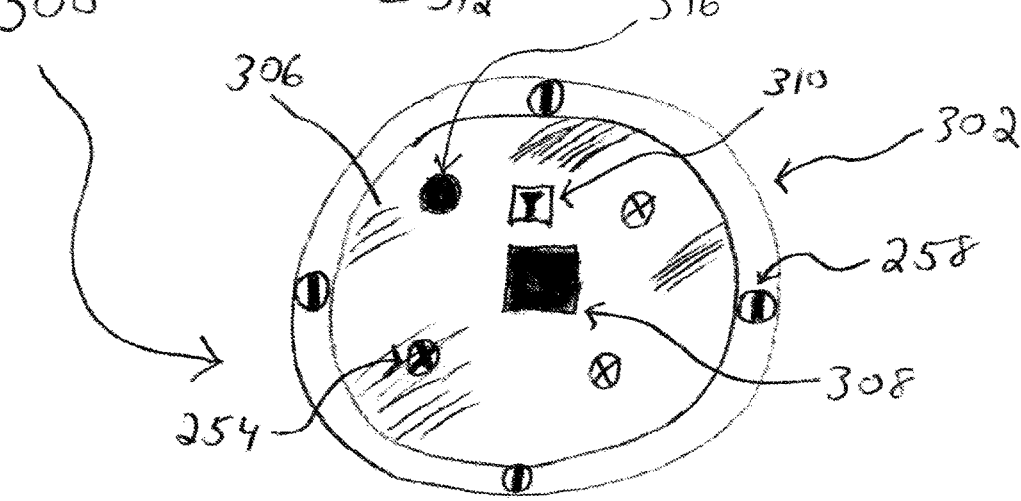
FIG. 14A shows a schematic view of an embodiment according to the invention.

FIGS. 14 and 14A shows another embodiment of the invention contemplated by the inventor that a device including but not limited to the example AILRMD's 250 and 300 described herein for providing one of more of the functions of AILRMD, VAIL and/or IFL emissions may also include conventional light sources 316 including but not limited to standard (standard meaning "not UV or near-UV" LEDs) phosphor coated LEDs and/or OLEDs integrated into a single fixture and/or housing with the VAIL and/or IFL light sources 254 and 258, and configured to provide one or more color temperatures of white light using one or more phosphor materials within a single light source for providing general lighting in a room either at the same time that the VAIL and/or IFL sources are on, or when they are not according to the invention. It is further contemplated that such a device that VAIL, IFL and general lighting with white light may utilize at least one of a controlled red/green/blue ("RGB") and or RGB-White ("RGBW") light to produce various color temperatures of white light, and such color temperatures of white light could change in color and/or color temperature throughout the day to match the daytime emission of the sun and/or the circadian rhythm of a person(s) within a room and/or building, and be on or off at various times according to a program and/or scheduling of when the lighting device emits any VAIL, IFL, FIR, or other AILR wavelengths. It is further contemplated by the inventor that such a device as described herein, including the example devices 250 and 300 as described in FIGS. 12-14A may include at least one integrated and/or external camera 318 as shown in FIG. 14 the provides signals via one of at least a cable or wireless communications to and/or from the devices 250 and/or 300. The camera 318 may also include features such as activating one or more of the VAIL, IFL, FIR, white light and/or other wavelengths in response to the camera responding to at least one integrated and/or external sensor(s) 324 that provide the camera with information regarding one or more of the occurrence, level and/or presence of at least one of motion, occupancy, temperature, light, biological data, humidity, air pressure, altitude, speed, weight, sound, or other information or other information related to a living species, an object or a location. The camera 318 may also include features such as activating an lens and/or optic 324 having one or more of the features of the lens and/or optic 278 as described in FIG. 12 and/or the lens and/or optic as described in FIGS. 13 and 13A, and or any other lens and/or optic as described herein, and also include that the lens and/or optic 324 may be an electronic optic that may be dynamically controlled by information to adjust its beam angle of emission and/or repositioning its location of focus in response to data information received which may include but not be limited to receiving data and/or information in response to the camera 318, or any other type of sensor described herein independent of the camera including but not limited to information received from a sensor regarding one or more of the occurrence, level and/or presence of at least one of motion, occupancy, temperature, light, biological data, humidity, air pressure, altitude, speed, weight, sound, or other information related to a living species, an object or a location.

Figure 15:
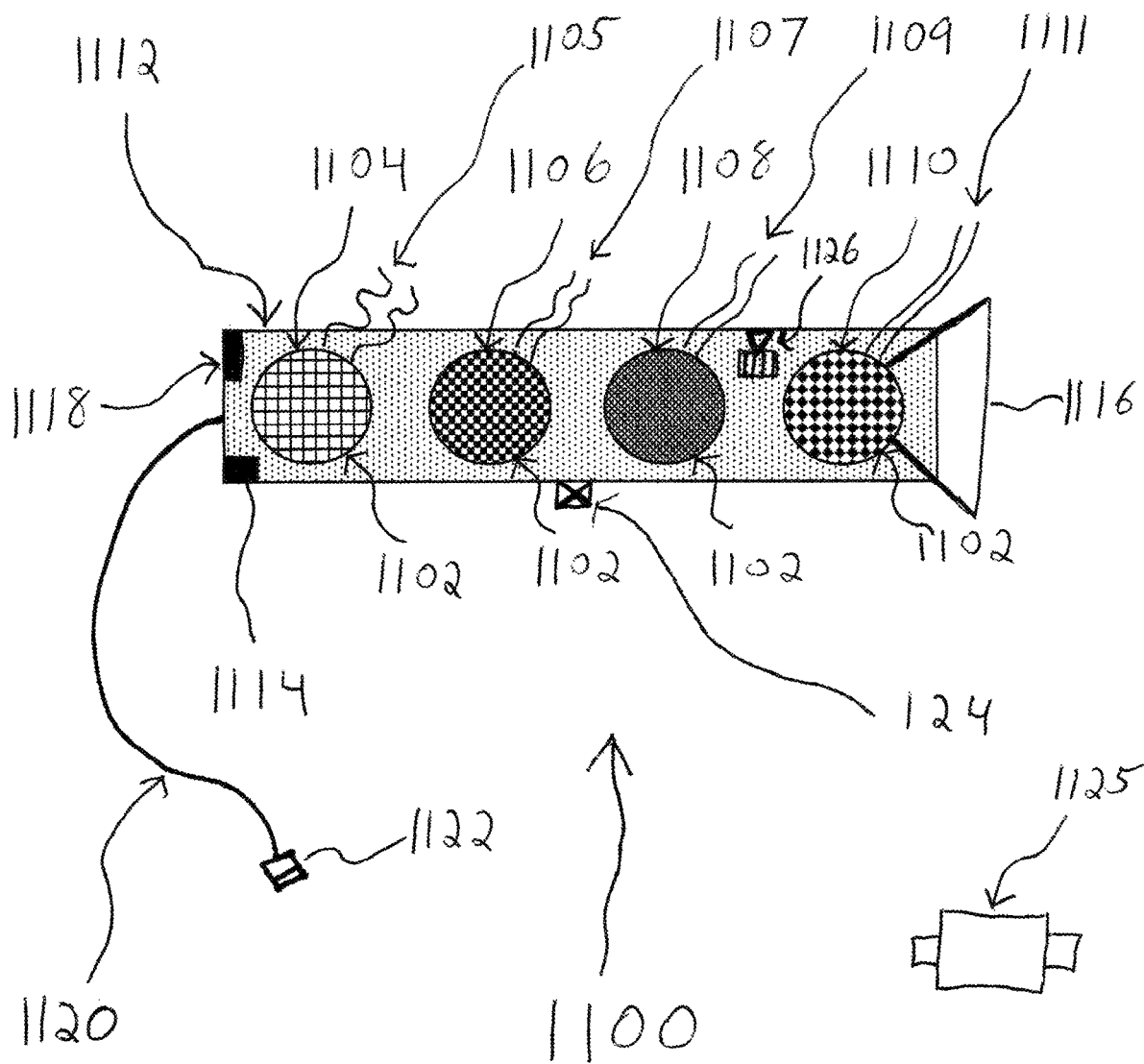
FIG. 15 shows a schematic view of an embodiment according to the invention.

FIG. 15 shows and describes an example embodiment of a device 1100 according to the invention configured to be mounted to and/or integrated into an electronic device comprising a video display that can provide power and/or data and/or control signals to the device 1100, with such example device 1100 comprising at least one light emitter 1102 configured to emit one or more wavelengths of light energy in the wavelength spectrum of visible and/or non-visible light directed toward the human eye and/or a portion of the human body and more specifically at least one or more wavelengths of light in the orange-red light spectrum of 585 nm to 620 nm, red light spectrum of 620 nm to 750 nm, and/or at least one wavelength of light within the near-infrared and/or infrared spectrum of 700 nm to 1 mm. The device 1100 may comprise at least one type or different types of light emitters 1102 and may include at least one or a combination of at least one orange/red and/or red light emitter ("RL-e") 1104 configured to emit at least one wavelength(s) of light 1105 within the range of 585 nm to 750 nm and more specifically in the range of 610 nm to 660 nm, at least one near-infrared emitter ("NIR-e") 1106 configured to emit at least one wavelength(s) 1107 within the range of 780 nm to 1400 nm and more specifically in the range of 820 nm to 860 nm which may ideally be 830 nm and/or 850 nm, at least one MID-infrared emitter ("MIR-e") 1108 configured to emit at least one wavelength(s) 1109 within the range of 1,400 nm to 3000 nm and more specifically in the range of 1050 nm to 2500 nm (and in some cases 1060 nm specifically), and/or at least one far-infrared emitter ("FIR-e") 1110 configured to emit at least one wavelength(s) 1111 within the range of 3000 nm to 1 mm and more specifically within the range of 8 to 10 microns to better match the IR emissions and absorption of the human body and or cells. The light emitters 1102 and/or 1102, 1104, 1106, 1108, and/or 1110 may be integrated as one or more subassemblies or the device 1100 may be a subassembly that is integrated into a display and/or a device comprising a display as shown in the following figures. The device 1100 may comprise a support structure 1112 that may include but not be limited to a substrate, a semiconductor backplane including but not limited to a CMOS backplane, a driver backplane, a package, an assembly or a housing configured to support and/or contain the light emitters 1102 and/or 1102, 1104, 1106, 1108, and/or 1110. The support structure may also include a material such as graphene or other material configured to emit FIR wavelengths of light. The support structure 1112 may also comprise electronic components 1114 that may include at least one or a combination of an integrated circuit ("IC"), an IC configured to emit at least one wavelength of IR energy, processor, controller, timer, wired or wireless transceiver, wired or wireless sensor(s) including but not limited to at least one biofeedback sensor, proximity sensor, motion sensor, light sensor, ambient temperature sensor and/or human body temperature sensor, software, firmware, solid state memory, battery, wireless charger and/or a camera. The device 1100 may also comprise at least one optic 1116 and/or lens which may optionally be a dynamically and/or electronic controlled optic and/or lens. At least one or more of the light emitters 1102 may be a laser. The device 1100 may also comprise a power supply and/or electronic driver circuit 1118 for selectively powering and/or controlling the power being delivered to one or more of the light emitters 1102 simultaneously or independently, and powering other integrated electronics needed for operating the device 1100. The power supply and/or electronic driver circuit 1118 may include at least one or more of a power connections or leads, electrical contacts, software drivers, transistors, current regulator, voltage regulator, timer, controller, power control circuit, resistors, capacitors, inductors, diodes, integrated circuits "IC"s, antennas, fuses, sensors, feedback circuitry, firmware, software, or other devices required to provide, control and/or manage power to circuits and device in order control the emission of one or more wavelengths of light emitted from the light emitters 1102. The device 1100 may further comprise a power input cable 1120 having a connector and/or adaptor 1122 configured to connect the device to a power source such a mains voltage source, a low voltage AC or DC power source, a battery which may be a rechargeable battery, or another device such as to an electronic device comprising an electronic video display configured to provide power and/or data through a connection port including but not limited to USB ports, lightning ports, Type C ports, Cat 5 ports or other ports known to those skilled in the art. The device 1100 may comprise a mounting bracket 1124 configured to mount the device to an electronic device comprising an electronic video display, or integrate at least one or more of the components 1102-1124 into an electronic device comprising an electronic video display. The device 1100 may utilize one or more that one of the light emitters 1102-1110 to sense the ambient temperature and/or the temperature of a person and communicate the information through an electronic video display in communication with the device 1100. The device 1100 may be in wired and/or wireless communication with another electronic device 1125 via at least one transceiver 1126 integrated in and/or connected to the device 1100, the electronic device 1125 may be connected to or worn by a person such as a smart watch and/or wearable device as known in the present day art and such electronic device may provide biofeedback data to the device 1100 from the person connected to and or wearing the electronic device 1125. The device 1100 may utilize the biofeedback data to control and or adjust one of more of the output of the wavelengths 1105, 1107, 1109 and/or 1111 in response to the data received from another electronic device 1125. It is contemplated that a portion of the device 1100 including but not limited to the support structure 1112 may comprise and or be made using infrared emitting materials such as polyvinylfluoride ("PVF"), graphene materials, IR emitting textiles, and/or other IR emitting materials. The device 1100 is configured to emit one or more of the wavelengths of red and/or IR light toward the eyes and/or body portion of a person at the same time and/or independent of the display emitting other wavelengths of light such as blue and/or white light. It is further contemplated that the device 1100 may comprise a red, green and blue (known as "RGB") light emitters that can be controlled and modulated to produce the desired wavelengths to emitted from device 1100 including but not limited to orange/red and/or red. The wavelength emissions of device 1100 may be automatically or user selectively controlled to emit and/or provide such wavelength emissions at a specific time of day (with such time of day the emission occurs being related to the location of the device within a given geographical location), period of time and/or the level of energy, brightness and/or intensity that the device 1100 emits any one or more of the wavelengths 1105, 1107, 1109, and/or 1111 of light may be controlled and/or adjusted by at least one or more of a person, electronics, software and/or sensors. It is contemplated by the inventors that one or more of the light emitters 1102 may be an LED and/or OLED configured to emit one or more wavelengths of light in the visible spectrum of light and be converted into at least any one of one wavelength of red light, IR light, and/or white light emission with quantum dots and/or nano-crystals that are either excited and/or energized with one or a combination of the adjustable visible light emission, adjustable electrical current, adjustable magnetic fields, adjustable electromagnetic fields, adjustable radio waves, adjustable static electricity, and/or adjustable audio waves. It is further contemplated that the device 1100 may comprise wireless control, audio input and output which may include a Bluetooth® speaker that emits IR wavelengths in addition to audio. It is further contemplated that the device 1100 may include artificial intelligence processors, controllers and/or software that responds to input data by a person and/or biofeedback data from a person or a device worn by a person including but not limited to wearable displays. It is further contemplated by the inventors that at least one or more of the light emitters 1102, 1104, 1106, 1108, and/or 1110 may be integrated into a wearable display including but not limited to a head wearable display for display applications near the eye including but not limited to virtual reality "VR" displays, live video displays, eyewear devices including but not limited to the eyewear devices 3701 and/or 3801 described in further detail below in FIGS. 37A through 38B, and/or augmented reality "AR" displays where blue wavelengths of light are emitted and would benefit from adding red light and/or IR light directed into the eye and/or near the temple of a person's head such that the red light and/or IR light reaches the mitochondria cells of the human body and/or eyes and optic nerves of a person including but not limited to the retina of the eye(s) thereby stimulating the cells and causing the cells to regenerate and/or produce more ATP. It is further contemplated that one, more or all of the light emitters 1102, 1104, 1106, 1108 and/or 1110 of the device 1100 can be used as an individual pixel when an embodiment of the device 1100 is integrated into an electronic visual display device and one, more or all of the light emitters 1102, 1104, 1106, 1108 and/or 1110 may be configured to be an single LED chip and/or device that is a wavelength tunable light emitter "WTLE" and/or a dynamically tunable pixel "DTP" as thought and described by recent innovators at the company named Porotech (www.porotech.com/technology/) "Porotech developed what is referred to as PoroGaN® which is a proprietary nanoporous architecture that sits between the top InGaN epi layer and the substrate of an LED chip. It acts as a buffer or strain relief layer. It is an engineered sub-surface porous layer with voids that can absorb indium atoms without expanding the crystalline structure. These voids allow indium to be added without creating the strain and defects of conventional InGaN epi wafers. As a result, bright and efficient red LEDs can finally be realized and fabricated in InGaN with industry standard LED processes and tools without any additional material treatment or complex processing steps". It is further contemplated that the device 1100 described herein comprising at least one or more light emitters may include one, more or all of the light emitters 1102, 1104, 1106, 1108 and/or 1110 to be configured to be a single PoroGan type LED chip and/or device that is a wavelength tunable light emitter ("WTLE") and/or a dynamically tunable pixel ("DTP") and may also be tuned to emit IR wavelengths of light in addition to red, green, and blue wavelengths of light and/or one or a combination of IR, Red, Green and/or Blue wavelengths of light simultaneously, or a separate light emitter configured to emit the IR wavelengths of light may be combined with a separate WTLE. Such one or more light emitters 1102 may also be configured to emit light into at least one or more of light wavelength conversion materials, devices and/or elements including but not limited to quantum dots, phosphors and/or dyes that the wavelengths of light emitted from any one of the emitters 1102, 1104, 1106, 1108 and/or 1110 may first emit into a wavelength conversion material, device and/or element, and then emit out of a the wavelength conversion material, device and/or element as different wavelengths of light (e.g. blue in and at least one or a combination of red, green, blue or any possible wavelength that can result from the combination of red, green and/or blue wavelengths out as the converted wavelengths from the blue wavelength(s)). It is also contemplated that one or more wavelengths (e.g. a blue wavelength) of light may pass through the materials, devices and/or elements including but not limited to quantum dots, phosphors and/or dyes without being converted to a new wavelength of light and combined with other wavelengths of light that are emitted from the materials, devices and/or elements including but not limited to quantum dots, phosphors and/or dyes as the wavelengths are emitted from the device 1100 or an electronic visual display device comprising one and/or more of the embodiments described herein. It is further contemplated by the inventors that the device 1100 is not limited to only utilizing and/or incorporating light emitters 1102 and may also include at least one of more of at least one additional light emitters configured to emit Green wavelengths of light in the range of 495 nm to 570 nm, Blue wavelengths of light in the range of 380 nm to 500 nm, Cyan wavelengths of light in the range of 490 nm to 520 nm and preferably in the range or 485 nm to 495 nm, UV wavelengths of light (as described herein) and/or near UV wavelengths of light (as described herein) such that the device 1100 provides visible light, non-visible light and UV wavelengths of light along with and in addition to the light and/or wavelengths emitted by any one of the light emitters 1102 and/or 1104, 1106, 1108 and/or 1110 and all the light emitters could be individually controlled according to the methods described herein. It is contemplated that a single LED chip, or multiple LED chips could produce one of more of the wavelengths of light as described herein. It is further contemplated by the inventors that the device 1100 may be integrated into a ceiling light, a light bulb or any other form of light fixture that emits one or more color temperatures of white light white light, and preferably two or more color temperatures of white light, including but not limited into a lighting device that has user selectable color temperatures of white light or user controllable and/or tunable color temperatures of white light that fall within two or more white color temperatures between the ranges of 1000 to 10,000 Kelvin with the difference between the two color temperatures of white light being at least 250 kelvin such as 2700K and 3000K, or 3500K and 4100K for example and may also include one or more light emitters configured to emit RGB wavelengths of light. The device 1100 could include these white light emitters which may be phosphor coated light emitters and integrated together with one or more or any combination of the light emitters including RGB light emitters and/or light emitters 1102 and/or 1104, 1106, 1108 and/or 1110 into a ceiling light, a light bulb or any other form of light fixture, or a display or a display with an integrated light fixture that produces white light for purposes other than display images such as task lighting or accent lighting. It if further contemplated that the device 1100 may be integrated into other devices such as a speaker, including but not limited to a portable battery operated or power supply operated wireless speaker such as a Bluetooth speaker, or a wall or ceiling mounted wired or wireless speaker and the speaker can be integrated in a lighting device or a lighting system along with the device 1100. It is also contemplated the device 1100 could be integrated into the surrounding trim of a ceiling light or a ceiling speaker where the trim often has a given angle around the perimeter and that any one of the emitters 1102 and/or 1104, 1106, 1108 and/or 1110 could be integrated in the angled section of trim within a down light, ceiling light and/or speaker having such a trim with its housing. It is further contemplated that the device 1100 may include circuitry that can turn on and off any one or more of the light emitters 1102 and/or 1104, 1106, 1108 and/or 1110 sequentially using a sequencing circuit or a LED chaser circuit and the sequencing circuit may be configured to respond to a sensor including but not limited to include any sensors described herein. It is further contemplated the device 1100 may be integrated into a light bulb, lighting and/or lighting system, or a display and include at least one indicator light to that may be illuminated and inform a person as to when non-visible wavelengths of electromagnetic energy such as IR wavelengths are being emitted by the device 1100 or a device that the device 1100 in integrated within.

Figure 16:
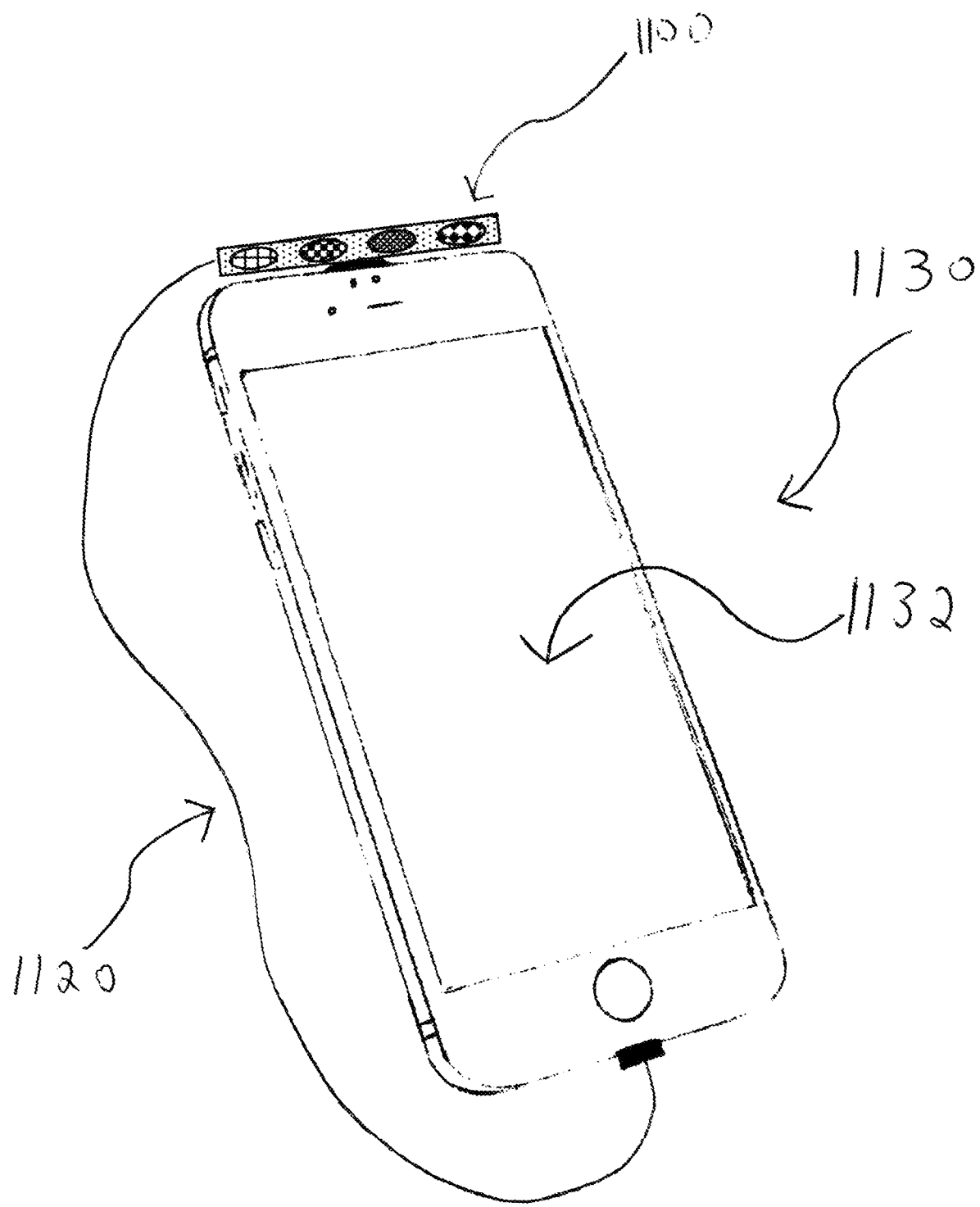
FIG. 16 shows a schematic view of an embodiment according to the invention.

FIG. 16 shows and describes another example embodiment according to the invention comprising the device 1100 as described in FIG. 15 configured to be mounted to a portable telecommunications device comprising a display 1130 that emits blue wavelengths of light directed towards the eyes of a person viewing the display. The display 1132 in the portable telecommunications device having a display 1130 emits at least one blue wavelength of light towards the eyes of a person viewing the display 1132 when the display 1132 is in use and the device 1100 is configured to emit at least one or more wavelengths of red and/or IR light towards the eyes of a person viewing the display 1132 to counteract the negative effects of the blue light emission to the eyes of a person using the display 1132. The device 1100 may be electrically connected to and may receive power and data from the portable telecommunications device 1130 and/or transmit data to the portable telecommunications device 1130 though the cable 1120. It is contemplated that the device 1100 may be in wireless communication with the portable telecommunications device 1130 and receive power and/or exchange data communications wirelessly from the portable telecommunications device 1130 and not need the cable 1120. It is further contemplated that one or more components of the device 1100 may be integrated into and part of the portable telecommunications device having a display 1130. The device 1100 may also have its own separate power source such as a battery or a power source input from a source other than the portable telecommunications device 1130.

Figure 17:
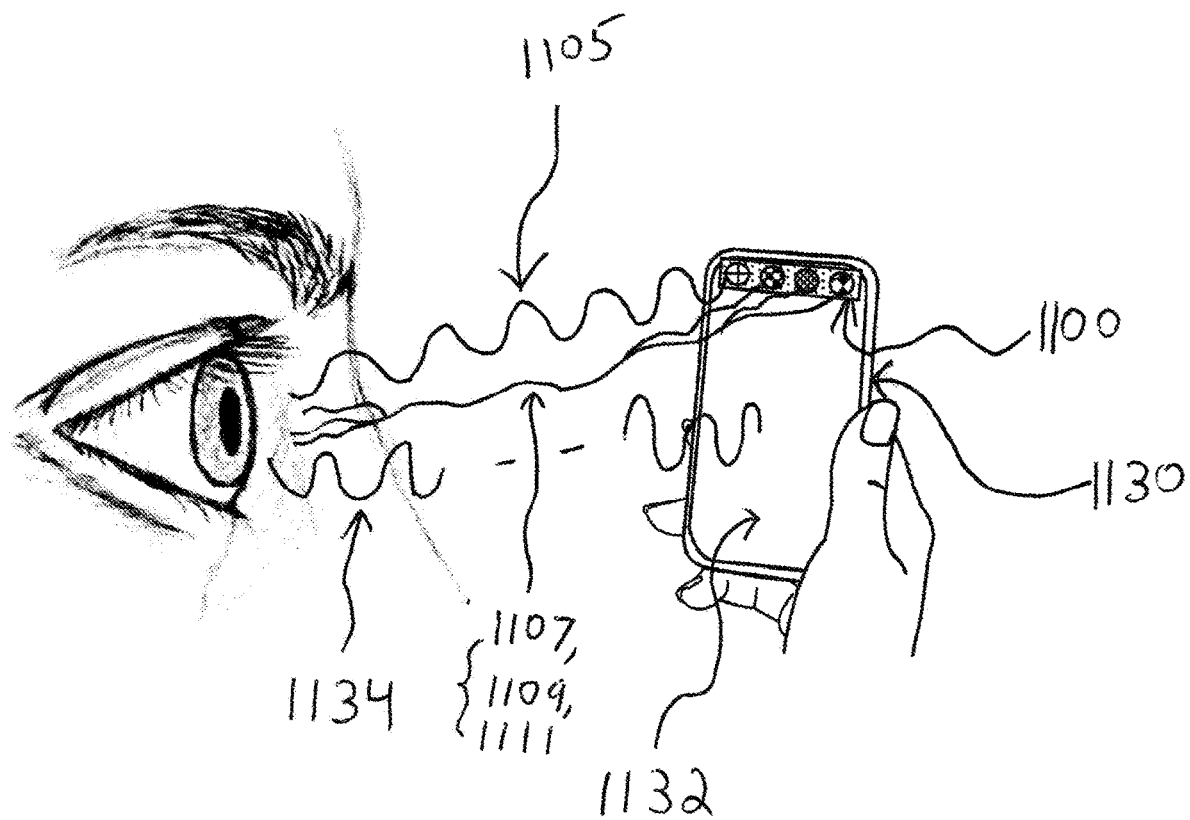
FIG. 17 shows a schematic view of a preferred embodiment according to the invention.

FIG. 17 describes another example embodiment 1130 according to the invention comprising the device 1100 as described in FIG. 15 integrated into a portable telecommunications device comprising a display 1130 that emits blue wavelengths of light from the display 1132 as described in FIG. 16. The device 1100 is an integrated part of the portable telecommunications device 1130 and configured to emit at least one or a combination of orange/red and/or red wavelengths of light 1105 within the range of 585 nm to 750 nm directed towards the eyes of a person and/or at least one or more of wavelength of light 1107, 1109, and/or 1111 within the near-infrared and/or infrared spectrum of 700 nm to 1 mm directed towards the eyes of a person using the portable telecommunications device comprising a display 1130. The device 1100 may be configured to emit one of more wavelengths of light 1105, 1107, 1109, and/or 1111 for a period of time when the person is looking at and using the display 1132 integrated within the portable telecommunications device comprising a display 1130 at the same time that the display 1132 is emitting white and/or blue wavelengths of light 1134 within the 380 nm to 500 nm light spectrum "basic display lighting" or independent of the portable telecommunications device comprising a display 1130 emitting any white and/or blue wavelengths of light 1134.

Figure 18A:
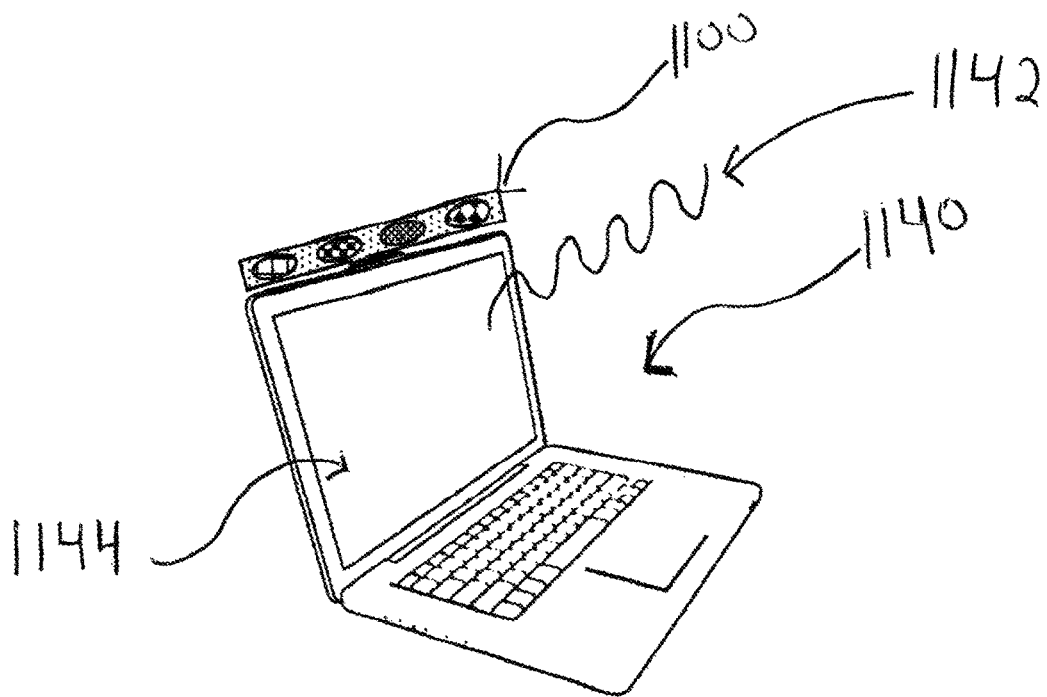
FIGS. 18A and 18B show schematic views of embodiments according to the invention.
Figure 18B:
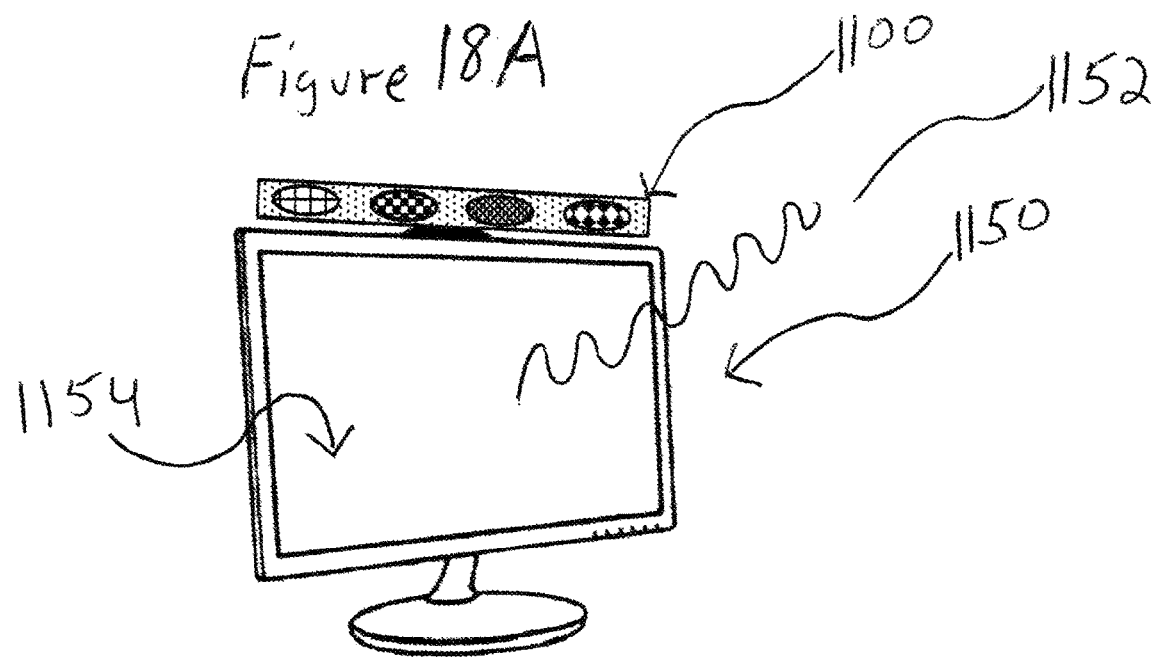

FIGS. 18A and 18B show and describe additional example embodiments according to the invention comprising the device 1100 as described in FIG. 15 and configured to mount to other example display devices 1140 (18A) and 1150 (18B) such as 18A, a personal computing device comprising a display 1140 that emits wavelengths of light 1142 within the blue light spectrum from its display 1144 directed towards the eyes of a person when the display 1144 is powered on and in use by a person, or 18B, a television comprising a display 1150 that emits wavelengths of light 1152 within the blue light spectrum from its display 1154 directed towards the eyes of a person when the display 1154 is powered on and in use by a person. The device 1100 may be connected to and receive power and data from the personal computing device comprising a display 1140 or the television comprising a display 1150 and/or transmit data received by the device 1100 to the personal computing device comprising a display 1140 or the television comprising a display 1150. It is contemplated that the device 1100 may be in wireless communication with the personal computing device comprising a display 1140 or the television comprising a display 1150 and receive power wirelessly from the display devices 1140 and 1150.

FIGS. 19A and 19B describe additional example embodiments according to the invention comprising the device 1100 as described in FIG. 15, and similarly to the example embodiment of the invention described in FIG. 17 having the device 100 integrated within a portable telecommunications device having a display 1130, the device 1100 is integrated into the example display devices 1140 (19A) and 1150 (19B) as shown in FIGS. 19A and 19B such as 19A, a personal computing device comprising a display 140 that emits wavelengths of light 1142 within the blue light spectrum from its display 1144 directed towards the eyes of a person when the display 1144 is powered on and in use by a person, or 19B, a television comprising a display 1150 that emits wavelengths of light 1152 within the blue light spectrum from its display 1154 directed towards the eyes of a person when the display 1154 is powered on and in use by a person. The integrated device 1100 may be configured to emit one of more wavelengths of light 1105, 1107, 1109 and/or 1111 when the person is looking at and using the display devices 1140 and/or 1150 at the same time that the displays 1144 and/or 1154 are emitting white and/or blue wavelengths of light 1142 and/or 1152 within the 380 nm to 500 nm light spectrum "basic display lighting" or independent of the displays 1144 and/or 1154 emitting any white and/or blue wavelengths of light 1142 and/or 1152.

Figure 20:
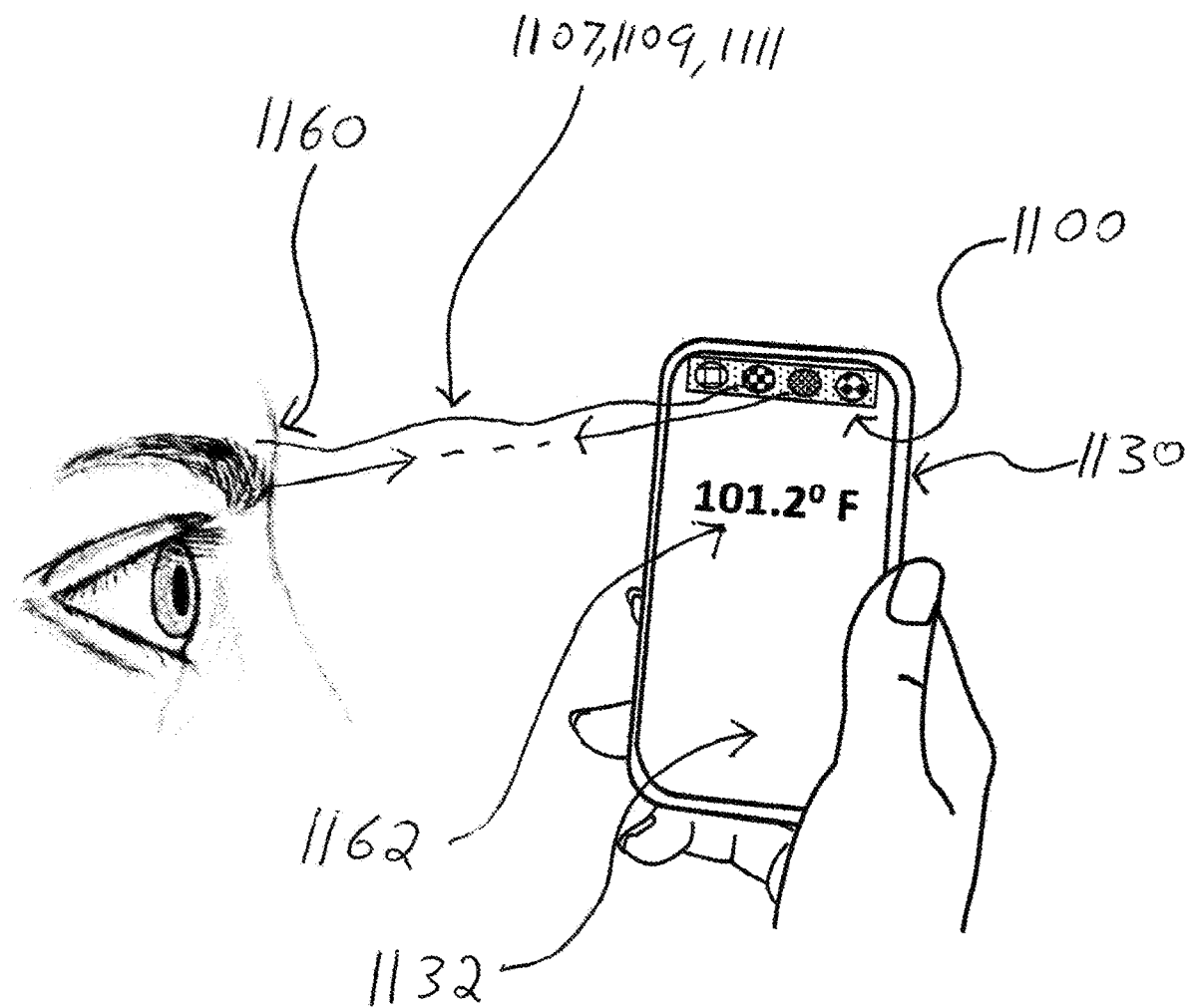
FIG. 20 shows a schematic view of an embodiment according to the invention.

FIG. 20 shows and describes another example embodiment according to the invention similar to the example embodiment of the invention described in FIG. 17 having the example embodiment of the device 1100 according to the invention described in FIG. 15 being integrated into a portable telecommunications device comprising a display 1130 as described in FIG. 17. The device 1100 integrated into the portable telecommunications device 1130 may be configured to emit at least one or a combination of wavelengths of light 1107, 1109, and/or 1111 within the near-infrared and/or infrared spectrum of 700 nm to 1 mm may be used to detect the body temperature of a person 1160 when directed towards the person 1160 using the portable telecommunications device comprising a display 1130 and the portable telecommunications device comprising a display 1130 may display the temperature reading 1162 result from the display 1132 of the portable telecommunications device comprising a display 1130.

Figure 21:
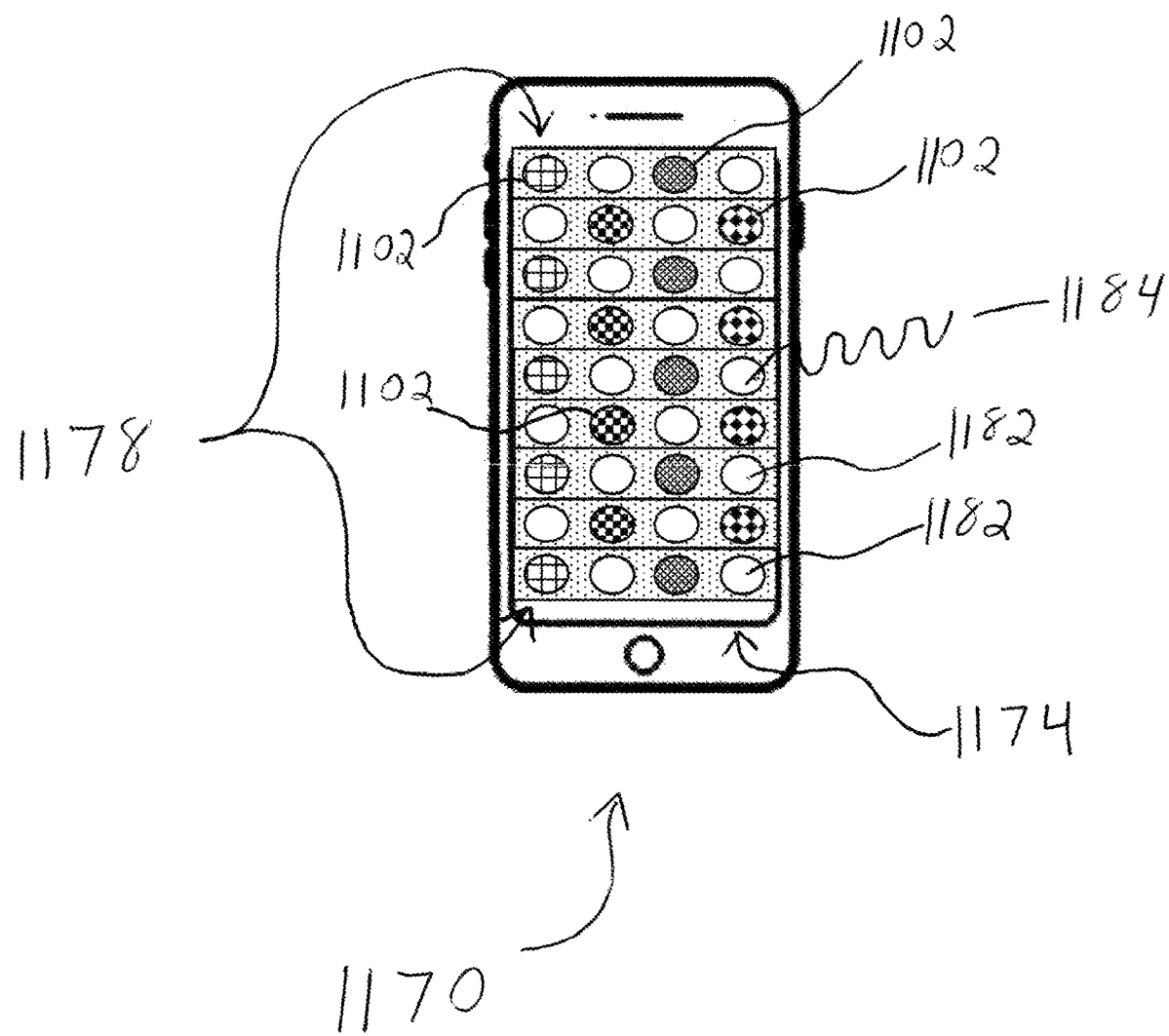
FIG. 21 shows a schematic view of an embodiment according to the invention.

FIG. 21 shows and describes another example embodiment of a device 1170 according to the invention. The device 1170 is an electronic device that comprises at least one display 1174. The display 1174 comprises a plurality of light emitters 1178. The plurality of light emitters 1178 are comprised of a plurality of light emitters 1182 configured to emit wavelengths of light 1184 used to produce video images on the display 1174 that are visible and directed towards the eyes of a person viewing the display 1174 and a plurality of light emitters 1102 as described in FIG. 15 in the device 1100 configured to emit one or more of the wavelengths of light energy in the wavelength spectrum of visible and/or non-visible light directed towards the human eye and/or a portion of the human body, and more specifically at least one or more wavelengths of light in the orange-red light spectrum of 585 nm to 620 nm, Red light spectrum of 620 nm to 700 nm, and/or at least one wavelength of light within the near-infrared and/or infrared spectrum of 700 nm to 1 mm. One or more of the light emitters 1102 may emit wavelengths of light at the same time the display 1174 is emitting wavelengths of light 1184 used to produce video images on the display 1174 or alternately when the display 1174 is not emitting wavelengths of light 1184 used to produce video images on the display 1174. It is contemplated by the inventor that the video display 1174 may be constructed in whole or in part of a plurality of light emitters 1178 that are each individually capable of producing and/or emitting at least two or more including but not limited to all of the wavelengths of light 1184 used to produce both the moving and/or still video images on the display 1174 and the wavelengths of light energy in the wavelength spectrum of visible and/or non-visible light in the orange-red light spectrum of 585 nm to 620 nm, red light spectrum of 620 nm to 700 nm, and/or at least one wavelength of light within the rear-infrared and/or infrared spectrum of 700 nm to 1 mm to provide PBM treatments. It is further contemplated that RGB LEDs, including but not limited to voltage and current tunable single chip RGB LEDs, and/or OLEDs could be used to emit the wavelengths of light 1184 used to produce both the video images on the display 1174 and at least one of the additional wavelengths of light energy in the wavelength spectrum of visible and/or non-visible light in the orange-red light spectrum of 585 nm to 620 nm, red light spectrum of 620 nm to 750 nm, and/or at least one wavelength of light within the near-infrared and/or infrared spectrum of 700 nm to 1 mm. It is further contemplated by the inventor that a circuit comprising at least one voltage and current tunable single chip ("SC-RGB") LEDs and at least one IR LED chip, or one or more individual red, green, blue and IR LED chips ("RGB-IR chip circuit") could be mounted to a circuit substrate to provide an RGB-IR LED array or the substrate may optionally be the substrate within an LED package and constructed to provide an RGB-IR LED package and that the RGB-IR LED array and/or RGB-IR LED package (either of which being an RGB-IR LED component) could be surface mounted to a circuit board substrate and/or other substrates and allow for each and/or a group of individual RGB-IR chips within the RGB-IR component to be individually controlled in power level and/or light energy emission by using various power supplies, drivers and/or drive schemes including but not limited to constant voltage, constant current, pulse width modulation ("PWM"), high frequency AC, high voltage AC or high voltage rectified AC, linear step drive, buck boost, pulsed drive, resistor/capacitor "RC" network circuit driven using frequency modulation, or other LED driver and/or drive methods known to those skilled in the art. The RGB-IR component may be used to provide the features of the device 1100 described within the various embodiments of the invention in FIGS. 15-21 described herein as well as the RGB-IR LED could be utilized as at least one pixel within an electronic device comprising at least one electronic video display.

FIG. 21 shows and describes another example embodiment of a device 1170 according to the invention. The device 1170 is an electronic device that comprises at least one display 1174. The display 1174 comprises a plurality of light emitters 1178. The plurality of light emitters 1178 are comprised of a plurality of light emitters 1182 configured to emit wavelengths of light 1184 used to produce video images on the display 1174 that are visible and directed towards the eyes of a person viewing the display 1174 and a plurality of light emitters 1102 as described in FIG. 15 in the device 1100 configured to emit one or more of the wavelengths of light energy in the wavelength spectrum of visible and/or non-visible light directed towards the human eye and/or a portion of the human body, and more specifically at least one or more wavelengths of light in the orange-red light spectrum of 585 nm to 620 nm, red light spectrum of 620 nm to 700 nm, and/or at least one wavelength of light within the near-infrared and/or infrared spectrum of 700 nm to 1 mm. One or more of the light emitter 1102 may emit wavelengths of light at the same time the display 1174 is emitting wavelengths of light 1184 used to produce video images on the display 1174 or alternately when the display 1174 is not emitting wavelengths of light 1184 used to produce video images on the display 1174. It is contemplated by the inventor that the video display 1174 may be constructed in whole or in part of a plurality of light emitters 1178 that are each individually capable of producing and/or emitting at least two or more including but not limited to all of the wavelengths of light 1184 used to produce both the video images on the display 1174 and the wavelengths of light energy in the wavelength spectrum of visible and/or non-visible light in the orange-red light spectrum of 585 nm to 620 nm, red light spectrum of 620 nm to 700 nm, and/or at least one wavelength of light within the near-infrared and/or infrared spectrum of 700 nm to 1 mm. It is further contemplated that RGB LEDs, including but not limited to voltage and current tunable single RGB LEDs, including but not limited to voltage and current tunable single chip RGB LEDs, and/or OLEDs could be used to emit the wavelengths of light 1184 used to produce both the video images on the display 1174 and at least one of the additional wavelengths of light energy in the wavelength spectrum of visible and/or non-visible light in the orange-red light spectrum of 585 nm to 620 nm, red light spectrum of 620 nm to 750 nm, and/or at least one wavelength of light within the near-infrared and/or infrared spectrum of 700 nm to 1 mm. It is further contemplated by the inventor that a circuit comprising at least one voltage and current tunable single chip ("SC-RGB" LEDs) and at least one IR LED chip, or one or more individual red, green, blue, and IR LED chips ("RGB-IR chip circuit") could be mounted to a circuit substrate to provide an RGB-IR LED array or the substrate may optionally be the substrate within an LED package and constructed to provide an RGB-IR LED package and that the RGB-IR LED array and/or RGB-IR LED package (either of which being an RGB-IR LED component) could be surface mounted to a circuit board substrate and/or other substrates and allow for each and/or a group of individual RGB-IR chips within the RGB-IR component to be individually controlled in power level and/or light energy emission by using various power supplies, drivers and/or drive schemes including but not limited to constant voltage, constant current, pulse width modulation ("PWM"), high frequency AC, high voltage AC or high voltage rectified AC, linear step drive, buck boost, pulsed drive, resistor/capacitor ("RC") network circuit driven using frequency modulation, or other LED driver and/or drive methods known to those skilled in the art. The RGB-IR component may be used to provide the features of the device 1100 described within the various embodiments of the invention in FIGS. 15-21 described herein as well as the RGB-IR LED could be utilized as at least one pixel within an electronic device comprising at least one electronic video display.

Figure 22:
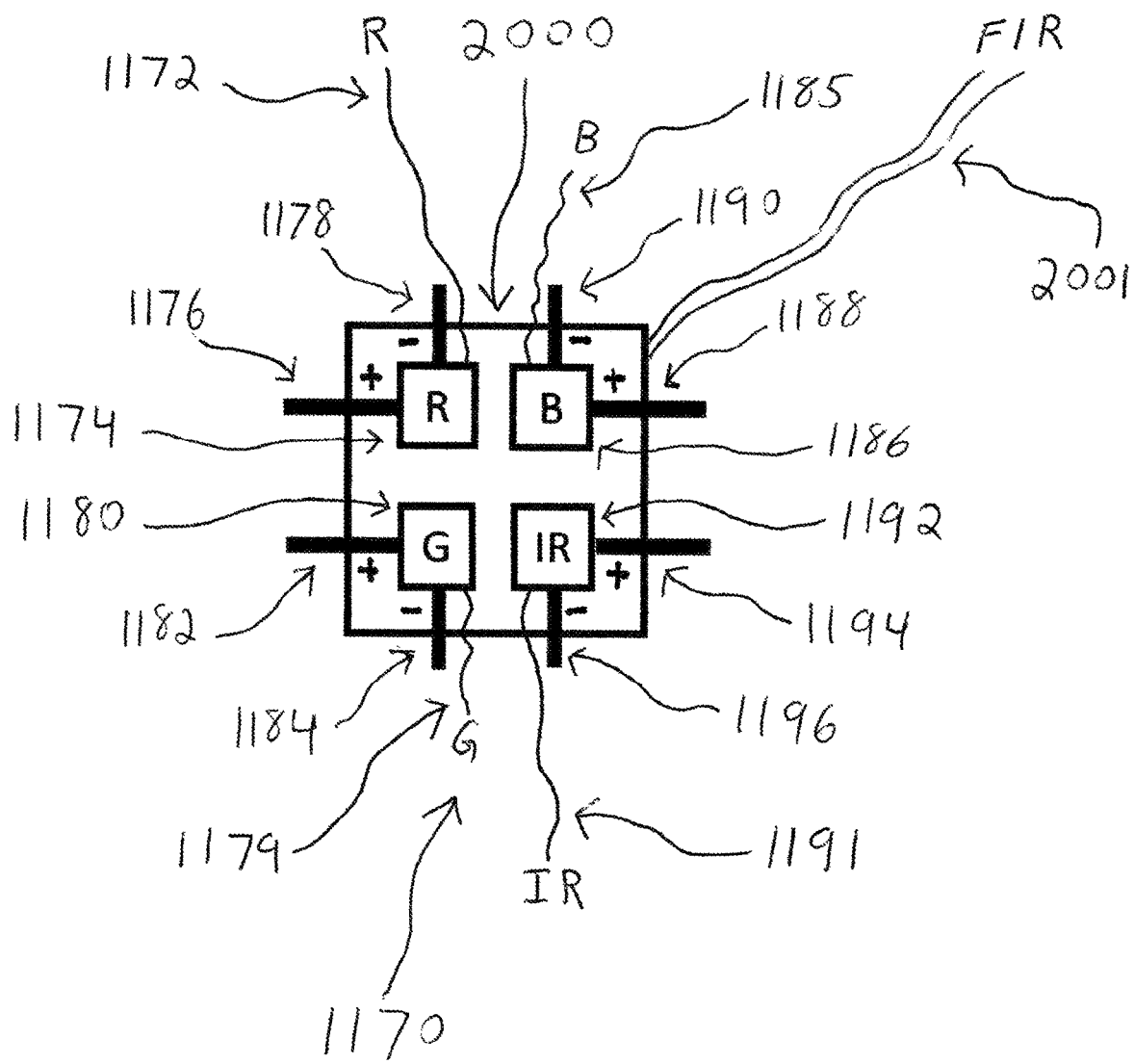
FIG. 22 shows a schematic view of an embodiment according to the invention.

FIG. 22 shows and describes an example embodiment of a RGB-IR circuit array 1170 according to the invention. The RGB-IR circuit array 1170 comprises at least one of each of a red wavelength of light 1172 light emitter 1174 comprising a positive electrical contact 1176 and a negative electrical contact 1178, a green wavelength of light 1179 light emitter 1180 comprising a positive electrical contact 1182 and a negative electrical contact 1184, a blue wavelength of light 1185 light emitter 1186 comprising a positive electrical contact 1188 and a negative electrical contact 1190, and a IR wavelength of light 1191 light emitter 1192 comprising a positive electrical contact 1194 and a negative electrical contact 1196 collectively forming an RGB-IR circuit array 1170 mounted to a substrate 2000, which may be a single substrate and which may be made of and/or include a material including but not limited to graphene and configured to emit FIR wavelengths of light 2001 from the substrate 2000. Each individual wavelength of light emitted from the RGB-IR circuit array is individually addressable and/or control-able in its level of energy emission by controlling the level, amount and/or duration of power being delivered to the RGB-IR circuit array 1170 via the electrical contacts of each light emitter within the RGB-IR circuit array 1170 by utilizing drivers and control methods including but not limited to PWM, PAM, PPM, and/or other modulation techniques known in the art. The RGB-IR circuit array 1170 is configured and/or may be constructed using one or a combination of light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs, and/or or other light emitting device technology. In the example embodiment of the RGB-IR circuit array 1170 LED chips are used to produce the RGB-IR wavelength emissions from the RGB-IR circuit array 1170 but it is contemplated by the inventor that a circuit array could be made using at least one QLED or QD-LED and at least one IR-LED and/or IR-OLED thereby eliminating the need for the red light emitter 1174 and the green light emitter 1180 leaving only the blue light emitter 1186 and the IR light emitter 1192 which would result in providing a quantum dot blue-IR circuit array ("QD-BIR") circuit array 2100 as further described in FIG. 23. The RGB-IR circuit array 1170 could comprise LED chips or OLEDs mounted to or formed on the substrate 2000 to provide an RGB-IR LED array or an RGB-IR LED chip circuit that can be used as a light source including but not limited to one or more pixels in a display and the substrate 2000 may be at least one of, the substrate of a video display within an electronic display device, a surface mountable substrate that can be mounted to another substrate, or optionally be at least one of the substrates within an LED package or lighting device and constructed to provide an RGB-IR LED package and that the RGB-IR LED array and/or RGB-IR LED package (either of which being an "RGB-IR LED component") could be surface mounted to a printed circuit board and/or other substrates and allow for each and/or a group of individual RGB-IR chips within the RGB-IR component to be individually controlled in power level and/or light energy emission by using various power supplies, drivers and/or drive schemes including but not limited to constant voltage, constant current, pulse width modulation ("PWM"), high frequency AC, high voltage AC or high voltage rectified AC, linear step drive, buck boost, pulsed drive, or other LED driver and/or methods known to those skilled in the art. The RGB-IR component may be used to provide the features of the device 100 described within the various embodiments of the invention in FIGS. 15-21 described herein as well as the RGB-IR LED could be utilized as at least one pixel within an electronic device comprising at least one electronic video display. It is contemplated by the inventors that any of the circuit arrays and/or components according to the inventions described here could be used in lighting applications other than displays including but not limited to lighting devices for medical devices, general lighting products and other lighting applications. One or a plurality of the RGB-IR circuit array(s) 1170 may be integrated into an electronic video display device including but not limited to the electronic visual and/or video display devices as described in FIGS. 15 to 21.

Figure 23:
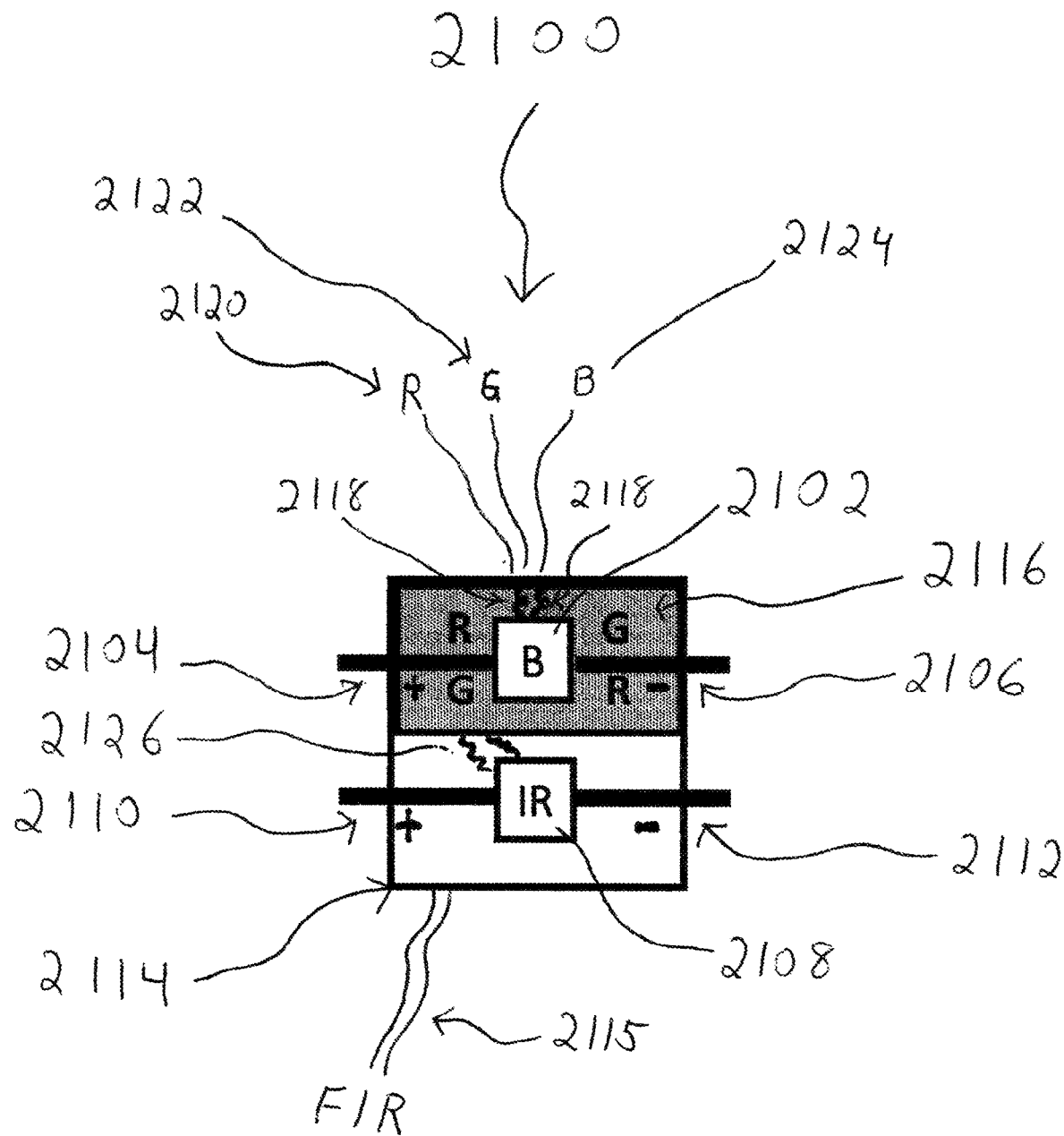
FIG. 23 shows a schematic view of an embodiment according to the invention.

FIG. 23 shows and describes in more detail an example embodiment of a quantum dot blue-IR circuit array ("QD-BIR") circuit array 2100 as mentioned in the description of FIG. 22. The QD-BIR circuit array 2100 comprises at least one of each of a blue wavelength light emitter 2102 comprising a positive electrical contact 2104 and a negative electrical contact 2106 and a IR wavelength light emitter 2108 comprising a positive electrical contact 2110 and a negative electrical contact 2112 collectively providing and/or forming an QD-BIR circuit array 2100 mounted to a substrate 2114 which may be a single substrate and which may be made of and/or include a material including but not limited to graphene and configured to emit FIR wavelengths of light 2015 from the substrate 2114. The IR wavelength light emitter 2106 and/or just the blue wavelength light emitter 2102 may be configured to be coated with nanoparticles and/or quantum dots 2116 and/or positioned behind or beneath a layer of quantum dots 2116 or a video display light emission panel and/or a film comprising a quantum dots 2116 such that the emission of blue light wavelengths 2118 emitted from the blue wavelength light emitter 2102 can be converted into or a combination of red wavelengths of light 2120, green wavelength of light 2122, and/or a blue wavelengths of light 2124. Quantum dots 2116 that covert the blue light wavelengths 2118 may also be used to convert the emission of IR wavelengths 2126 however it is possible that a different quantum dots may be used to convert the IR wavelengths 2126 such quantum dots used in films that have a simple, two-layer structure. The bottom layer may consist of colloidal quantum dots. These are nanometer-sized chunks of the semiconductor lead sulfide coated with a molecular layer of fatty acids. The top layer is a crystalline film made of an organic molecule called rubrene which when used to convert IR wavelengths of light has been proven to convert non-visible wavelengths of IR to visible light. Each individual wavelength of light emitted from the QD-BIR circuit array 2100 is individually addressable and/or control-able in its level of energy emission by controlling the level, amount and/or duration of time power is being delivered to the RGB-IR circuit array 1170 via the electrical contacts of each light emitter within the RGB-IR circuit array 1170 by utilizing drivers and control methods including but not limited to PWM, PAM, PPM, and/or other modulation techniques know in the art. The RGB-IR circuit array 1170 is configured and/or may be constructed using one or a combination of light emitting devices such as LEDs and/or OLEDs including but not limited to quantum dot LEDs ("QLEDs") quantum dot OLEDs ("QD-OLEDs"), or other light emitting device technology. In the example embodiment of the RGB-IR circuit array 1170 LED chips are used to produce the RGB-IR wavelength emissions from the RGB-IR circuit array 1170 but it is contemplated by the inventor that a circuit array could be made using at least one QLED or QD-LED and at least one IR-LED and/or IR-OLED thereby eliminating the need for the red light emitter 1174 and the green light emitter 1180 leaving only the blue light emitter 1186 and the IR light emitter 1192 which would result in providing a quantum dot blue-IR circuit array ("QD-BIR") circuit array 2100 as further described in FIG. 23. The RGB-IR circuit array 1170 could comprise LED chips or OLEDs mounted to or formed on the substrate 2000 to provide an RGB-IR LED array or an RGB-IR LED chip circuit that can be used as a light source including but not limited to one or more pixels in a display and the substrate 2000 may be at least one of, the substrate of a video display within an electronic display device, a surface mountable substrate that can be mounted to another substrate, or optionally be at least one of the substrates within an LED package or lighting device and constructed to provide an RGB-IR LED package and that the RGB-IR LED array and/or RGB-IR LED package (either of which being an RGB-IR LED component) could be surface mounted to a printed circuit board and/or other substrates and allow for each and/or a group of individual RGB-IR chips within the RGB-IR component to be individually controlled in power level and/or light energy emission by using various power supplies, drivers, and/or drive schemes including but not limited to constant voltage, constant current, pulse width modulation ("PWM"), high frequency AC, high voltage AC or high voltage rectified AC, linear step drive, buck boost, pulsed drive, or other LED driver, and/or methods known to those skilled in the art. The RGB-IR component may be used to provide the features of the device 100 described within the various embodiments of the invention in FIGS. 15-21 described herein as well as the RGB-IR LED could be utilized as at least one pixel within an electronic device comprising at least one electronic video display. It is contemplated by the inventors that any of the circuit arrays and/or components according to the inventions described herein could be used in lighting applications other than displays including but not limited to lighting devices for medical devices, general lighting products and other lighting applications. One or a plurality of the QD-BIR circuit array(s) 2100 may be integrated into an electronic video display device including but not limited to the electronic visual and/or video display devices as described in FIGS. 15 to 21.

Figure 24:
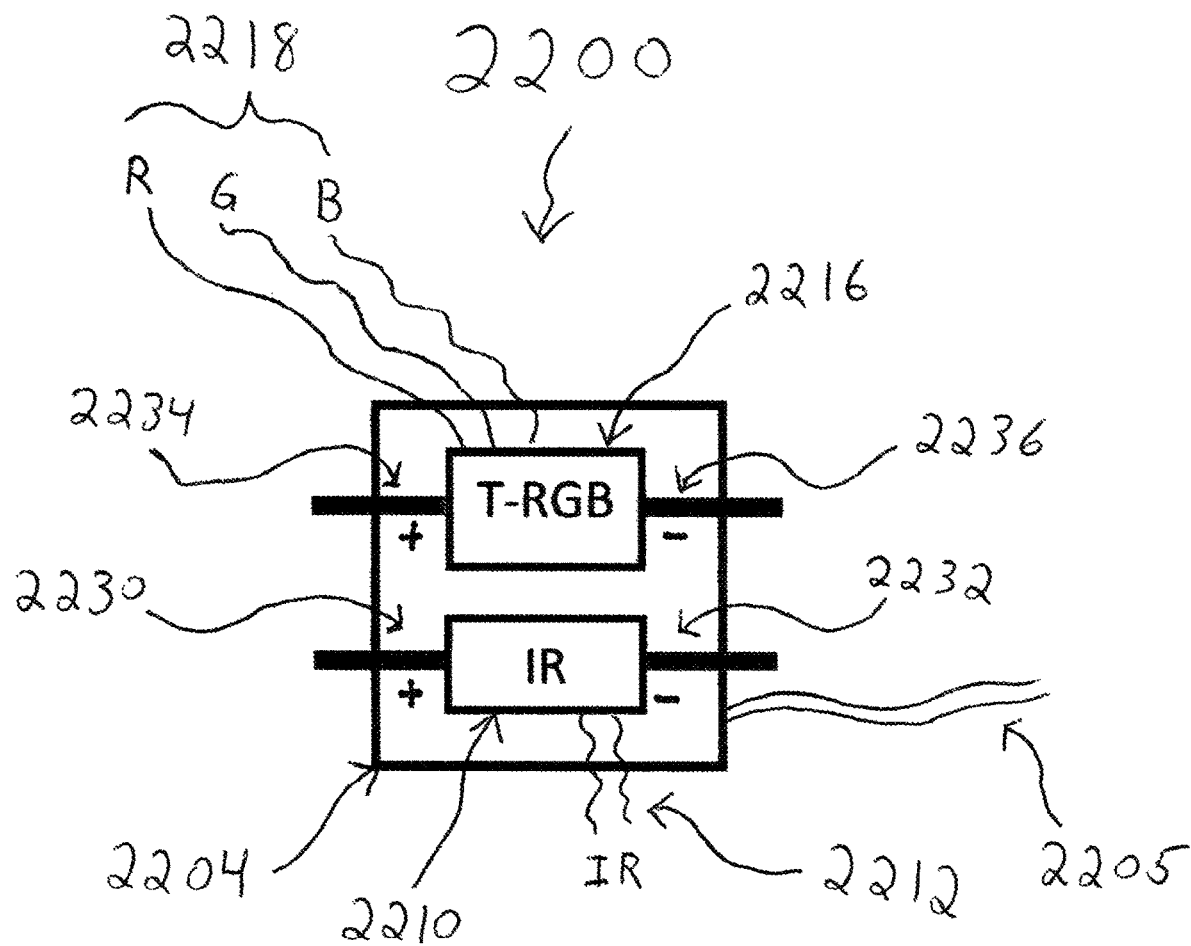
FIG. 24 shows a schematic view of an embodiment according to the invention.

FIG. 24 shows and describes an example embodiment of a Tunable RGB-IR ("TRGB-IR") circuit array 2200 according to the invention. The TRGB-IR circuit array 2200 comprises at least one TRGB-IR circuit array 2202 mounted to and/or formed on a substrate 2204 which may be a single substrate 2204 and which may be made of and/or include a material including but not limited to graphene and configured to emit FIR wavelengths of light 2205 from the substrate 2204. The TRGB-IR circuit array 2202 comprises at least one IR LED chip 2210 configured to emit at least one IR wavelengths of light 2212 and at least one Tunable-RGB ("T-RGB") LED chip 2216 that is configured to controllably emit one and/or any combination of red ("R"), green ("G"), and/or blue ("B") ("RGB") wavelengths of light 2218 at various intensities that can produce over sixteen million colors and/or wavelength of light emission from the T-RGB LED chip 2216 when/by tuning the voltage and/or current being delivered to the T-RGB LED chip 2216. The TRGB-IR circuit array 2200 comprises at least one positive voltage electrical contact 2230 and at least one negative voltage and/or ground electrical contact 2232 connected to the IR LED chip 2210, and at least one positive voltage electrical contact 2234 and at least one negative voltage electrical contact 2236 connected to the at least one T-RGB LED chip 2216. The at least one positive voltage electrical contact 2230 and the at least one negative voltage and/or ground electrical contact 2232 may be mounted to, formed on, and/or an integral part of the substrate 2204 and electrically connected to the at least one IR LED chip 2210, and the at least one positive voltage electrical contact 2234 and the at least one negative voltage and/or ground electrical contact 2236 may be mounted to, formed on, and/or an integral part of the substrate 2204 and electrically connected to the at least one T-RGB LED chip 2216. Each individual IR LED chip 2212 and T-RGB LED chip 2216 configured to emit wavelengths of light 2212 and 2218 is individually addressable and/or controllable in its level of power input and wavelengths energy emissions by controlling the level, amount and/or duration of power being delivered to the TRGB-IR circuit array 2200 via the respective electrical contacts of each of the T-RGB chip(s) 2216 and IR chip(s) 2210 by utilizing drivers and control methods including but not limited to PWM, PAM, PPM, and/or other modulation techniques know in the art. A plurality of TRGB-IR circuit array(s) 2200 can be combined in a device, electronic visual display device and/or system comprising other light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs, and/or or other light emitting device technology. One or a plurality of the TRGB-IR circuit array(s) 2200 may be integrated into an electronic video display device including but not limited to the electronic visual and/or video display devices as described in FIGS. 15 to 21.

Figure 25:
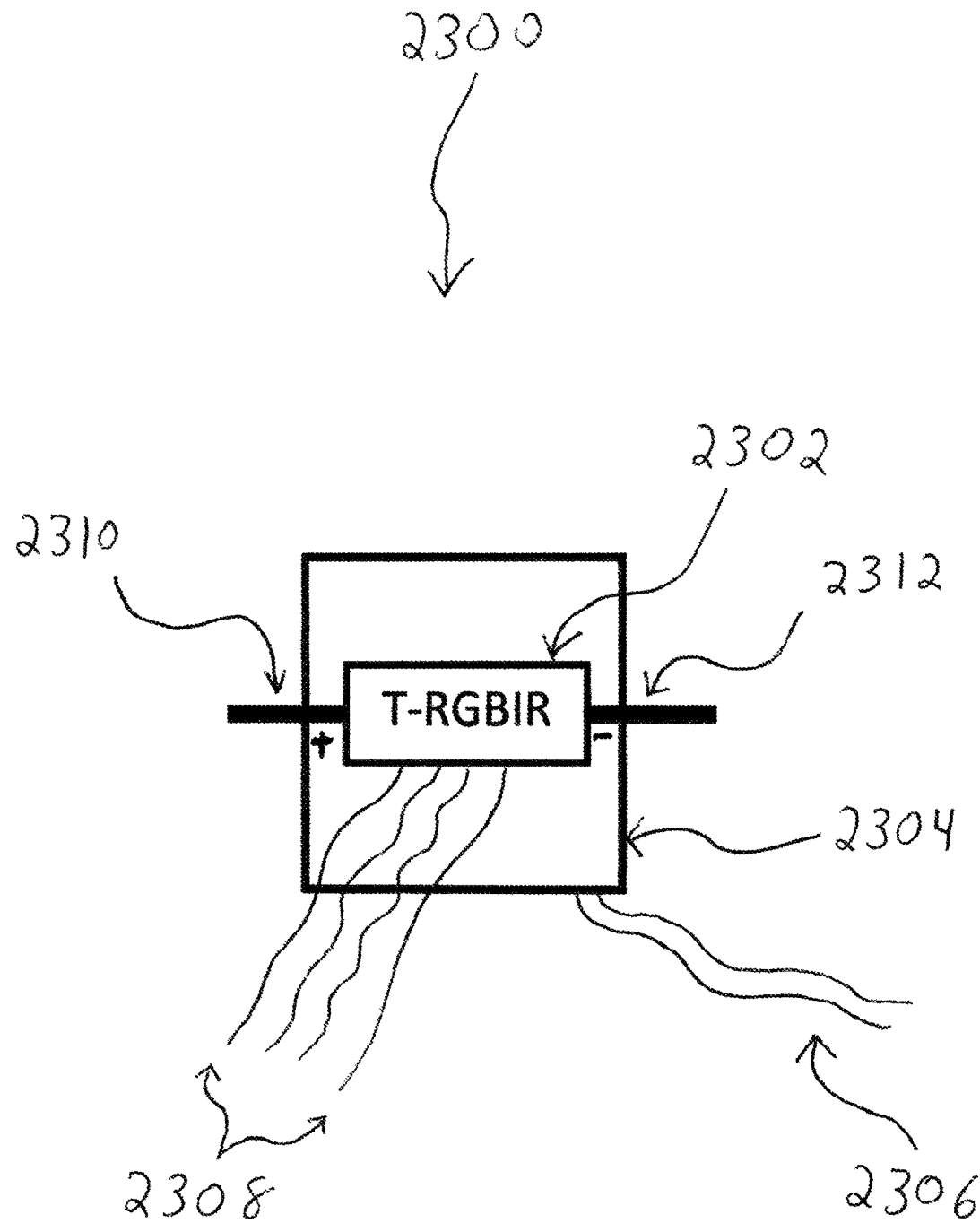
FIG. 25 shows a schematic view of an embodiment according to the invention.

FIG. 25 shows and describes an example embodiment of a tunable red, green, blue, infrared ("RGB-IR") ("T-RGBIR") light emitting device 2300 according to the invention. The T-RGBIR light emitting device 2300 comprises at least one T-RGBIR light emitter 2302 mounted to and/or formed on a substrate 2304 which may be a single substrate 2304 and which may be made of and/or include a material including but not limited to graphene and configured to emit FIR wavelengths of light 2306 from the substrate 2304. The T-RGBIR light emitting device 2302 comprises at least one Tunable RGBIR "T-RGBIR" light emitter 2302 which may be a LED chip that is configured to controllably emit one and/or any combination of red ("R"), green ("G"), blue ("B"), and/or IR ("RGBIR") wavelengths of light 2308 at various energy levels and/or intensities that can produce over sixteen million colors and/or wavelength of light and/ infrared light/energy emission from the T-RGBIR light emitter 2302 when/by tuning the voltage and/or current being delivered to the T-RGBIR light emitting device 2300. The T-RGBIR light emitting device 2300 comprises at least one positive voltage electrical contact 2310 and at least one negative voltage and/or ground electrical contact 2212 connected to the at least one T-RGBIR light emitter 2302. The at least one positive voltage electrical contact 22310 and the at least one negative voltage and/or ground electrical contact 2312 may be mounted to, formed on, and/or an integral part of the substrate 2306 and electrically connected to the at least one T-RGBIR light emitter 230. The T-RGBIR light emitting device 2300 is configured to emit one or a combination of any two or more wavelengths of light 2308 and the T-RGBIR light emitter is individually addressable and/or controllable in its level of power input and wavelengths energy emissions by controlling the level, amount and/or duration of power being delivered to the T-RGBIR circuit light emitting device 2300 and/or T-RGBIR light emitter 2302 via the respective electrical contacts 2310 and 2312 by utilizing drivers and control methods including but not limited to PWM, PAM, PPM, and/or other modulation techniques know in the art. A plurality of T-RGBIR light emitting devices 2300 can be combined in a device, electronic visual display device and/or system comprising other light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs, and/or or other light emitting device technology. One or a plurality of the T-RGBIR light emitting device(s) 2300 may be integrated into an electronic video display device including but not limited to the electronic visual and/or video display devices as described in FIGS. 15 to 21.

Figure 26:
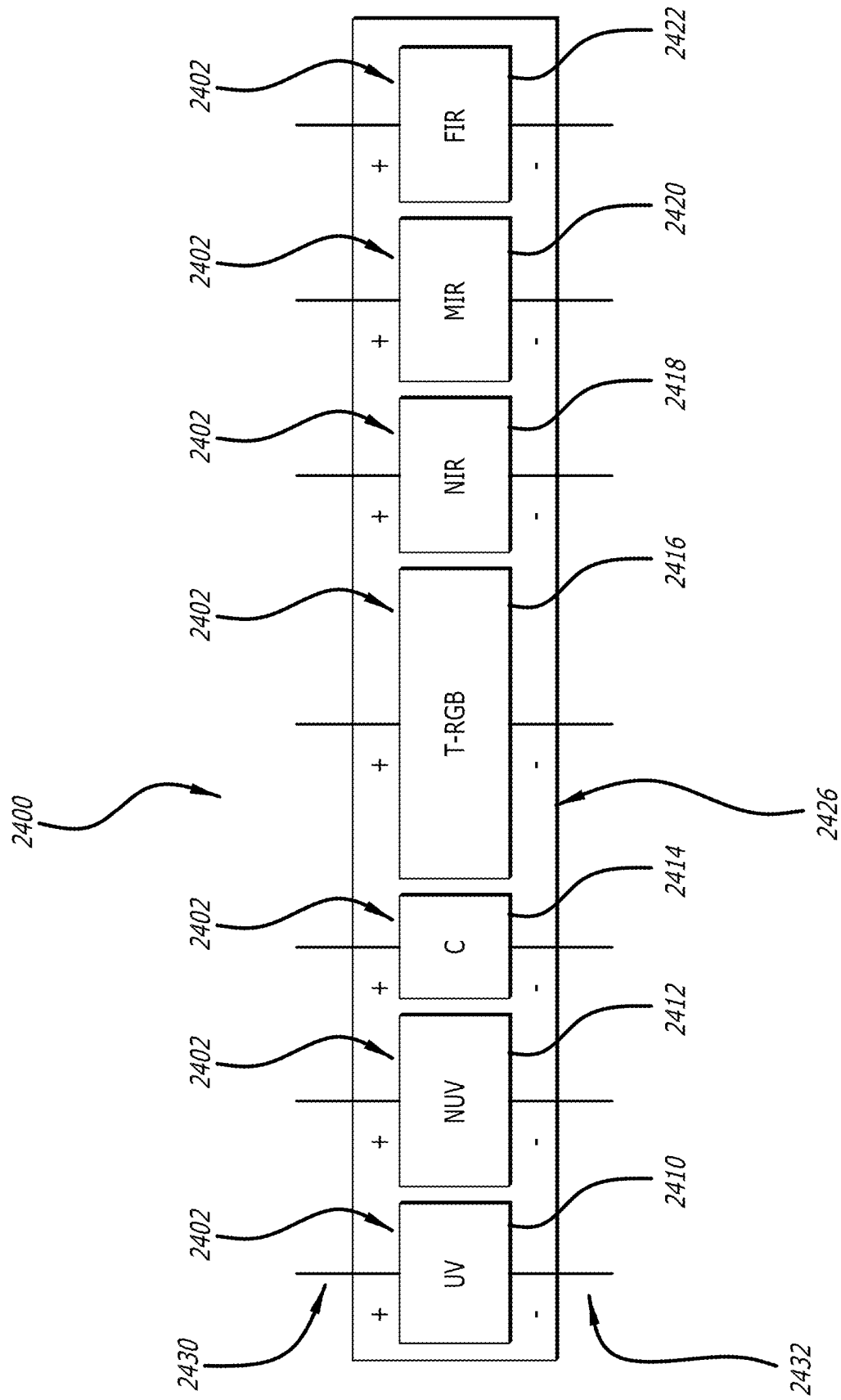
FIG. 26 shows a schematic view of an embodiment according to the invention.

FIG. 26 shows and describes another example embodiment of a Tunable Broad Spectrum Pixel "T-BSP" 2400 comprising a plurality of light emitters 2402 configured to include at least one of each of a UV light emitter 2410, a near-UV ("NUV") light emitter 2412, a cyan wavelength light emitter 2414, a tunable RGB ("T-RGB") light emitter 2416 (similar to the T-RGB light emitter described herein such as in FIGS. 15, 24, and 25), a near-IR light emitter 2418, a Mid-IR ("MIR") light emitter 2420, and a Far-IR ("FIR") light emitter 2422 (light emitters 2410-2422) mounted to and/or formed on a substrate 2424 which may be made of and/or include a material including but not limited to graphene and configured to emit FIR wavelengths of light 2306 from the substrate 2424. Each of the light emitters 2410-2422 within the plurality of light emitters 2402 each comprises at least one positive electrical contact.

The T-RGBIR light emitting device 2302 comprises at least one Tunable RGBIR ("T-RGBIR") light emitter 2302, which may be a LED chip that is configured to controllably emit one and/or any combination of red ("R"), green ("G"), blue ("B"), and/or IR ("RGBIR") wavelengths of light 2308 at various energy levels and/or intensities that can produce over sixteen million colors and/or wavelength of light and/ infrared light/energy emission from the T-RGBIR light emitter 2302 when/by tuning the voltage and/or current being delivered to the T-RGBIR light emitting device 2300. The T-BSP 2400 comprises at least one positive voltage electrical contact 2430 and at least one negative voltage and/or ground electrical contact 2432 connected to the at least one T-RGBIR light emitter 2302. The at least one positive voltage electrical contact 2310 and the at least one negative voltage and/or ground electrical contact 2312 may be mounted to, formed on, and/or an integral part of the substrate 2306 and electrically connected to the at least one T-RGBIR light emitter 230. The T-RGBIR light emitting device 2300 is configured to emit one or a combination of any two or more wavelengths of light 2308 and the T-RGBIR light emitter is individually addressable and/or controllable in its level of power input and wavelengths energy emissions by controlling the level, amount and/or duration of power being delivered to the T-RGBIR circuit light emitting device 2300 and/or T-RGBIR light emitter 2302 via the respective electrical contacts 2310 and 2312 by utilizing drivers and control methods including but not limited to PWM, PAM, PPM, and/or other modulation techniques know in the art. A plurality of T-RGBIR light emitting devices 2300 can be combined in a device, electronic visual display device and/or system comprising other light emitting devices such as LEDs and/or OLEDs including but not limited to quantum dot LEDs ("QLEDs"), quantum dot OLEDs ("QD-OLEDs"), Micro-LEDs including but not limited to dynamically tuned QLEDs, QD-OLEDs, micro-LEDs, and/or or other light emitting device technology. One or a plurality of the T-RGBIR light emitting device(s) 2300 may be integrated into an electronic video display device including but not limited to the electronic visual and/or video display devices as described in FIGS. 15 to 21.

FIG. 26 shows and describes an example embodiment of a Seven "7" Channel Controllable Broad Spectrum Pixel ("7CC-BSP") 2400 comprising a plurality of different electromagnetic wavelength energy light emitters 2402 configured to include at least one of each of a UV light emitter 2410, a near-UV ("NUV") light emitter 2412, a cyan wavelength light emitter 2414, a tunable RGB ("T-RGB") light emitter 2416 (similar to the T-RGB light emitter described herein such as in FIGS. 15, 24, and 25), a near-IR light emitter 2418, a mid-IR ("MIR") light emitter 2420, and a far-IR ("FIR") light emitter 2422 (light emitters 2410-2422) mounted to and/or formed on a substrate 2426 which may be a backplane. The substrate 2426 may be made of at least one of metal oxide semiconductor including but not limited to CMOS, NMOS, PMOS, a glass, graphene, or other rigid or flexible substrate material. The 7CC-BSP 2400 comprises at least one Tunable-RGB ("T-RGB") LED chip 2416 that is configured to controllably emit one and/or any combination of red ("R"), green ("G"), and/or blue ("B") ("RGB") wavelengths of light at various intensities that can produce over sixteen million colors and/or wavelength of light emission from the T-RGB LED chip 2416 when/by tuning the voltage and/or current being delivered to the T-RGB LED chip 2416. Each of the light emitters 2402 comprises at least one positive voltage electrical contact 2430 and at least one negative voltage and/or ground electrical contact 2432 connected to the light emitters 2402 and/or 2410-2422. The at least one positive voltage electrical contact 2430 and the at least one negative voltage and/or ground electrical contact 2432 may be mounted to, formed on, and/or an integral part of the substrate 2426 and electrically connected to each respective light emitter 2410-2422. Each of the individual light emitters 2410 to 2422 are configured to be individually addressable and/or controllable in its level of power input and wavelengths of electromagnetic energy emissions by controlling the level, amount and/or duration of power being delivered to the 7CC-BSP 2400 via the respective positive and negative electrical contacts of each individual light emitter 2402 and/or 2410-2422 by utilizing drivers and control methods including but not limited to constant voltage, constant current, pulse width modulation "PWM", pulse amplitude modulation ("PAM"), pulse position modulation ("PPM"), high frequency sign wave and/or square wave drive, high voltage AC or rectified AC, linear step drive, buck boost, pulsed drive, resistor/capacitor ("RC") network circuit driven using frequency modulation, or other LED driver and/or drive methods known to those skilled in the art. A plurality of 7CC-BSPs 2400 can be combined in a single device, electronic visual display device and/or system comprising other light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs, and/or or other light emitting device technology. A plurality of 7CC-BSPs 2400 can be used to form a portion of, or an entire electronic video display and some of the light emitters 2402 that emit wavelengths of electromagnetic energy that is visible to the human eye may function and/or be utilized to produce images on the electronic video display while at the same or different times the light emitters 2402 that emit wavelengths of electromagnetic energy that are visible and/or invisible to the human eye may function and/or be utilized to produce antibacterial and/or biologically beneficial wavelengths of electromagnetic energy towards a person and/or the eye(s) of a person simultaneously or independently of the electronic video display device displaying video images viewed by a person. The 7CC-BSPs 2400 may be integrated into an electronic device comprising a video display such as the electronic visual and/or video display devices as described in FIGS. 15 to 21. It is contemplated by the inventors that one or a plurality of the 7CC-BSP 2400 may also be integrated and/or used for applications other than a pixel such as a broad spectrum LED component and/or package that can be used in devices for lighting applications not related to video displays such as medical lighting, general lighting, medical devices or other applications in which case it would not be a pixel but still provide the similar features and emission of the described wavelengths of electromagnetic energy.

Figure 27:
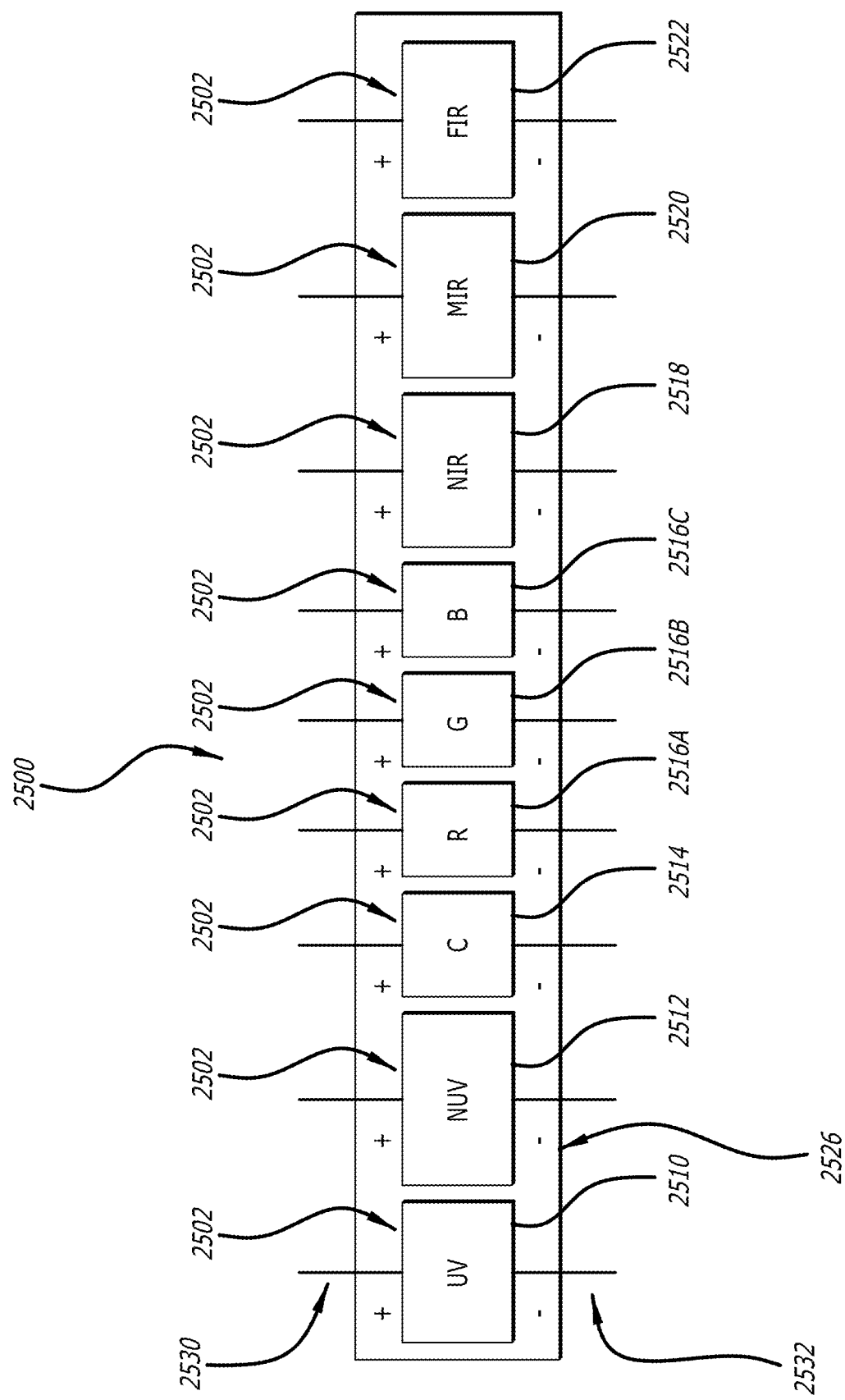
FIG. 27 shows a schematic view of an embodiment according to the invention.

FIG. 27 shows and describes an example embodiment of a Nine "9" Channel Controllable Broad Spectrum Pixel ("9CC-BSP") 2500, which is similar to the 7CC-BSP shown in FIG. 26 except that the T-RGB light emitter 2416 has been replaced with individual RGB light emitters 2516A, 2516B, and 2516C. The 9CC-BSP 2500 comprises a plurality of different electromagnetic wavelength energy light emitters 2502 configured to include at least one of each of a UV light emitter 2510, a near-UV ("NUV") light emitter 2512, a cyan wavelength light emitter 2514, a red wavelength light emitter 2516A, a green wavelength light emitter 2516B, a blue wavelength light emitter 2516C, a near-IR light emitter 2518, a mid-IR ("MIR") light emitter 2520, and a far-IR ("FIR") light emitter 2522 (light emitters 2510-2522) mounted to and/or formed on a substrate 2526 which may be a backplane. The substrate 2526 may be made of at least one of metal oxide semiconductor including but not limited to CMOS, NMOS, PMOS, a glass, graphene, or other rigid or flexible substrate material. Each of the light emitters 2502 comprises at least one positive voltage electrical contact 2530 and at least one negative voltage and/or ground electrical contact 2532 connected to the light emitters 2402 and/or 2410-2422. The at least one positive voltage electrical contact 2530 and the at least one negative voltage and/or ground electrical contact 2532 may be mounted to, formed on, and/or an integral part of the substrate 2526 and electrically connected to each respective light emitter 2510-2522. Each of the individual light emitters 2510 to 2522 are configured to be individually addressable and/or controllable in its level of power input and wavelengths of electromagnetic energy emissions by controlling the level, amount and/or duration of power being delivered to 9CC-BSP 2500 via the respective positive and negative electrical contacts of each individual light emitter 2502 and/or 2510-2522 by utilizing drivers and control methods including but not limited to constant voltage, constant current, pulse width modulation ("PWM"), pulse amplitude modulation ("PAM"), pulse position modulation ("PPM"), high frequency sign wave and/or square wave drive, high voltage AC or rectified AC, linear step drive, buck boost, pulsed drive, resistor/capacitor ("RC") network circuit driven using frequency modulation, or other LED driver and/or drive methods known to those skilled in the art. A plurality of 9CC-BSPs 2500 can be combined in a single device, electronic visual display device and/or system comprising other light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs, and/or or other light emitting device technology. A plurality of 9CC-BSP Pixels 2500 can be used to form a portion of, or an entire electronic video display and some of the light emitters 2502 that emit wavelengths of electromagnetic energy that is visible to the human eye may function and/or be utilized to produce images on the electronic video display while at the same or different times the light emitters 2502 that emit wavelengths of electromagnetic energy that are visible and/or invisible to the human eye may function and/or be utilized to produce antibacterial and/or biologically beneficial wavelengths of electromagnetic energy towards a person and/or the eye(s) of a person simultaneously or independently of the electronic video display device displaying video images viewed by a person. The 9CC-BSPs 2500 may be integrated into an electronic device comprising a video display such as the electronic visual and/or video display devices as described in FIGS. 15 to 21. It is contemplated by the inventors that one or a plurality of the 9CC-BSP 2500 may also be integrated and/or used for applications other than a pixel such as a broad spectrum LED component and/or package that can be used in devices for lighting applications not related to video displays such as medical lighting, general lighting, medical devices or other applications in which case it would not be a pixel but still provide the similar features and emission of the described wavelengths of electromagnetic energy.

Figure 27A:
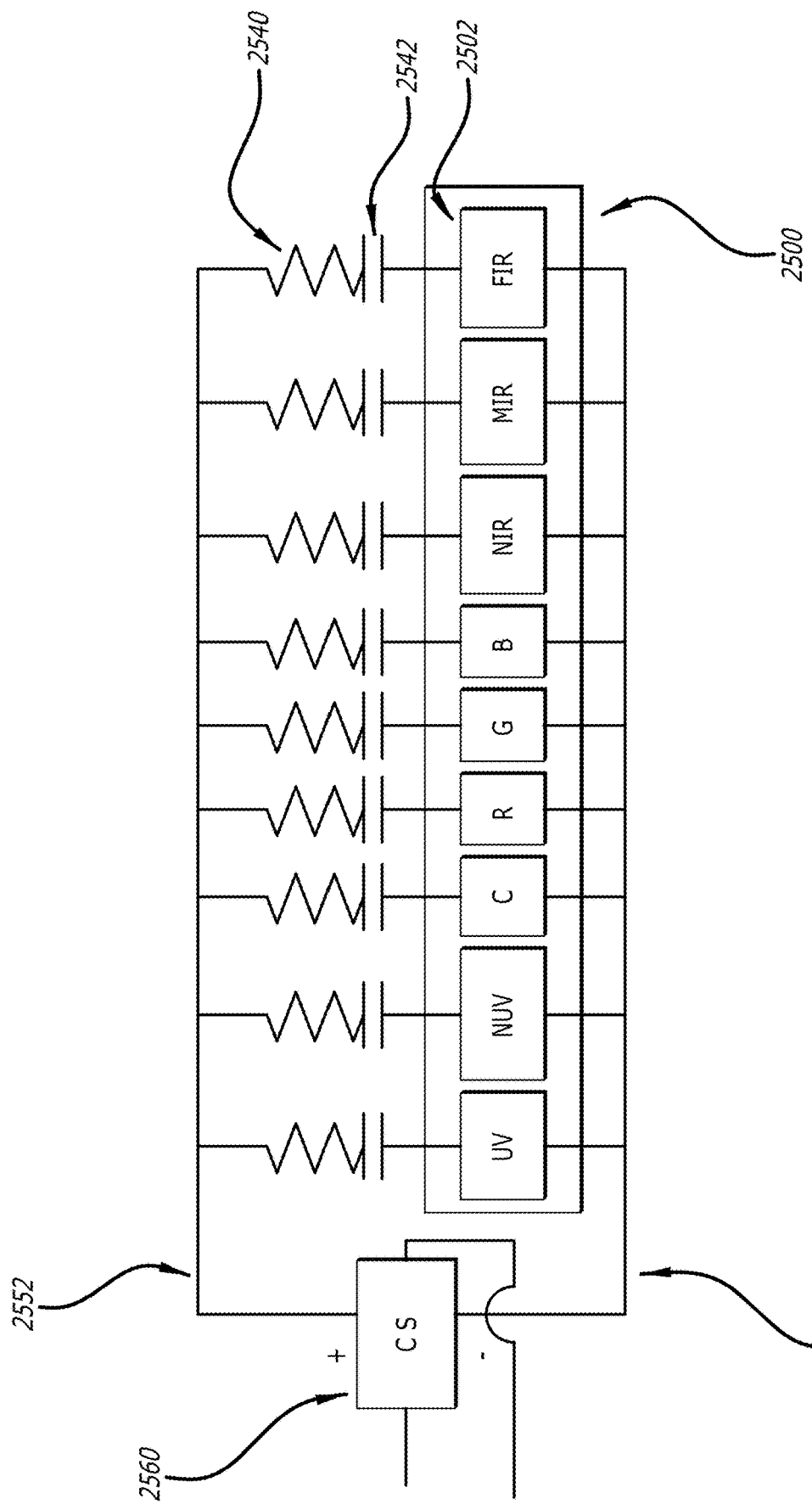
FIG. 27A shows a schematic view of an embodiment according to the invention.

FIG. 27A shows and describes an example embodiment of a similar Nine "9" Channel Controllable Broad Spectrum Pixel "9CC-BSP" 2500 as described in FIG. 27 and includes at least one resistor 2540 and at least one capacitor 2542 connected in series with at least one of the light emitters 2502 and/or 2510-2522. The resistor 2540 and capacitor 2542 may be connected in series with each other and in series with the at least one light emitter 2502 as shown in FIG. 27A, or the resistor 2540 and capacitor 2542 may be in parallel with each other and connected in series to the light emitter(s) 2502. Alternatively, the resistor 2540 may be connected in series with the positive electrical contact 2530 and the capacitor may be connected in series with the negative electrical contact 2532 of at least one of the light emitters 2502 thereby providing an RC network circuit in series with the at least one or more light emitters 2502 to enable simplified and reduced wiring and/or electrical connections leads 2550 and 2552 needed for each of the 9CC-BSP or device 2500 which may be as few as two leads wires per individual 9CC-BSP or device 2500 in an electronic display device comprising the 9CC-BSP or device 2500. The wires and/or leads 2550 and 2552 may be connected to the output of a circuit and/or device 2560 that provides output control signals at various voltage levels and frequencies. The voltage levels and frequencies may be sent in data packets and/or multiplexed out onto the wires and/or leads 2550 and 2552 and the resistors 2540 and capacitors 2542 would be able to receive and/or filter out the particular signals (voltages and/or frequencies) allowing for all nine channels connected to each individual light emitter 2502 to be controlled with as few as two wires and/or leads going to each 9CC-BSP 2500. It is contemplated by the inventors that an indictor can also be added to each resistor 2540, capacitor 2542 and/or light emitter 2502 as part of the circuit and these same concepts can be implemented in the devices and/or pixels as described in FIGS. 22 to 26. The substrate 2526 for the 9CC-BSP may also include the RC network components mounted and/or hosted on the same substrate as the 9CC-BSP. Each of the individual light emitters 2510 to 2522 are configured to be individually addressable and/or controllable in its level of power input and wavelengths of electromagnetic energy emissions by controlling the level, amount and/or duration of power being delivered to 9CC-BSP 2500 via the respective positive electrical contacts and/or inputs to each individual light emitter 2502 and/or 2510-2522 by utilizing drivers and control methods including but not limited to constant voltage, constant current, pulse width modulation ("PWM"), pulse amplitude modulation ("PAM"), pulse position modulation ("PPM"), high frequency sign wave and/or square wave drive, high voltage AC or rectified AC, linear step drive, buck boost, pulsed drive, resistor/capacitor ("RC") network circuit driven using frequency modulation, or other LED driver and/or drive methods known to those skilled in the art. A plurality of 9CC-BSPs 2500 can be combined in a single device, electronic visual display device and/or system comprising other light emitting devices such as LEDs and/or OLEDs including but not limited to quantum dot LEDs ("QLEDs"), quantum dot OLEDs ("QD-OLEDs"), micro-LEDs including but not limited to dynamically tuned QLEDs, QD-OLEDs, micro-LEDs and/or or other light emitting device technology. A plurality of 9CC-BSPs 2500 can be used to form a portion of, or an entire electronic video display and some of the light emitters 2502 that emit wavelengths of electromagnetic energy that is visible to the human eye may function and/or be utilized to produce images on the electronic video display while at the same or different times the light emitters 2502 that emit wavelengths of electromagnetic energy that are visible and/or invisible to the human eye may function and/or be utilized to produce antibacterial and/or biologically beneficial wavelengths of electromagnetic energy towards a person and/or the eye(s) of a person simultaneously or independently of the electronic video display device displaying video images viewed by a person. The 9CC-BSPs 2500 may be integrated into an electronic device comprising a video display such as the electronic visual and/or video display devices as described in FIGS. 15 to 21. It is contemplated by the inventors that one or a plurality of the 9CC-BSP 2500 may also be integrated and/or used for applications other than a pixel such as a broad spectrum LED component and/or package that can be used in devices for lighting applications not related to video displays such as medical lighting, general lighting, medical devices or other applications in which case it would not be a pixel but still provide the similar features and emission of the described wavelengths of electromagnetic energy.

It is further contemplated by the inventors that the device 1100 may be integrated into a ceiling light, a light bulb or any other form of light fixture that emits one or more color temperatures of white light white light, and preferably two or more color temperatures of white light, including but not limited into a lighting device that has user selectable color temperatures of white light or user controllable/tunable color temperatures of white light that fall within two or more white color temperatures between the ranges of 1000 to 10,000 Kelvin with the difference between the two color temperatures of white light being at least 250 kelvin such as 2700K and 3000K, or 3500K and 4100K for example and may also include one or more light emitters configured to emit RGB wavelengths of light. The device 1100 could include these white light emitters which may be phosphor coated light emitters and integrated together with one or more or any combination of the light emitters including RGB light emitters and/or light emitters 1102 and/or 1104, 1106, 1108 and/or 1110 into a ceiling light, a light bulb or any other form of light fixture, or a display or a display with an integrated light fixture that produces white light for purposes other than display images such as task lighting or accent lighting. It if further contemplated that the device 1100 may be integrated into other devices such as a speaker, including but not limited to a portable battery operated or power supply operated wireless speaker such as a Bluetooth speaker, or a ceiling mounted speaker. It is also contemplated the device 1100 could be integrated into the surrounding trim of a ceiling light or a ceiling speaker where the trim often has a given angle around the perimeter and that any one of the emitters 1102 and/or 1104, 1106, 1108 and/or 1110 could be integrated in the angled section of trim within a down light, ceiling light and/or speaker having such a trim with its housing. It is further contemplated that the device 1100 may include circuitry that can turn on and off any one or more of the light emitters 1102 and/or 1104, 1106, 1108 and/or 1110 sequentially using a sequencing circuit or a LED chaser circuit and the sequencing circuit may be configured to respond to a sensor including but not limited to include any sensors described herein and may emit a specific wavelength of IR and/or UV light towards a focused direction on an object and/or person while the other light emitters (white light emitters and/or visual display emitters for example) may distribute light in much wider and or broader direction than the IR and/or UV light being focused towards an object and/or a person.

It is further contemplated by the inventors that one or more or a combination of any devices including but not limited to the device 1100, a medical device, a light bulb, lighting device and/or lighting system comprising one or more of the inventions described herein may include one of more of a combination of any of the light emitters described herein including but not limited to RBG light emitters and/or light emitters 1102 and/or 1104, 1106, 1108 and/or 1110 and that any of the example embodiment described herein or other embodiments that incorporate one or more of the inventions described herein may be configured to be connected to the internet and/or internet of things, cloud storage, a blockchain or other networks to store data and/or information related to treatments, treatment history, usage and/or the amount of emissions of one or more of the wavelengths received by a living species and/or person and such data could be stored solely or both on local memory within a device and/or remote data storage sources for example into a cloud storage system, a blockchain communications and/or storage system, or other remote data storage and access devices and/or systems where the data and/or information may be accessible and controllable locally and/or remotely by a user, by a device, system or network comprising artificial intelligence "AI" and/or by a physician including but not limited to during a telemedicine communication between an AI and/or a physician and a patient. Any of the devices described herein that provide the wavelength emissions provided by the inventions described herein may also be connected to and in communications with other devices in a mesh network and such devices may or may not comprise one or more of the embodiments of the inventions described herein. As an example, one or more of the example embodiments/devices according to the invention(s) described in FIGS. 1-11 may be in wired or wireless communication with one or more of the example embodiments/devices described in FIG. 12-14, or 12-21, or a group of similar devices described in any one or more figures herein may be in wired or wireless communication with each other and/or another network including but not limited to remote data storage/management networks such as the Cloud or AI system as described herein.

It is further contemplated by the inventors that one or more and/or any combination of the IR, UV and/or white light emitters described herein could be integrated into a protective case used to protect a portable telecommunication device and that the protective case could include its own integrated power source such as a batter, and/or the protective case could receive power by wire and/or wirelessly from the portable communications device to provide power to the emitters.

It is further contemplated by the inventors that it could be advantageous to combine the use of any of the light and/or wavelength emitting devices described herein in conjunction with pharmaceuticals and/or photoreactive pharmaceuticals (pharmaceuticals) when delivering the AILR emissions into or onto a living species and that the delivery of such pharmaceuticals could be done via at least one wearable pharmaceutical delivery system which may comprise its own biofeedback information and dosage release control capabilities in response to certain measured/measurable biological parameters of a living species. The wearable pharmaceutical delivery system may also be in communications with another device which may also be a wearable device, a portable device comprising a video display, a ceiling or wall light, a light bulb, furniture including but not limited to residential or medical facility furniture, or medical devices that receive biofeedback information and dosage release control capabilities in response to certain measured/measurable biological parameters of a living species information and/or data related to a past, present or future requirements of a person and/or living species needing to receive one or more of the wavelengths of light emission described herein.

It is contemplated by the inventor that one or more of any one of the examples, or a combination of the example circuit arrays and/or light emitting devices described in FIGS. 22 to 27A could be integrated into or onto any one of a surface mountable LED package, a circuit board substrate for hosting circuit components, a substrate within a lighting device and/or a substrate within a display.

Figure 28A:
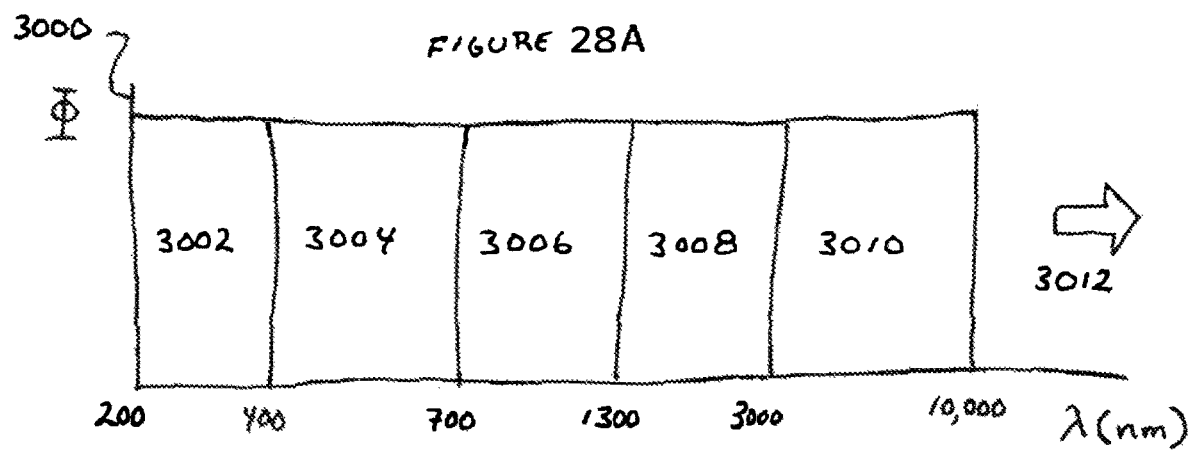
FIG. 28A shows a schematic view of an embodiment according to the invention.
Figure 28B:
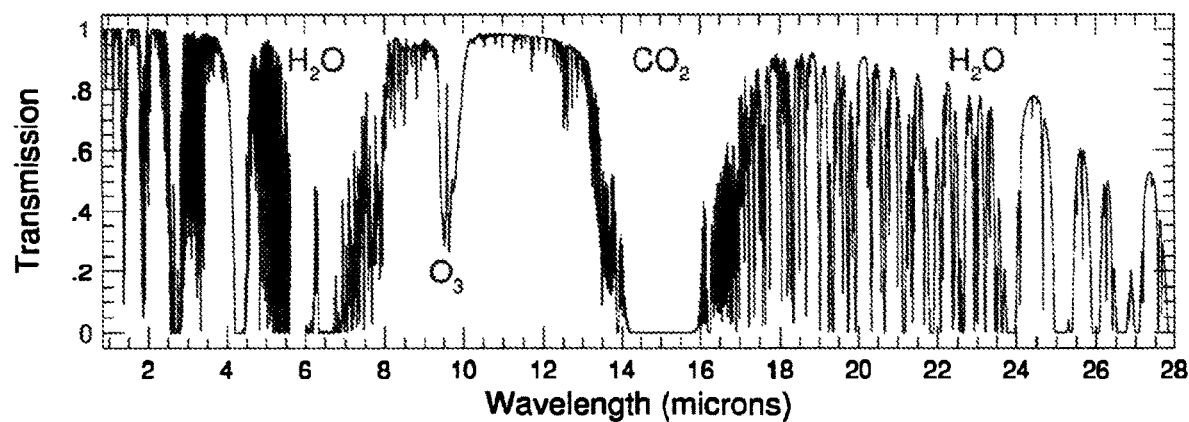
FIG. 28B shows a schematic view of an embodiment according to the invention.

FIGS. 28A and 28B show and provide a visualization of the approximate bands or ranges of wavelength bands of electromagnetic energy that can be provided by various devices according to the inventions described herein.

The range of wavelengths employed in such a device covers at least the range 3004 and more specifically between about 380 nanometers and 700 nanometers which corresponds roughly to the typical range of human vision and is thus provided primarily for illumination purposes. This range 3004 is also optionally adjustable by controlling individual or groups of discrete emission sources such that the emission profile is tailored for other purposes such as circadian entrainment, or other visible light mediated purposes. Additionally, the small range between 380 nanometers and 440 nanometers may be selectively controlled to provide for a level of disinfection or other electromagnetically mediated anti-bacterial/anti-viral/anti-fungal purposes or alternatively, to help stimulate the production of Vitamin D or other biological processes such as circadian entrainment or other purposes mitigated by these wavelengths of radiation.

FIG. 28B shows the typical atmospheric radiation transmission curve for radiation in our atmosphere and shows clear bands or windows of transmission and other wavelengths where absorption by carbon dioxide and water are known to attenuate the transmission of radiation. Typical sources of infrared radiation that are useful are known to transmit well through the atmospheric window regions and are well suited to providing benefits at a distance without attenuation. The radiation sources for the shorter infrared wavelengths, within the near-infrared ("NIR") region, will preferably be compact sources such as Light Emitting Diodes (LED), Vertical Cavity Surface Emitting Lasers (VCSELS), Carbon Nanotubes, or other devices such as tunable silicon-based devices or plasmonic grids that are configured to emit electromagnetic radiation into these wavelength regions. These sources could also have a smaller etendue that can be conveniently directed, and potentially steered, into narrower spatial distributions that can target specific areas of the body, either passively or actively, via known optical methods with potential assistance from vision systems, or location tracking, to direct amounts and optimize timing for this range of electromagnetic radiation.

Figure 29A:
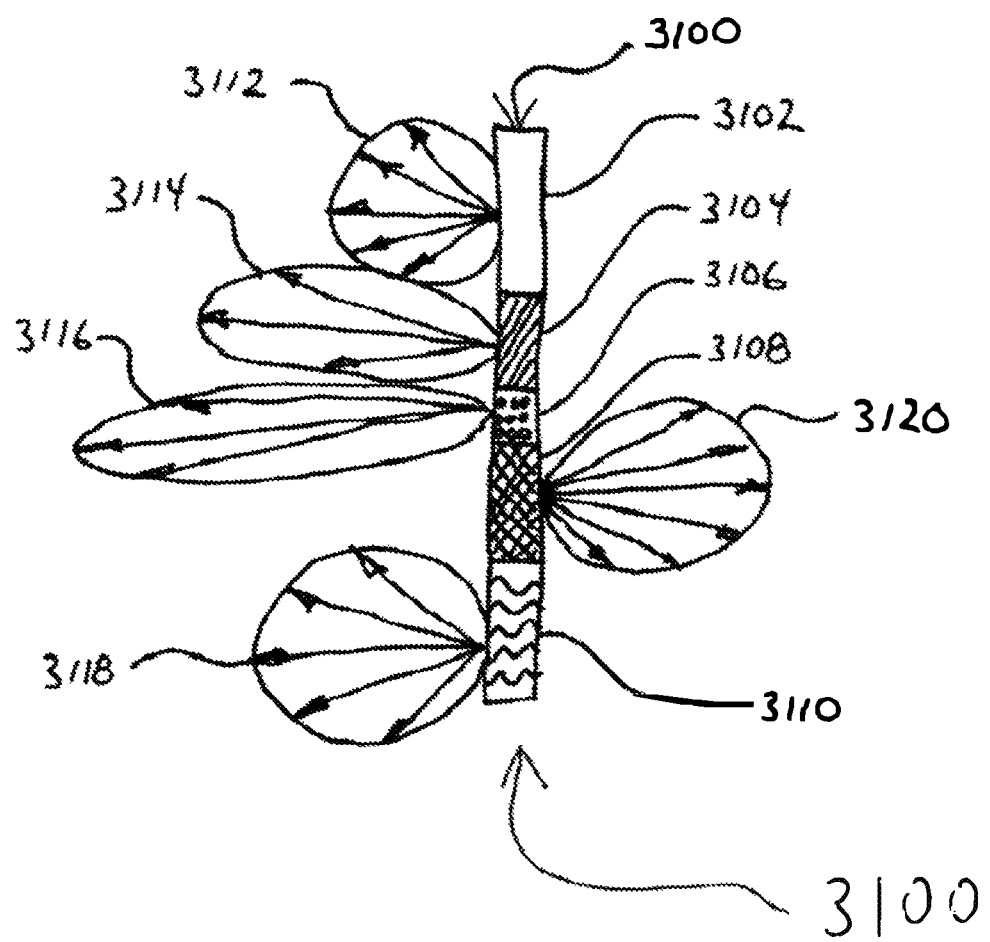
FIG. 29A shows a schematic view of an embodiment according to the invention.
Figure 29B:
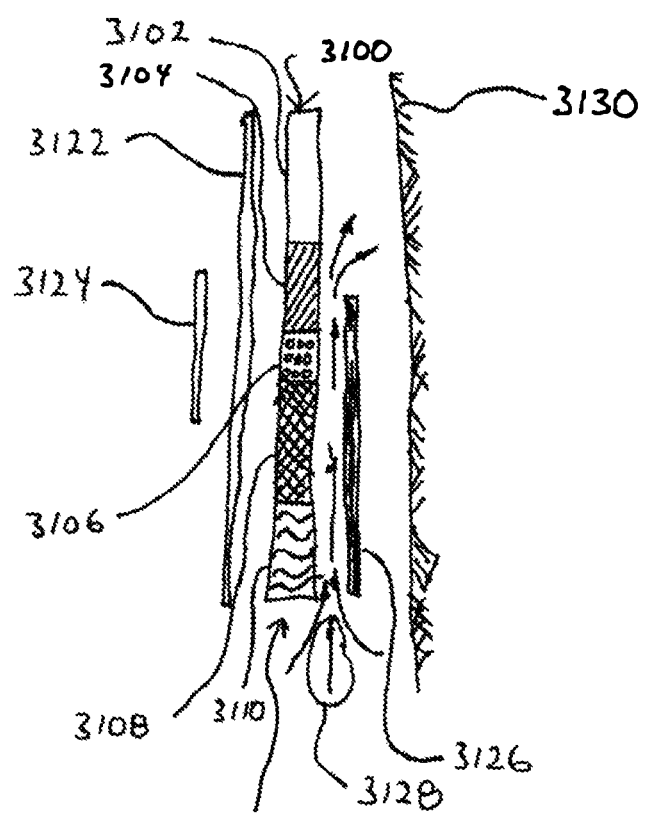
FIG. 29B shows a schematic view of an embodiment according to the invention.
Figure 30:
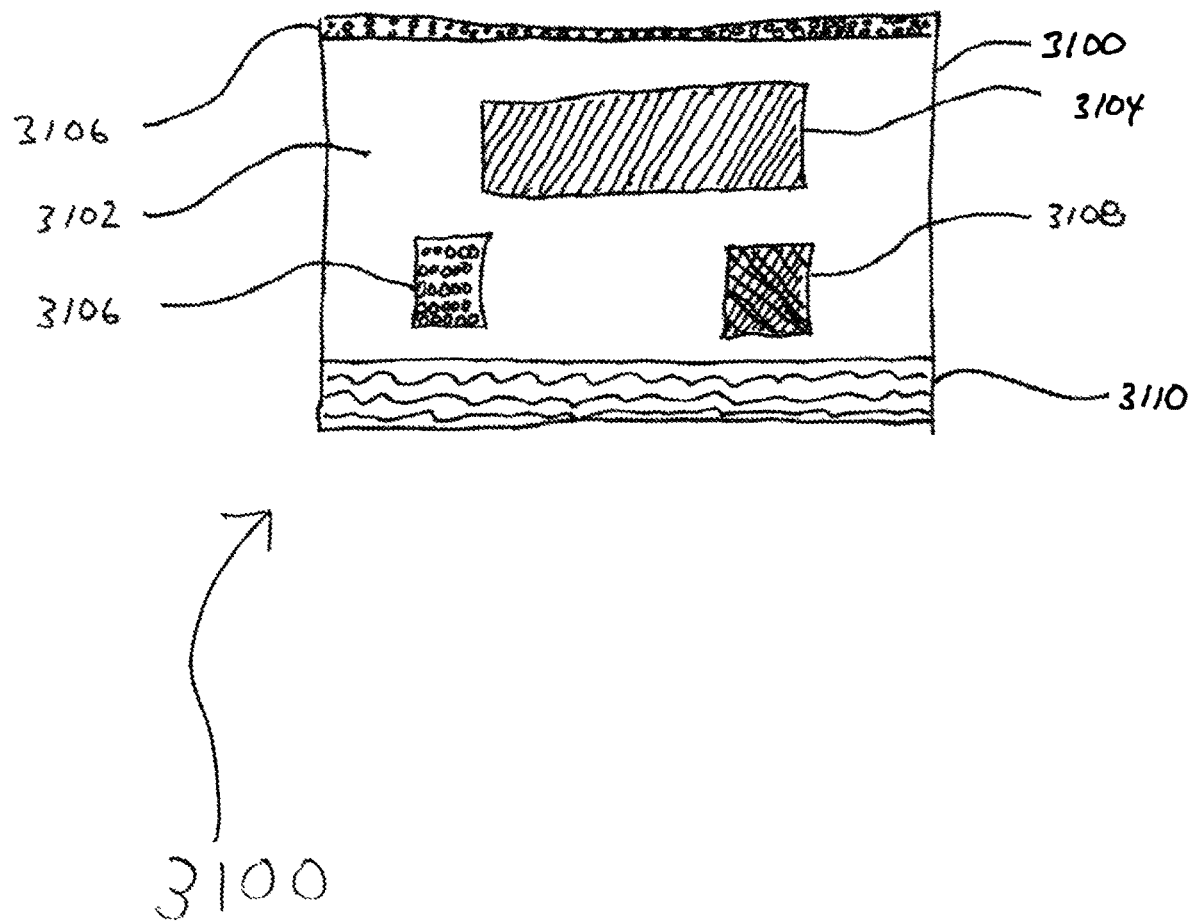
FIG. 30 shows a schematic view of an embodiment according to the invention.

FIGS. 29A, 29B, and 30 show and describe an additional example embodiment of a device 3100 according to the invention. The device 3100 may be configured to provide the full combined range and variety of electromagnetic emission functions and provides an example of a device 3100 that can provide multiple wavelength bands of electromagnetic emission with different defined spatial distribution characteristics supportive of human performance, health and well-being. Device 3100 is intended to provide for at least some of the illumination needs within the visible radiation band from about 380 to 400 nanometers out to about 700 nanometers. This visible light is combined with at least one other radiation wavelength band from either side of the visible wavelength band for nonvisible benefits that can affect human health, performance or wellbeing. Prior art systems are typically purpose-built to support one function such as illumination or, in some recent cases, to support up to two functions such as lighting combined with some disinfection via visible and ultraviolet light combinations existing within a single lighting apparatus. However, these systems are typically more narrowly confined to a form of illumination with some disinfection function and don't disclose the much broader range of functions and distribution parameters that can be provided by a device 3100 according to the invention. For example, in addition to a potential range of visible light wavelengths within device 3100, at least one other range of electromagnetic wavelengths will be provided and precisely controlled within the space. For example, wavelength range 3002 corresponds generally to the ultraviolet wavelength bands which may be emitted but directed outside the range of human exposure and used to provide for more aggressive disinfection or treatment of the air at locations which may be either hidden or internal to device 3002 or otherwise directed to minimize or eliminate the potential for human eye/skin exposure.

One example embodiment as described in FIG. 29B is to harness energy in wavelength band 3002 that is emitted by devices 3108 is via defining a full or partial cavity that is defined between the body of device 3100 and another part 3126 attached and integrated with device 3100 that can define a space for airflow that is outside the normal range of human vision behind, or within, the device 3100. This space could also be defined between the device 3100 and a wall 3130 or optionally another surface 3126 that enables an airflow 3128 to be either naturally convected or driven by other means such as fans that will enable airflow 3128 to be exposed to devices 3108 that can treat the air to reduce viruses, bacteria or other airborne pathogens. By reducing any visual interaction or potential for skin exposure to emission 3120 a satisfactory level of safety can be achieved. Active methods to drive airflow 3128 within device 3100 could also include fans such as electrostatic fans along with internal ducts which direct air flow into internal recesses that are subsequently irradiated by emitters 3108 for disinfection.

Another range of wavelengths that may be emitted by this device 3100 is the range 3006 approximately between 700 nanometers and 1300 nanometers which is typically called the near-infrared ("NIR") range of light which is noted as being potentially helpful for the stimulation of healing, stimulating mitochondria in the ATP cycle and other health benefits. As studies have shown, human exposure to this range of wavelengths 3006 on a regular basis is beneficial in terms of a healthy reduction in resting heart rate, vasodilation, and other health benefits. The range of wavelengths noted in section 3008 between 1300 nm and 3000 nm in the mid infrared range may also optionally be employed for other benefits mitigated by these wavelengths. The range of wavelengths in range 3010 between about 3000 nanometers and 10,000 nanometers and beyond into the range 3012 are notable in that they can be advantageously used to provide radiant heating within a space and more efficiently replace other types of low efficiency heating systems.

One particularly advantageous of an example embodiment of the invention is the joint provision of illumination, and radiative heating via Far Infrared wavelengths for occupants within a space. By combining, for example, visible light for illumination from range 3004 and far infrared emission in the range 3010 and 3012 it is possible to provide two key functions for humans within a space, lighting and personal space heating and may further include antibacterial lighting and/or light therapy using red and/or IR. These wavelengths can be utilized to add the functionality of safe and clean radiative heating to the device 3100 via far infrared sources 3110 emitting radiant energy in bands 3010 and 3012 in a prescribed pattern 3118 enabling it to provide a targeted spatial field of heating radiation which greatly enhances the utility of device 3100 to individuals within the space. In addition to radiative heating and illumination, device 3100 can also provide circadian tuned visible light in range 3004 along with near-IR within range 3006 for a more complete solution for human visual, non-visual and comfort needs. This combined system has the advantage of only requiring a single power feed as opposed to the common present use of multiple devices and systems that run separately within the space. Device 3100 consolidates a range of functions in a single unit which may advantageously utilize a single housing and power supply point thereby offering a smaller embedded energy footprint and a far simpler wiring system.

It is known that space heating (for a typical building) represents about 64% of the total energy use within the building envelope while only about 3% is used for lighting. If the lighting energy use were to borrow energy from the space heating to provide infrared energy (heat) to occupants, then it can also more efficiently reduce the requirements for space heating by "targeting" the individuals with infrared heating emissions while offsetting the space heating requirements that are typically used to heat the atmosphere in the space. Therefore, the net energy requirements of the combined systems lower the energy footprint of the building while providing increased utility to the comfort and health of the occupants within the building. Such a system improves overall efficiency such that the other functions such as therapeutic IR energy could be completely offset by the net saving of energy used to heat the space.

It is known that prior art heating systems that consume fossil fuels and rely on boilers and radiators are usually significantly less efficient and harmful to the environment by virtue of their dependence on non-renewable fossil fuels that are affecting global warming. As the planet warms, the focus on renewable clean electrical energy in the grid can be advantageously utilized in an apparatus and/or device such as device 3100 since it can deliver very high electrical conversion efficiencies beyond many conventional heating systems. Furthermore, it is known that infrared radiant heating of people and objects can permit the air temperatures within the space to be on the order of 2 to 3 degrees Celsius lower than in comparable systems that simply heat all the air, thereby saving even more energy. Individuals in the space are warmed by radiant energy that can be more efficiently directed specifically to areas of use unlike conventional heating systems that typically heat the air for the entire space. Furthermore, such a device 3100 can enable even higher heating efficiencies since it can also make use of location-based data for occupants and selectively target heating from devices in the space that are directed to where individuals are located and automatically switch off in areas where occupancy is nil. Device 3100 may be located on a wall, ceiling, floor, furniture or otherwise disposed within a space inhabited by humans such that its emitting regions are able to deliver at least two or more prescribed electromagnetic distribution functions to the space. This concept of a modular system that is ideally located in the ceiling, walls or other interior surfaces that can provide for both lighting, heating and therapeutic needs is compelling as only one source of power is required to deliver all of these functions. Where focused energy is required the choice of infrared source should have a lower etendue than other sources where the spread of radiation can be maximized. For example, a resistive radiant heating panel with a 2 foot by 2 foot emitting surface for general radiant heating can be advantageously combined with a lower etendue narrowband IR source that is tuned to therapeutic purposes and where its optical system can intelligently and efficiently couple this radiation source to focus on the user in the space via either static placement or via an active optical system or a tuned array.

Device 3100 as shown in FIGS. 29A, 29B, and 30 contains two or more different radiation emitting apparatus that emit radiation into two or more radiation bands within the radiation spectrum 3000 of FIG. 29A along with optional radiation modifying systems such as 3124 for the specific spatial distribution of electromagnetic energy into the area. These are divided into a variety of emitting areas within a device as illustrated in FIG. 30, and may be located side by side, embedded within, or layered on top of each other with a variety of beam shaping and controlling optics tailored to the specific functions desired from the apparatus.

For example, region 3102 of the device 3100 may be defined to be the specific location on device 3100 designed to deliver visible light emission between about 380 nanometers and 700 nanometers to the space to provide visible ambient illumination within wavelength band 3004 for occupants. Visible light electromagnetic energy from light sources associated with surfaces 3102 are shown as having light distribution pattern 3112 which is shown as typically having a wide dispersion as could be advantageous for area illumination. Light distribution patterns 3112 can also be narrower in solid angle than shown or could be broken into two or more asymmetric distributions or angled as required to address glare and to provide the required illumination for occupant tasks within the space. Light distribution pattern 3112 can also be located on or around different locations at the top and the bottom of the device body, or in any convenient location such as a perimeter region or edge region such that the ambient light needs in the space are adequately covered for task illumination used by inhabitants of the space. The etendue of light emission devices associated with regions 3102 are also typically higher as they are typically used for ambient illumination and not required to be highly focused or targeted with precision. Light sources used in region 3102 can be LEDs, multiple LEDs, VCSELs, Super Luminescent Diodes, or other sources know in the art that can either be single type emission or a suitable combination of devices with different emission spectrums that can be combined and controlled electronically to create a composite spectrum of light. Control systems to drive these devices can be adapted as known in the art to control the composite spectrum of light in a temporal fashion.

Area 3104 of the device is a region that also delivers visible light emission between about 380 and nanometers and 700 nanometers in region 3004 to the space for specific and targeted illumination such as for task lighting or spot lighting or highlighting where higher incident illumination is needed. Light distribution pattern 3114 is shown as more narrowly spatially controlled than 3112 and comes from a smaller region of the device 3104 such that it can advantageously leverage a lower etendue and optical system to afford greater precision and control over the emitted light photometric profiles. Light pattern 3114 can be a composite pattern of smaller patterns that can also be dynamically controlled via adaptive optical systems such that a prescribed beam pattern can be controlled. Thus, the combination of light pattern 3112 provided by region 3102 can be combined with pattern 3114 provided by region 3104 to provide for both ambient illumination and higher contrast illumination. Examples of this combination include, for example, the overall background illumination in a space that is used together with a narrower spotlight illumination to target light on specific focal points within the space to bring attention and contrast to these points. As discussed, the spectral content for source region 3102 and 3104 may also be different since the ambient illumination 3112 coming from 3102 may be providing a tunable spectrum that provides for circadian entrainment while 3104 performs a different function that does not require the adaptation of its spectral content. The reverse is also true and depends on the specific targets and requirements for each lighting element within the device 3100.

Region 3106 of device 3100 is for a radiation emitting source that can emit within the near-infrared region 3006 or 3008. It is preferably a solid-state source that has a relatively low etendue such that it can be more effectively directed into a narrower and more targeted emission pattern 3116 such that it can be advantageously aimed directly at a user in the space via either static or dynamic optics. Suitable devices used in this region could include solid state LED or infrared laser devices or other concentrated sources in silicon, semiconductor or other material systems that can provide compact sources of infrared emission. One potential light source for the provision of infrared energy is a vertical cavity surface emitting laser ("VCSEL"), which is a solid-state light emitter that can be arranged as either a single emitter or as a narrow linear or compact spatial array of emitters. For example, the reference (https://iopscience.iop.org/article/10.1088/1674-4926/30/11/114008/pdf) discusses a linear array of 980 nm infrared solid state VCSEL's that can produce up to 880 mW in a Gaussian far-field distribution. Devices such as these emitting into the infrared can also be focused or controlled by variable beam shaping optics such as an addressable liquid crystal matrix lens or other digital optical control mechanisms such as digital micro-mirror devices (DMD) or other tunable optical mechanisms. The optical control mechanism is driven by the spatial data representing the location of a user relative to the array that is used to efficiently deliver the therapeutic light to the regions of interest for the user. For example, an Infrared VCSEL array is an ideal source of narrow band infrared energy that can be efficiently coupled to the treatment areas from either a portable display device, laptop, monitor, television, cubicle divider, furniture, chair, artwork, panel or any other surface within the proximity of a user. Ideally the array of devices such as VCSEL's, LEDs, or other emitters with their associated optics is compact enough to fit within a tiny bezel of the device or even disposed behind or within the display or panel pixels such that its energy can be directed to the user with little transmission loss. The final width of the array could be on the order of less than a few millimeters, or the distribution of individual devices at the pixel scale or smaller could be made to be virtually invisible amongst the display pixels and inobtrusive to the main display such as in areas 3504, 3507, or 3509. VCSEL's are also used in Time of Flight ("TOF") three-dimensional sensing mechanisms and therefore could be used both for telemetry to spatially identify the location of the users and to provide various programmed treatment modes. These devices may be used to both map the location of the needed therapy light radiation and ultimately programmed to deliver the correct dosage to users via vision systems and spatial mapping. Preferred near infrared sources 3106 are compact and readily controlled either statically or dynamically for spatial profile, timing and wavelength selection such that this near infrared radiation source is targeted to the individual needs of the user.

The levels of irradiation needed to be therapeutically meaningful can be calculated by reproducing for example a level of irradiation in the infrared that is comparable to natural daylight. It is known that the integrated intensity of sunlight radiation within the spectral window of 800 to 900 nanometers in the Northern Hemisphere is roughly 90 $W/m^2$. There is suggestion from some clinical studies that an irradiance of at least 50 $W/m^2$ is effective for systemic health benefits within the spectral range of about 850 nanometers. If 50 $W/m^2$ is used as a benchmark irradiance level it is possible to extrapolate the necessary performance of infrared light sources needed to be effective for the illumination of a person's exposed skin of their face in proximity to a display. In this example, if the person's face is roughly 220 mm vertical and 120 mm horizontal in extent then the surface area presented is roughly 0.0264 $m^2$. If a targeted light source were provided that could exactly cover this areal extent then the total radiation needed to hit the person's face would be 50 $W/m^2$*0.0264 $m^2$ which is equal to 1.32 Watts of total incident energy in the region of 850 nanometers. If the etendue of the infrared light sources is low (such as within a VCSEL array) then it would be possible to efficiently direct the source radiation with intelligent optics such that the generation of this energy is actively coupled to the person's face such as by laser steering or via an array based metamaterial optic which can electronically adjust its spatial indices of refraction to steer the light to the target region of the user's face. Alternatively, active reflection arrays such as DMD devices could also be harnessed in devices such as web cameras or within the bezel of the display or in any other convenient and inconspicuous location in proximity to a user's face and upper torso. The preferred embodiments of this technology would efficiently direct radiation to the exposed skin surfaces without allowing wasted energy to miss the target, even as it changes location within a region in front of the device. If this energy is efficiently coupled from an infrared device with an overall quantum efficiency of about 50% then it would be possible to provide the equivalent radiation concentration to a person's face from as little as 2.64 Watts of input energy to the devices. This implies that even a portable tablet device, handheld device or USB powered camera or accessory would be easily capable of supporting this level of power to create an irradiance source suitable for therapeutically effectiveness. These devices would efficiently paint the user's face with the therapeutic radiation and would actively adapt as the user moves such that the location and dose of radiation can be accurately directed and monitored. As the etendue of the infrared light sources increases, and the ability to focus and steer the energy becomes more challenging, it may be necessary in some embodiments to design the emitting array to provide higher input levels of energy such as 2× to 10× more to account for energy that spills outside the target region and misses the user's exposed skin surfaces. However, these less efficient coupling designs may also be advantageous as they may not require the complexity of steerable optics or low etendue laser sources and may be well suited to mains powered devices such as video displays which can make use of infrared LEDs or other semiconductor sources that are aimed at a broader spatial region where a person is present.

FIG. 30 shows that regions of device 3100 that can be used for infrared radiation source 3106 can be located both within the overall space defined by 3100 or alternatively at another location such as at the top of the body of 3100. This latter region could correspond to the upper bezel, or a narrow emitting region of less than 3 mm located within the perimeter of a display (including but not limited to the displays as described in FIGS. 16 through 21), for example, without affecting the geometry and the viewability of a display. With some displays, or panels, region 3106 could also be located behind the display or embedded within the display such that their infrared emissions pass through the display to the user. Materials that are transparent to infrared are well known for this purpose and their deployment would not be visible to the user as the emission of infrared would not be within the visible range for humans. For example, this location as shown in FIG. 30 may be ideally suited to exposing the specific locations of a user's face to the directed infrared radiation patterns 3116 in wavelength regions 3006 and 3008 that can potentially provide medical or health benefits to the user. Furthermore, as displays move from liquid crystal with an LED backlight to direct emission micro LEDS or nano LEDS it is contemplated that some pixels or groups of pixels can include micro or nano infrared devices that can exist within the direct emission display grid with optical systems that can direct their radiation preferentially towards a user viewing the display. According to the inventors, a person viewing or facing a video display device and/or electronic video display device means having a direct view of and/or facing the portion of a video display device that is configured to provide video images and not the back or bottom of a video display device where a person would not spend as much time viewing. These small devices can be controlled alongside the visible light devices such that the display driver is also driving the therapeutic light dosing with optional feedback from sensors or cameras while simultaneously driving the display and potentially also controlling the chromatic mix of visible light emitting devices such that they are also providing the necessary circadian entrainment by modulating wavelengths such as around 490 nanometers. These light sources could be natively focused, or via intervening optics, have their output focused such that a dynamic optical system can advantageously direct the therapeutic light in the correct amounts to a dynamic spatial pattern of the users skin, eyes and other body parts based upon a pre-determined therapeutic regimen determined by one or more of time, radiation, spatial dosage or change in therapeutic bio marker such as blood chemistry or other factors. The advantage of this display or panel device 3100 is that it incorporates both the image generation with circadian entrainment along with the potential for therapeutic provision of near-infrared with intelligent controls and feedback which ensures that the user in front of the display is being "fed" healthy constituents of light while they are working in front of this device. Such a "healthy display" as disclosed in FIG. 30 would then intelligently incorporate at least three functions for a user.

A fourth function could also be included in device 3100 as disclosed earlier where a portion of the display includes the use of devices 3108 that operate in the region 3002 that can be in a non-visual area of the display to provide advantages related to the elimination of viruses or bacteria in the vicinity of the display.

Optically active materials or passive materials 3122 or 3124 may be employed over device 3100 to homogenize, focus, or act on specific optical properties of the various emission patterns. For example, element 3124 may be a tunable optical material such as a radiation transmitting meta material like liquid crystal under the control of an electric field that actively changes the index of refraction and its gradients under electronic control. These systems, such as demonstrated by LensVector Inc., have been successfully demonstrated to be capable of adjusting the beam pattern of electromagnetic radiation, or for beam shaping and steering, and can enable the optical system to respond to sensing or spatial data to actively adjust the radiation distribution, aiming and timing of delivery for electromagnetic energy. These active optical systems can be employed with a group, or an array, of radiation emitting devices 3106 under the combined control of a system with a camera or other sensor providing targeting information, such as a range finder employing time of flight, to direct and control the intensity of the radiation in a variable pattern 3116 from the regions 3106 of the device 3100 for example, so that it is targeting the regions of a user's face, or body, or wherever the maximum benefit is obtained.

Another useful embodiment of one or more of the display devices according to the inventions described herein is that they can also intelligently deliver radiation either when the eyelid is open or when it is closed. It is known that most people blink about 15 to 20 times each minute and that the typical person blinks about 10% of the time that they are awake (from www.healthline.com/health/how-many-times-do-you-blink-a-day#blinking-frequency). Since the human eye is closed for roughly 10% of the time, this cycle can thus be advantageously used to synchronize the application of optical radiation for therapeutic purposes where either radiation is applied while the eyelid is open or closed. The potential to vary the time of delivery of visible or invisible radiation, or light, can be both useful to save energy but also to increase the efficacy of the delivery system when exposures to certain radiation bands may be desired, or need to be avoided, via the optical pathway into the eyes or other tissue.

Figure 31B:
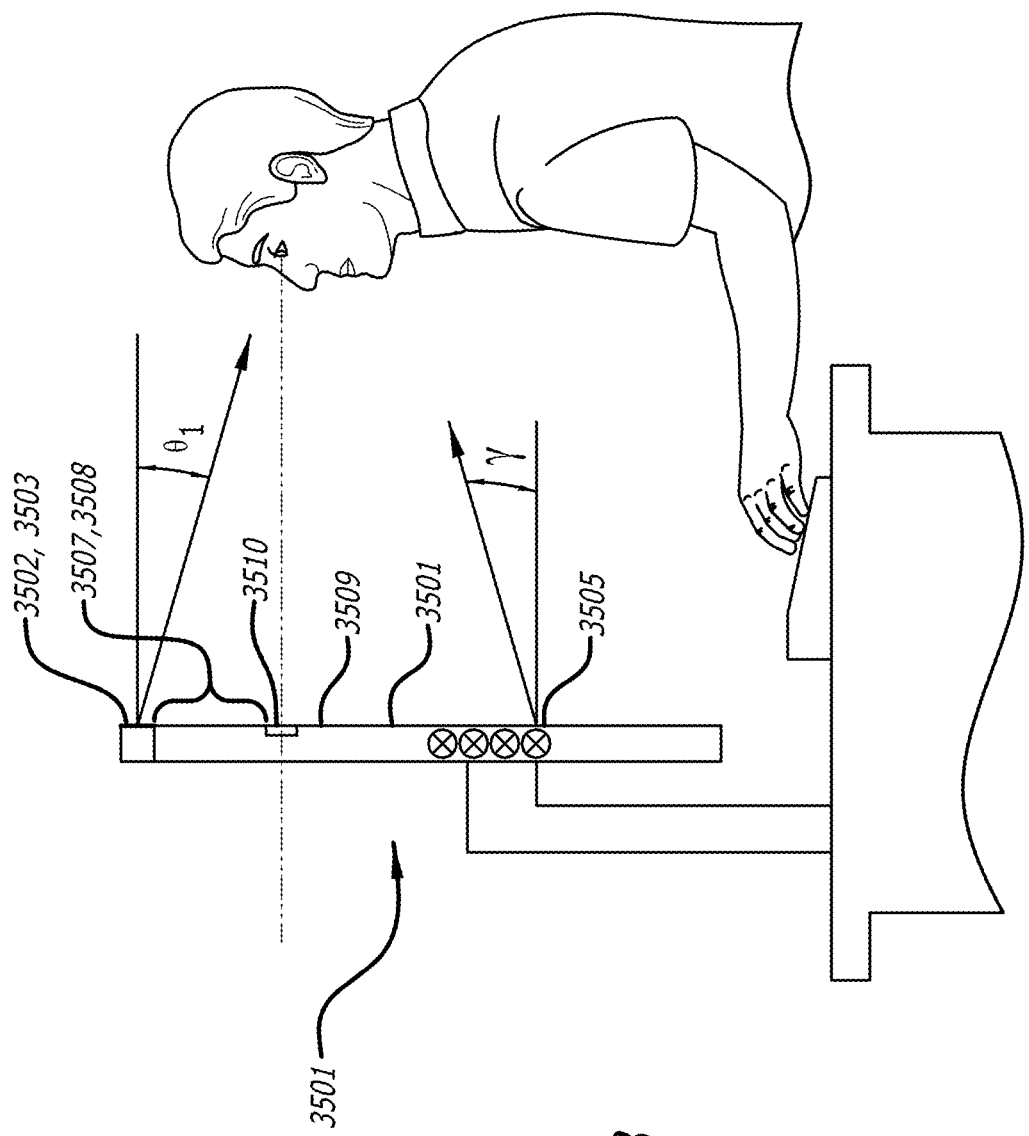
FIG. 31B shows a schematic view of an embodiment according to the invention.

FIG. 31A and FIG. 31B further describe example embodiments of a display device 3501 according to the invention which may include one or more of the features of the devices described herein including but not limited to devices described in FIGS. 15 through 21. FIG. 35A provides an example embodiment with additional advantages of the invention used within a monitor, video panel, television or other device placed in a direct line of sight of a user in a typical seated or standing office environment. While this is characteristically drawn as a planar rectangle, other shapes, including curved, rounded or any other shape that presents an active surface that varies from a planar surface in one, two or more axes, including curved, spherical or freeform could be enabled by this invention. The monitor, panel or surface, 3501 is preferably able to deliver a video or still image, or illumination while also delivering electromagnetic radiation in one, or more, wavelength bands that have a biological benefit to the user. Some of this biological, or therapeutic, radiation may be in the visible range and some of this radiation may be outside the visible range. In one embodiment, if some of this therapeutic radiation is within the visible range of the user, it may be advantageously blended with the overall video signal such that it is a metameric match, or close metameric match, to the desired overall video or still image. Via a metameric match, the presence of these wavelengths is visibly hard to detect from the user's experience, or its sufficiently diminished such that it does not overly distract from the video or images presented. For example, if the addition of wavelengths in the 490 nanometer region of the spectrum (cyan) is desired then it could be blended and offset by the other wavelength sources such that the overall color appearance of the image is maintained and the visual effect of adding power at this wavelength is potentially undetectable by the user. It is known that the peak location for the widest spectral tuning flexibility is found near the Plankian locus between about 3300 and 4700 K within a small Duv range off the locus. Therefore a preferred location for spectral tuning for either illumination or video display output should fall somewhere in this range to potentially maximize the ability to create a therapeutic metameric matching function for the presented still or video image, or for the overall lighting emission.

This device 3501 can also be optionally operated in a purely therapeutic mode without presenting any video information to the user wherein all, or part of the device, is operated to provide therapeutic radiation. Device 3501 can also be operated in a combined mode where video information is presented for part of the device surface and therapeutic radiation is presented from a sub-region of the device such as an upper window or other surface region of the device which is oriented at the correct angle to the user. This embodiment in FIGS. 31A and 31B also illustrates an important consideration related to the correct angular placement of certain radiation, such as circadian rhythm active wavelengths of light, red, NIR, MIR, FIR, and/or infrared, or other bands that are normally present in natural outdoor environments. For example, it is known that the preferred spatial location of circadian active radiation wavelengths for individuals is best received by the eye and delivered to the retinal ganglion cells from a region that is roughly defined as being between the horizontal of an individual's gaze and up to about 45 degrees between the horizon and a vertical axis. This preferred region is noted in FIG. 31B for illuminants 3502 and 3503 which are directed in this downward range by an angle theta one ($\theta_1$). This also reinforces the desirability for these particular wavelength emitting radiation sources to be preferably located in the upper bezel, trim, or within an upper emitting area of the display panel such as the upper central region noted as 3507 such that light emitting elements contained within the display area and noted as light emitting elements 3508 can also emit into a preferred angular range for the user to provide the optimum benefit of circadian radiation or other wavelengths such as infrared. Furthermore, radiation emitting elements 3502 can provide one wavelength range for a particular biological purpose and may extend across a wider range of the upper bezel or region of the display or panel, while radiation emitting elements 3503, or 3508 within the display area may be in different wavelength ranges for different biological purposes and emit from a narrower region of the upper bezel and/or display defined by the area 3504 or within the region 3507. These different types of radiation emitting sources therefore can provide up to two, or more, wavelength regions and be tailored to at least one or more different spatial distributions that are advantageously aimed, or positioned, to provide the optimum efficacy of biological benefits to a user via their locations and angular distributions. The timing, intensity and control of these various wavelength emitting sources may also be directed by spatial proximity of the user, time of exposure, or via biodata of the user obtained from wearable devices, telemetry or other data sources that enables individualized therapeutic benefits. Furthermore, radiation emitting elements 3508 that are within the human visible range and contained within the display or image area would be ideally blended into the display via a metameric match as described above, or if they are outside the normal visual range, they would be blended in optically so that the overall display image is not impacted by their spatial presence.

An alternative embodiment of this concept is illustrated in region 3507 of the display which is shown as inhabiting a region in the upper central area of the display or panel 3501. Light emitting elements 3508 are distributed in this region along with image display emitting elements such that their presence is masked and virtually invisible to the viewer. As they are selectively energized alongside the image display elements, they are either directionally invisible or spectrally invisible by virtue of their relative size and spatial distribution so that they can deliver therapeutic radiation to the user. Their location within the upper region of the display is designed to provide the right angle of entry to the eyes or tissues for therapeutic radiation. As known in the literature these angles are preferred for certain wavelengths of light that are received by interior regions of the eyes which govern human circadian patterns for example. Other wavelength ranges may have other spatial locations that are preferred for incident radiation, and these may be located in other locations such as illustrated within the display in region 3509 or within the perimeter of the display such as illustrated for devices 3505 or 3506 which are located on either side of the display. Devices 3505 and 3506 may also be located within a region of the display near the sides of the display and their wavelength and functions can be different from those of devices 3502 and 3503 located at the top of the display. For example, devices 3505 are shown as having an angle γ upwards from the horizontal plane towards the seated person. This direction may for example be ideal for the delivery of red and/or near infrared radiation to the individual as the efficacy of delivery to the eyes, skin of the face, neck and upper torso is good from this location. Two different bands of infrared or other wavelengths could also be combined in both intensity and timing from sources 3505 and 3506. Thus a single video panel or display 3501 can embody between one and several different wavelength emitting sources at different dispersion angles for intensity and at different incident angles to the user such that it can provide a variety of health benefits which can be modulated by wearable biosensors, video feedback and other methods of telemetry.

The device 3501 and other display devices as described herein may further be configured to provide a specific emission of one or more electromagnetic wavelengths at a specific time of day such as between the hours of 8 am to 9 am every day or every other day, and/or for specific periods of time in minutes such as for 2-3 minutes, or for hours a day. Studies show (www.medicalnewstoday.com/articles/vision-loss#summary) that mitochondria cells follow the body's circadian rhythm and tend to be most responsive to light and/or light therapy such as PBM treatments in the morning. Therefor some embodiments according to the invention may be configured to include the ability to provide similar treatments from a display devices described herein and to emit red and/or IR (NIR, MIR, and/or FIR) at specific times of day such as before 12 noon or at a more narrowed time of day such as between 6 am or 7 am to 9 am, and in some cases depending on the sleep habits of a person the emissions may need to occur at completely different times of day such as after 12 noon or specifically at 6 pm 7 pm to 9 pm, or even when someone is actually asleep at different levels of sleep including but not limited to in a rapid eye movement ("REM") state of sleep. It is contemplated by the inventors that the emissions of such electromagnetic energy and/or wavelengths may provide further enhanced benefits to certain people by modulating and/or pulsing the energy levels and/or durations of emission in response to certain biofeedback information. One such example may be to provide a specifically controlled modulation and/or pulsing of such emissions in response to one or more of the rate of REM, blood pressure, blood oxygen levels, nitric oxide levels, sugar and/or insulin levels, temperature levels, physical position of one of more body parts of a person, or any other measurable biological information that could be provided to a device according to the invention. A wearable display according to the invention may further be configured to provide such emissions from one or both the display emission area visible by a person and/or to the temple region of a person's head.

It is contemplated but the inventors that certain display embodiments according to the invention may be portable, stationary and/or embedded displays used in any environment including but not limited to displays used in and/or for work, school, wearable devices, entertainment, and/or transportation vehicles used on water, land and/or in the air.

Another advantage of the embodiment illustrated within a region 3509 of the display or panel is that it can also contain a central miniature camera 3510 which is located ideally at a location which is conveniently placed to coordinate with roughly the central location of a video window or the display. Prior art systems that perform this function often have a small external camera with external wire that uses a suction device to be placed in the central region of the display, or is hung over the bezel, such that the camera is located approximately at a point that corresponds closely to the image of the other person on the screen. In this manner the camera is then aimed such that there is a reinforcement of eye contact between the person viewing the screen. Other prior art camera systems attach or clip to the upper bezel region of the display, but they don't provide the preferred direct eye contact feature as they are located above the video image which gives the impression that the viewer is looking over the head of the person on the video feed. However, unlike prior art systems this embodiment utilizes a micro camera array or miniature camera that is embedded into the display and partly hidden from view within the display such that it is virtually invisible to the viewer. Ideally the optical path for the camera is unobstructed through the direct display elements such that it has a clear view of the user and their surrounding area. When they select the video function within the display the software determines where the central face and eye location for the remote person is located and then places this roughly at the center of camera location within the display. As the user looks at this video image their eyes will be ideally trained on the location between eyes of the remote person, such that they will appear to be looking directly into their eyes. This invention establishes a more natural eye to eye contact for the virtual connection without wires or bulky cameras located at the periphery of the display via embedding of the camera system within the display. This may also use software to stabilize the image and/or ensure that the video feed aligns such that the appearance of eye-to-eye contact is sustained through the video connection.

Figure 32A:
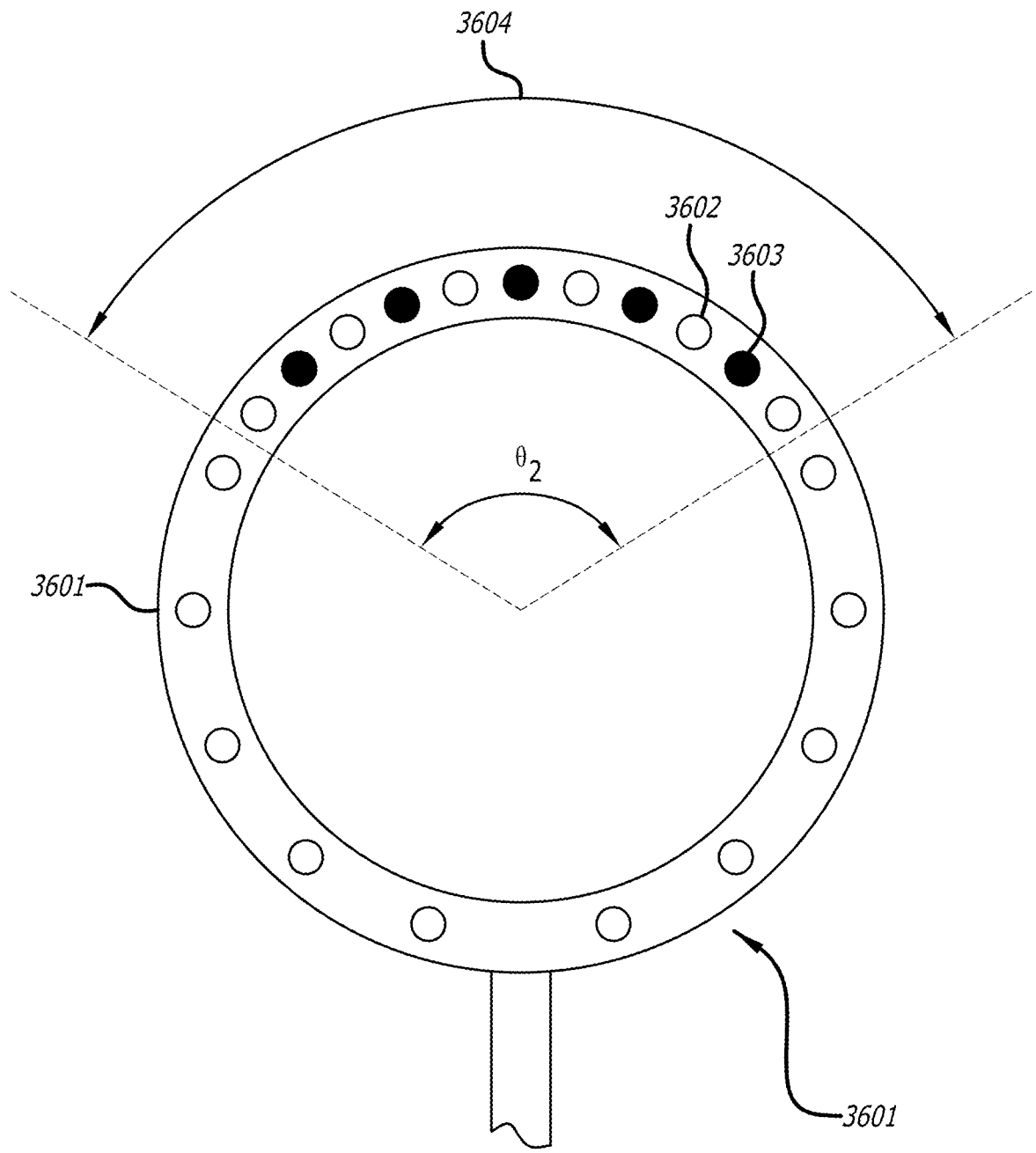
FIG. 32A shows a schematic view of an embodiment according to the invention.
Figure 32B:
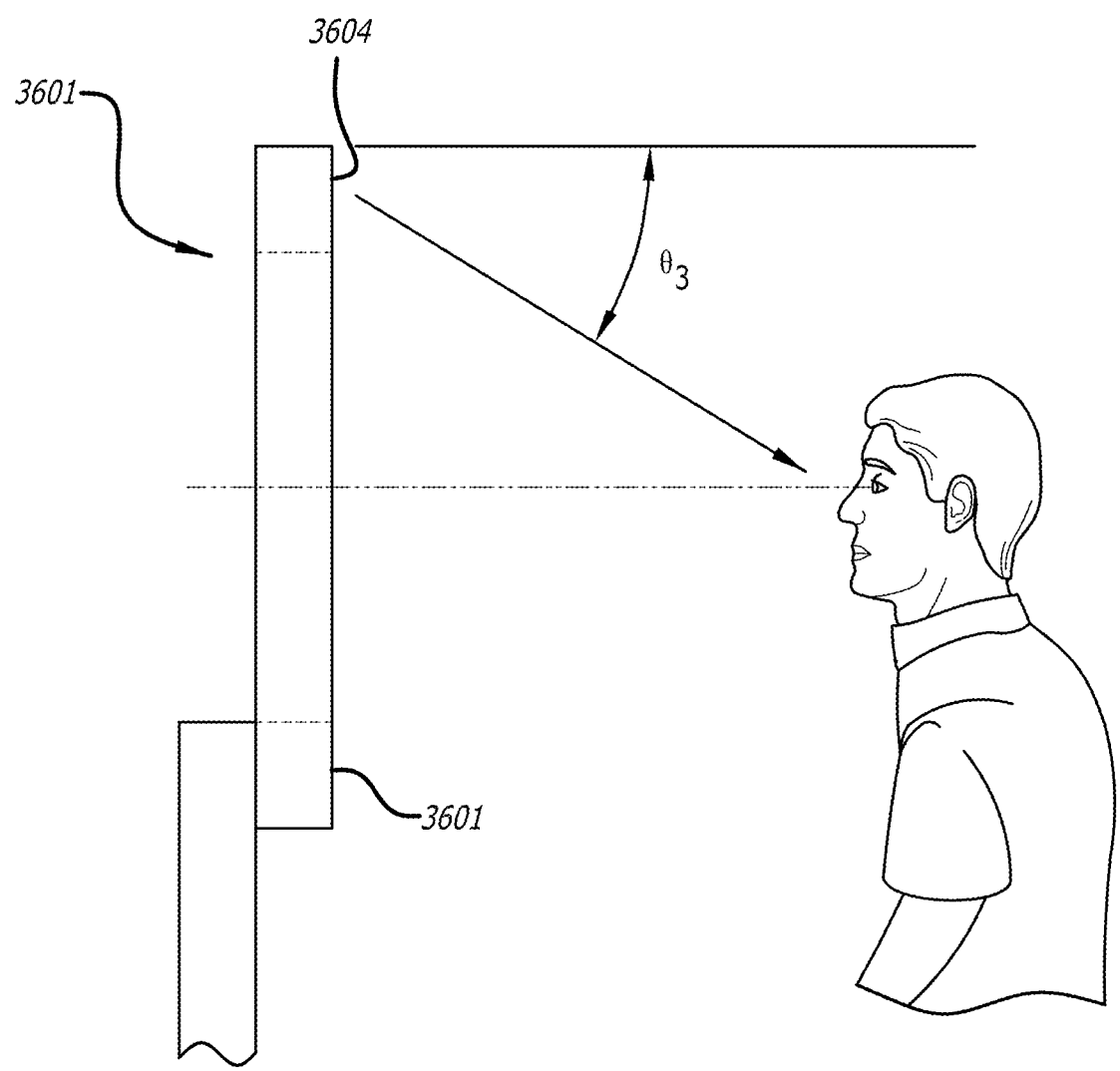
FIG. 32B shows a schematic view of an embodiment according to the invention.

FIGS. 31A and 32B provide another example embodiment of a device 3601 according to the invention with the potential for its use within a ring or modeling light device 3601 used for video streaming or video calling in the proximity of the user. The use of circular ring lights for social media and video-based communications is common due to their unique quality of illumination. These lights are typically placed in proximity to a user where the user's horizontal eyeline as shown in FIG. 32B is roughly coincident with the central axis of the ring light so that their image as obtained by the camera is evenly illuminated. This improved embodiment utilizes the arrays of LEDs with other solid-state sources (LEDs, VCSELS, semiconductor lasers, microLeds, nanoLeds, silicon emitters, etc.) with at least two distinct optical radiation patterns. One is a variable optical pattern for the "modeling" light used to illuminate the individual for the camera image illumination which can be adjusted to provide gradients of light across the face that soften or sharpen the image or add colored highlights such as variable color shadows and other effects. This range of illumination can be provided by the elements 3602 which can be multichip semiconductor sources with optional integrated optics that can be static or dynamically tuned and that are arrayed around the periphery of the ring light 3601. Each of the elements 3602 can be individually tuned light sources which can be collectively or individually controlled to create a uniform pattern of light, or a variable pattern as may be desired by the individual. Elements 3603 are other light emitting elements which can provide specific therapeutic wavelengths of light within a region noted as 3604. For example, this region may correspond to a region above the viewer's horizontal viewpoint as noted by angle $\theta_3$ such that it can be used to provide the circadian effective radiation within the preferred region of a person's vision. The other optical pattern is specifically directed to the prescribed therapeutic radiation pattern which is provided by elements 3603. The use of active optical systems with video feedback and optionally sensor feedback or biodata from wearables can be used to control the variety and timing of radiation patterns to benefit the user. Available biodata includes blood chemistry, pulse rate, blood pressure, glucose, hormone levels, or other markers that are incorporated into either wearable devices, implants or remote monitoring devices.

Figure 33A:
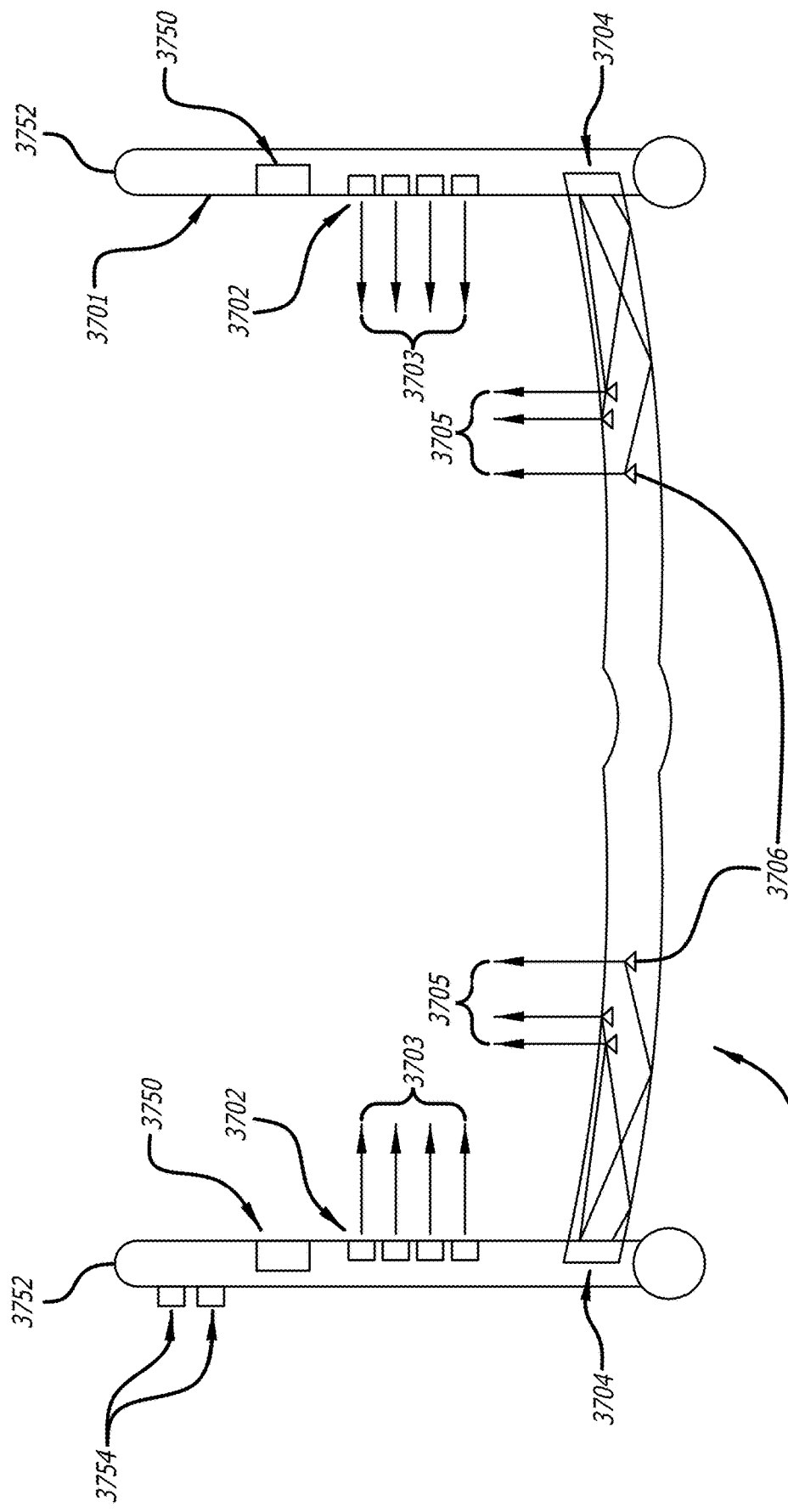
FIG. 33A shows a schematic view of an embodiment according to the invention.

Another example embodiment according to the invention is an eyewear device 3701 as shown and described in FIGS. 33A and 33B which is specifically designed to add therapeutic functionality to eyewear, which may be configured to include but not be limited to eyewear that includes electronic visual display features and/or "smart" eyewear or may be configured to be therapeutic treatment eyewear that is configured to emit one or more of the electromagnetic wavelengths described herein including but not limited to the wavelengths described herein in device 1100 in FIG. 15 and and/or in the device 2500 in FIG. 27, or other devices described in FIGS. 1-27A described herein using the various methods of control of the wavelength emissions as described herein. Eyewear device 3701 may further include one or more of an audio output device 3750 which integrated within the body of an arm 3752 of the eyewear device 3701. The audio output device 3750 may be configured to be miniature audio speakers including but not limited to those speakers known in the art as bone conduction speakers. Eyewear device 3701 may be configured to be designed to closely resemble the appearance of standard sunglasses, corrective eyeglasses, wearable displays, or other eyewear and/or facemasks with the addition of one or more modes of therapeutic functionality that may be optionally delivered to the user as needed in automatic and/or user controlled configurations with the user being someone that includes a person that is a user of the device or a therapeutic and/or medical practitioner of a person requiring treatment with such a device. This therapeutic functionality can either stand alone, or it can be delivered along with either augmented, mixed, or full virtual reality delivered to the user's eyes via known micro-displays, waveguides and/or other retinal imaging methods. Both visible red, NIR, and/or MIR and FIR light and/or wavelengths required for therapeutic purposes can be generated in one or more locations, which may be direct line of sight such as from the lens media 3708 which may be configured to be non-transparent, transparent and/or partially transparent lens media 3708, and/or within a remote location to the eye within the eyewear device 3701, such as in the hinge region 3704, frame or other structural region of the eyewear device 3701. If eyewear device 3701 does generate the light and/or wavelengths in a remote location to the lens media 3708 and lens media 3708 is transparent and/or partially transparent, the light and/or wavelengths would then be coupled and guided through the transparent lens media 3708 until it reaches optical re-direction elements 3706 which can turn the light towards the region of the user's eyes as shown by rays 3705. These re-direction elements 3706 can be created via electric fields acting on liquid crystal or embedded microelements etched within the lens material. Since rays 3705 can be advantageously coupled near the center of vision it can effectively illuminate the retina with either circadian active visible light including but not limited to within the range of 630 nm to 680 nm, near-infrared including but not limited to within the range of 730 nm to 780 nm, and/or far infrared light, or any other wavelengths described herein including but not limited to those that have been shown via photobiomodulation to restore the function of damaged mitochondria in the eyes and prevent cell death to preserve vision (from www.nature.com/articles/s41598-020-77290-w). At least a portion or all of the lens media 3708 may further be made of graphene and stimulated with pulsed visible and/or non-visible light to cause the lens media 3708 to emit FIR energy towards the eye. Eyewear device 3701 may further be configured to include one or more of one or a combination of a rechargeable battery which may be a flexible or non-flexible battery, an input for battery charging and/or connection of a remote power source, a controller IC, an audio speaker, a microphone, a wireless transceiver, a retinal scanner and/or a camera. Eyewear device 3701 may further be configured to be physically connected to second electronic device 3701B which may include but not be limited to any one or more of a PC, a medical device, a lighting device, a smart wearable device and/or and portable communications device, which such electronic device 3701B may be configured to include one or more of the features and functions of the devices described in the device figures herein including but not limited to the devices described in FIGS. 1 through 32B. The device 3701 may be configured to be in wired and/or wireless connectivity and/or communications with electronic device 3701B to receive power and/or data via wire or wireless transmission, including but not limited to health and/or biological data of a user, control signals or other transferable data available that can be made available from the electronic device 3701B. The device 3701 and/or the electronic device 3701B may be configured to include sensors including sensors including but not be limited to sensors capable of sensing one or more of temperature including but not limited to ambient or body temperature, electrical signals including but not limited to a person's electrical signals, the infrared emissions of a person, humidity, blood, blood pressure, blood oxy gen levels, microorganisms, organisms, biofeedback, bio-resonance, vitamin levels including but not limited to vitamin D, proximity and/or location of a person and/or device including but not limited to an electronic device, oxygen, enzymes, fluids and/or minerals. The device 3701 may be configured to include one or more user accessible control buttons and/or switches that would be used for various reasons know % in the art of electronic devices including but not limited to switches configured to select a preset therapeutic treatment of the electromagnetic emissions, establish communication connectivity to other devices such as electronic device 3701B, volume levels and/or play through or play next of audio output selections from the audio device 3750.

Photochromic lenses are eyeglass lenses that are clear (or nearly clear) indoors and darken automatically when exposed to sunlight. Other terms sometimes used for photochromic lenses include "light-adaptive lenses," "light intelligent" and "variable tint lenses". The molecules within the photochromic lenses react to UV and some forms of visible light. It is further contemplated by the inventors that lens media 3708 may further be configured to be photochromic and react to one or more wavelengths of electromagnetic emission, including but not limited to UV and/or near UV emissions that may be intentionally and/or unintentionally induced into the lens media 3708 from within the device 3701, or from external sources of electromagnetic wavelength emissions including but not limited to the sun, or artificial light from other sources and that the photochromic properties of the lens media 3708 may be designed to be advanced such that when the lens media 3708 goes into a darker photochromic state, that emissions of therapeutic wavelengths from the eyewear device 3701 could be initiated in response to a sensor sensing the photochromic properties and/or photochromic state of the lens media 3708. The eyewear device 3701 may be configured to emit a level of UV and/or near-UV light emissions in a selectable and or controlled level into the lens media 3708 such that it does not allow any, or a limited level of UV and/or near-UV to be redirected back into the eyes of a person wearing the eyewear device 3701, and allow the person to control the lens media 3708 in its level of darkness and/or clarity to a level that may be desired but the user and/or person wearing the eyewear device 3701. It is further contemplated by the inventors that eyewear device 3701 may further be configured to include the display features within the lens media 3708 such that the display provides video images when the eyewear device 3701 receives data from the electronic device 3701B. The entire portion of the lens media 3708 may be configured to display video images, or only a percentage (more or less than 50% such as 75% for example) of the lens media 3708 may be configured to display video images while the remaining percentage (25% for example) of the lens media 3708 may be configured to emit therapeutic wavelengths such as one or more of red, NIR, and/or IR towards the eyes of a person and/or user wearing the eyewear device 3701.

According to the invention of the eyewear device 3701 described herein, it is further contemplated by the inventors that another embodiment of the eyewear device 3701 may be configured to provide the ability to emit and induce only a desired level of UV into the lens media 3708 solely for the purposes of controlling and/or setting the photochromic molecules of the lens media 3708 to a desired level and or state of photochromic response when the eyewear device 3701 is worn and/or used indoors or other locations where there are limited UV emissions and a person and/or user of the eyewear desires the darker lenses on their glasses, thereby providing electronically tunable and/or controllable photochromic lenses for various forms of eyewear including the ones described herein. Micro-LEDs and/or nano-LEDs may be integrated into the eyewear device in a location such as the frame such that the LEDs emit focused UV and/or near UV emissions (or other wavelengths that can cause the photochromic molecules to react) into the edges of the lens media 3708, or wash across the surface of the lens media 3708 in such that a substantial portion or any of the UV and/or near UV emissions do not reach eyes of a person wearing the eyewear device 3701 and still cause the lens media 3708 to be tunable and/or controllable in its level of photochromic response. It is further contemplated by the inventors that micro-optics and/or micro-reflectors could be included in a portion of the eyewear device 3701 to allow certain desired wavelengths to be visible to the human eye of the user, and other non-desirable wavelengths to be reflected away and/or block from the vision of the person wearing the eyewear device 3701.

FIGS. 33A and 33B also illustrate another useful function that could be added to the arm portions 3752 of the eyewear device 3701 using elements 3702. Elements 3702 are electromagnetic energy emitting devices and/or elements, such as solid-state emitting devices including visible, ultraviolet or infrared LEDs or laser diodes. Alternatively, these elements could be optical devices that act as re-direction locations for guided infrared energy that is injected into and waveguided within the arms of the eyewear and turned perpendicular to the axis of the eyewear arm to produce electromagnetic energy beams 3703. The eyewear would then have an integrated and/or remote element as known in the art with controllers, software power supply, emitters and a waveguide that couples this energy into, or through, the frame of the eyewear to the locations 3702 where it is re-directed transcranially. An alternative approach could use electromagnetic energy in one range and at locations 3702 a wavelength converting material can be used to create energy 3703 in a different band. Materials such as phosphors or Quantum Dots known in the industry can perform these types of conversions and could be advantageously employed to convert energy closer to the point of use. This energy 3703 could be in various regions of the electromagnetic spectrum but would preferably be in the infrared and could be coupled transcranially into a person's head where it can penetrate to provide therapeutic photobiomodulation. For example, infrared radiation transmitting through the head at this location has been shown to provide safe therapeutic benefits such as improved cerebral blood flow and positive cognitive improvements in patients with PTSD, depression, dementia or traumatic brain injury.

Figure 33C:
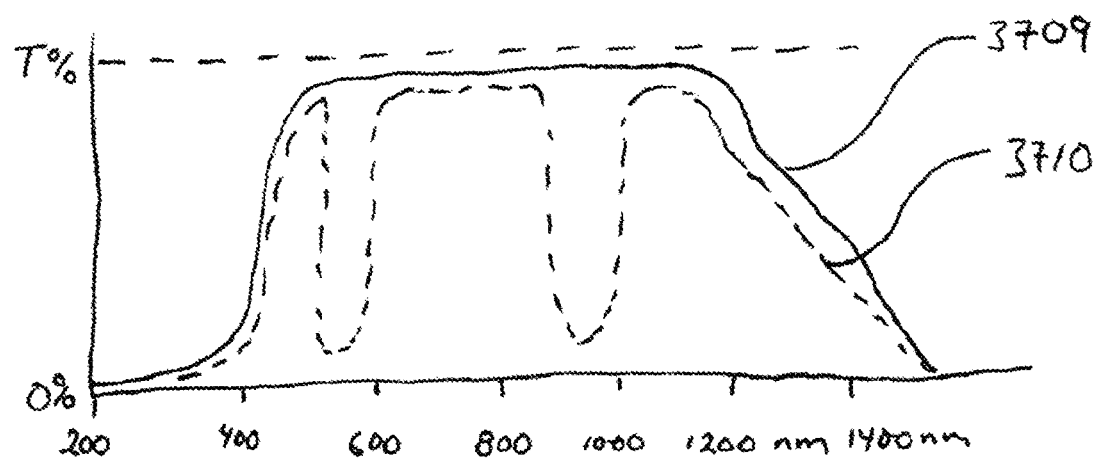
FIG. 33C shows a schematic view of an embodiment according to the invention.
Figure 33D:
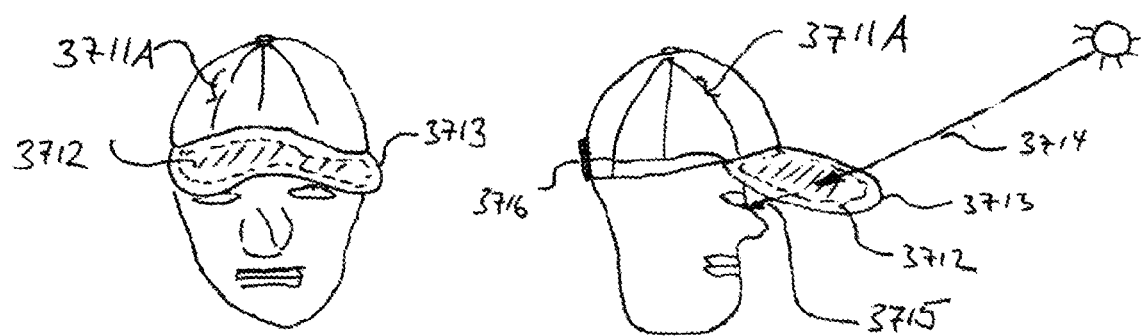
FIG. 33D shows a schematic view of an embodiment according to the invention.

FIG. 33C is an illustration of a spectral transmission curve for a transmitting material 3712 employed in a device 3711 according to another embodiment of an invention (device 3711). The device 3711 includes the transmitting material 3712 in at least a portion of the device 3711 at a specific location of the device 3711. An example embodiment of the device may be configured as a baseball cap 3711A as shown in FIG. 33D having a brim 3713 with the material 3712 being configured to have a specific baseline spectral transmission curve such as the example baseline spectral transmission curve 3709. This embodiment includes a transmission curve 3709 with a relatively high transmission through the visible range of the spectrum from of about 375 nanometers and into the near infrared region below about 1400 nanometers. Other ranges and values of spectral transmission could be just as effective for certain purposes depending upon the desired variations in transmission required. Transmission curve 3710 illustrates an example of how a portion of the spectral transmission can be selectively filtered at one or more locations within the original spectral transmission curve. Materials that can have their transmission properties controlled by electrical fields, temperature, light, or other means such as liquid crystal, phase change materials, or other electronically controlled light transmitting materials, or photochromic lens materials can be used to selectively modify the overall transmission curve and potentially act as selective spectral filters in such a device 3711. This selective filtering can either reflect, convert or absorb certain wavelengths preventing specific wavelengths from passing through the filter 3712.

FIG. 33D shows an application of such a material 3712 employed for example in the brim 3713 of a baseball cap 3711A which could be configured to have the material 3712 allow for specific wavelengths of solar radiation to not only pass through the material 3712, but also to enter the eyes of a user at a specific beneficial angle(s) for photobiomodulation and other therapeutic treatments from the sun. The material 3712 is integrated into the device 3711 and the material 3712 may be configured to include optical properties such that when light and/or sunlight enters one side of the material 3712 such as the surface side of the baseball cap 3711A, the light that passes through the material 3712 would be aimed at the eyes of a person, at a specific angle into the eyes such as a 30-45 degree angle (as example) into the eyes. The material 3712 may further include wavelength filters that only allow certain wavelengths to pass through such as 630-650 nm, 730-750 nm, and/or 830-850 nm for example while filtering out other wavelengths such as UV and/or near-UV wavelengths. As solar radiation 3714 is emitted from the sun, filter 3712 can be activated to modify the spectral content of the solar radiation shown as 3714 before passing through the brim of the baseball cap 3711A and 3715. This filtering process can then act on the incident radiation to produce a health benefit such as regulating the amount of circadian active radiation, red light therapy, NIR, IR, or the amount of ultraviolet radiation to provide a health benefit to the user. An optional power supply and controller system 3716 can be located at a discrete location on the material 3711 such that it can supply power and control inputs to the filter element 3712. Other embodiments of this invention 3711 could be employed in car visors, windshields, windows, helmets, face masks, or eyewear or other locations to support a variable transmission of radiation to a user.

Figures 34A, 34B:
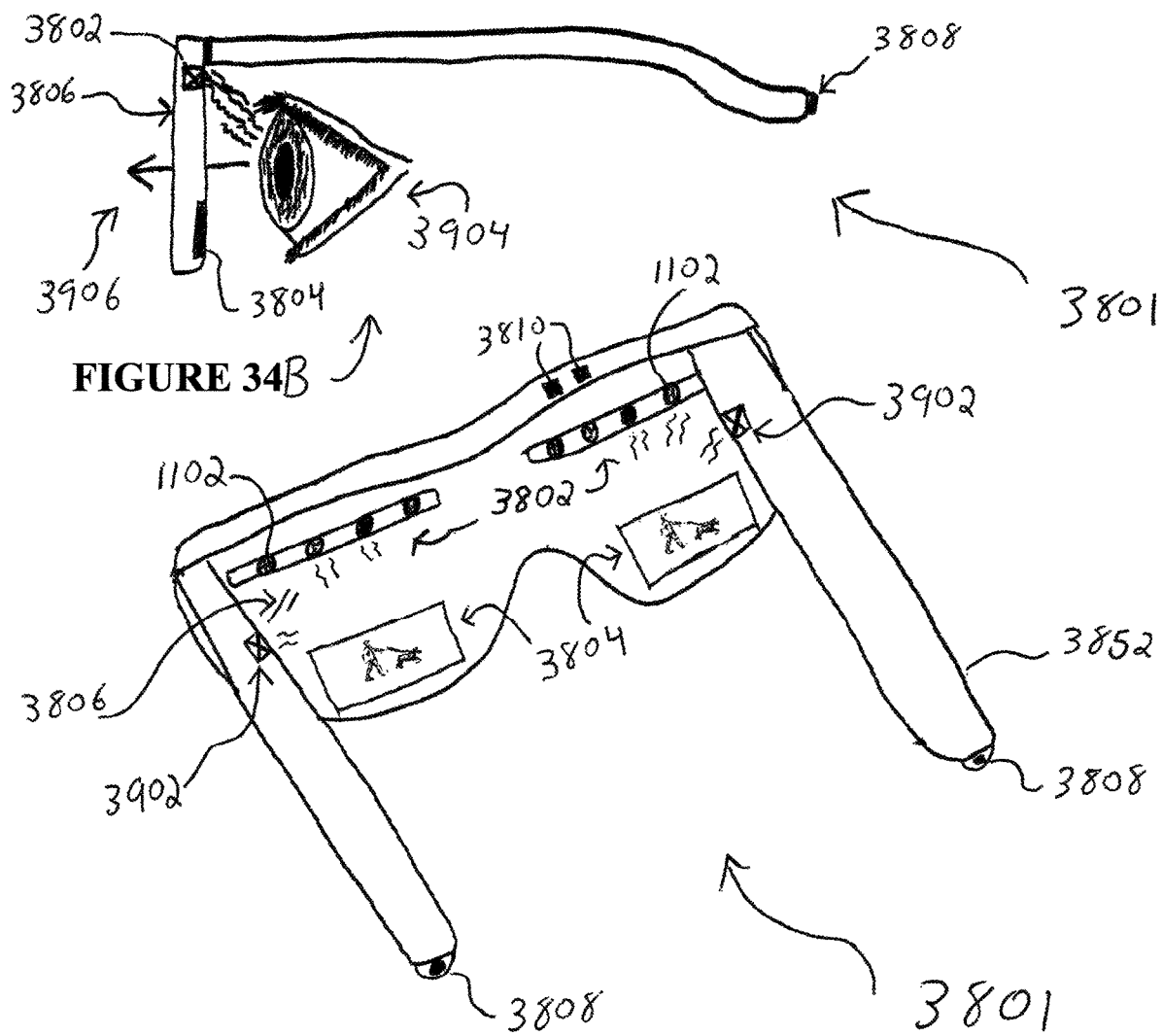
FIG. 34A shows a schematic view of an embodiment according to the invention.
FIG. 34B shows a schematic view of an embodiment according to the invention.

FIGS. 34A and 34B show another example embodiment of an eyewear device 3801 according to the invention which may be configured to be similar to and include one or more of the same features and/or capabilities as the device 3701 described in FIGS. 33A and 33B in addition to other possible features and embodiments. The eyewear device 3801 may further be configured to comprise one or more of the emission device 3802 configured to have one or more of the emitters, configurations and/or features of device 1100 as described above in FIG. 15, Eyewear device 3801 may further be configured to comprise at least one video display device 3804 configures to fill only a small portion, or a substantially large portion of the entire eyewear device lens 3806 which may be a photochromic lens, a prescription lens, a non-prescription magnification lens or a combination thereof. Eyewear device 3801 may further be configured to be or to me made of a solid, semi-solid or flexible material, and/or a combination thereof. Emission device 3802 may be configured to comprising at least one light emitter 1102 configured to emit one or more wavelengths of light energy in the wavelength spectrum of visible and/or non-visible light directed toward the human eye and/or a portion of the human body and more specifically at least one or more wavelengths of light in the orange-red light spectrum of 585 nm to 620 nm, red light spectrum of 620 nm to 750 nm, and/or at least one wavelength of light within the near-Infrared and/or infrared spectrum of 700 nm to 1 mm at a specific direction such as straight into the eye(s) of a person, or at a specific angle into the eye(s) of a person such as 30 degrees or other angles. The eyewear device 3801 and/or the emission device 3802 may comprise at least one type, or different types of light emitters 1102 similar to the device 1100 described in FIG. 15 to include at least one or a combination of at least one orange/red and/or red light emitter ("RL-e") 1104 configured to emit at least one wavelength(s) of light 1105 within the range of 585 nm to 750 nm and more specifically in the range of 610 nm to 660 nm, at least one near-infrared emitter ("NIR-e") 1106 configured to emit at least one wavelength(s) 1107 within the range of 780 nm to 1400 nm and more specifically in the range of 820 nm to 860 nm which may ideally be 830 nm and/or 850 nm, at least one MID-infrared emitter ("MIR-e") 1108 configured to emit at least one wavelength(s) 1109 within the range of 1,400 nm to 3000 nm and more specifically in the range of 1050 nm to 2500 nm (and in some cases 1060 nm specifically), and/or at least one far-infrared emitter ("FIR-e") 1110 configured to emit at least one wavelength(s) 1111 within the range of 3000 nm to 1 mm and more specifically within the range of 8 to 10 microns to better match the IR emissions and absorption of the human body and or cells. The light emitters 1102 and/or 1102, 1104, 1106, 1108, and/or 1110 may be integrated as one or more subassemblies or the device 1100 and/or emission device 3802 may be a subassembly that is integrated into the eyewear device. The eyewear device 3801 may comprise a substrate, a semiconductor backplane including but not limited to a CMOS backplane, a driver backplane, a package, an assembly or a housing, an integrated circuit ("IC"), a processor, a controller, a timer, a wired or wireless transceiver, a wired or wireless sensor(s) including but not limited to at least one biofeedback sensor, proximity sensor, motion sensor, light sensor, ambient light and/or ambient temperature sensor, and/or human body temperature sensor, software, firmware, a solid state memory, a battery, a wireless charger, and/or a camera. The eyewear device 3801 may also comprise at least one optic and/or lens which may optionally be a dynamically and/or electronic controlled optic and/or lens similar to optic 1116 as described in FIG. 15. At least one or more of the light emitters 1102 may be a laser. The device 1100 may also comprise a power supply and/or electronic driver circuit for selectively powering and/or controlling the power being delivered to one or more of the light emitters 1102 simultaneously or independently, and powering other integrated electronics needed for operating the eyewear device 3801. The power supply and/or electronic driver circuit may include at least one or more of a power connections or leads, electrical contacts, software drivers, transistors, current regulator, voltage regulator, timer, controller, power control circuit, resistors, capacitors, inductors, diodes, integrated circuits ("ICs"), antennas, fuses, sensors, feedback circuitry, firmware, software, or other devices required to provide, control and/or manage power to circuits and components in order control the emission of one or more wavelengths of light emitted from the light emitters 1102. The eyewear device 3801 may further comprise a power input cable having a connector and/or adaptor configured to connect the device to a power source such a USB type charging port. The eyewear device 3801 may be configured to include a battery which may be a rechargeable battery, or another device that can provide power such as a transportation vehicle or an electronic device comprising an electronic display device configured to provide power and/or data through a connection port including but not limited to USB ports, lightning ports, Type-C ports, Cat 5 ports or other ports known to those skilled in the art may connect wirelessly or by wire to the eyewear device to provide power for charging. As described in FIGS. 33A to 33D, the eyewear device 3701 or this eyewear device 3801 may be in wired and/or wireless communication with another electronic device via at least one transceiver integrated in and/or connected to the eyewear device 3801. The eyewear device 3801 may further comprise at least one rearview camera 3808 integrated into the arm 3852 of the eyewear device 3801. Eyewear device 3801 may further comprise at least one temple region emission device 3902 configured to emit one or more of the previously mentioned herein electromagnetic wavelengths of red, near-IR, and/or IR, including but not limited to one or more of 630 nm, 730 nm, 830 nm, and/or 1060 nm into the temple region of a person and/or user when wearing the eyewear device 3801 to provide additional PBM treatment to the retina of the eye, or for the treatment of age related wrinkles. Similar treatment emissions may be provided by emission device 3802. Eyewear device 3802 may further comprise one or more, and preferably two or more control buttons 3810 configure to control certain functionality of the eyewear device 3801 including but not limited to one or more of the power on/off modes, the emissions of the emission devices 3802 and/or 3902, video display device 3804, and/or the rearview camera 3808. It is contemplated by the inventors that when eyewear device 3801 is in wired or wireless connectivity and/or communication with another portable communication device such as an Apple® I-phone or Samsung Galaxy® smartphone that includes one or more integrated cameras and software that allows to the camera to reverse image onto the display from front view of the smartphone to the camera facing the user which is a common feature, the same control feature in the smartphone can be used to select the rearview camera 3808 in place of the smartphone camera that faces the user and that the images detected by the rearview camera 3808 of the eyewear device 3801 could be displayed on the video display device 3804 and/or the display of the smartphone, or even optional a smart wearable device such as a smartwatch may provide the same functionality in place of the smartphone the wearable device may further provide biofeedback data to the eyewear device 3801. It is contemplated by the inventors that one or more of the light emitters 1102 may be an LED and/or OLED configured to emit one or more wavelengths of light in the visible spectrum of light and be converted into at least any one of one wavelength of red light, IR light, and/or white light emission with quantum dots and/or nano-crystals that are either excited and/or energized with one or a combination of the adjustable visible light emission, adjustable electrical current, adjustable magnetic fields, adjustable electromagnetic fields, adjustable radio waves, adjustable static electricity, and/or adjustable audio waves. It is further contemplated that the eyewear device 3801 may comprise wireless control, audio input and output which may include at least one Bluetooth speaker and/or a bone conduction speaker. It is further contemplated that the eyewear device 3801 may include an artificial intelligence ("AI") system and/or processors or be in communication with AI systems and/or processors, controllers and/or software that responds to input data by a person and/or biofeedback data from a person or a device worn by a person including but not limited to the eyewear device 3801. It is further contemplated by the inventors that at least one or more of the light emitters integrated within the eyewear device would provide the same benefits as described in FIG. 15 for wearable displays including but not limited to a head wearable display for display applications near the eye including but not limited to virtual reality ("VR") displays, live video displays, and/or augmented reality ("AR") displays where blue wavelengths of light are emitted and would benefit from adding red light and/or IR light directed into the eye and/or near the temple of a person's head such that the red light and/or IR light reaches the mitochondria cells of the human body and/or eyes and optic nerves of a person including but not limited to the retina of the eye(s) thereby stimulating the cells and causing the cells to regenerate and/or produce more ATP. It is further contemplated that a substantial portion of the lens 3806 of the eyewear device 3801 may be filled with an array of the one or more light emitters and that such light emitters can be used as an individual pixel when an embodiment of the eyewear device calls for it.

FIG. 34B is a side view of eyewear device 3801 (and/or eyewear device 3701) showing the eye 3904 of a person looking into the eyewear device 3801. Emission device 3802 is position within eyewear device 3801 at a location above the direct line of sight 3906 at, or through the lens 3806. The video display device 3804 is positioned below the direct line of sight 3906 of the person's eye 3904 looking at, or through the lens 3806. The lens 3806 may be configured to be clear, tinted or a tunable photochromic lens as described above and allow for a person wearing to eyewear device 3801 to receive emissions into the eye 3904 from the emission device 3802 at a specific angle into the eye(s) such as 30 or 40 degrees while being able to look slightly downward into the display device 3804 and/or through the lens 3806 while receiving red light therapy and/or PBM treatments form the eyewear device 3801.

Figure 34C:
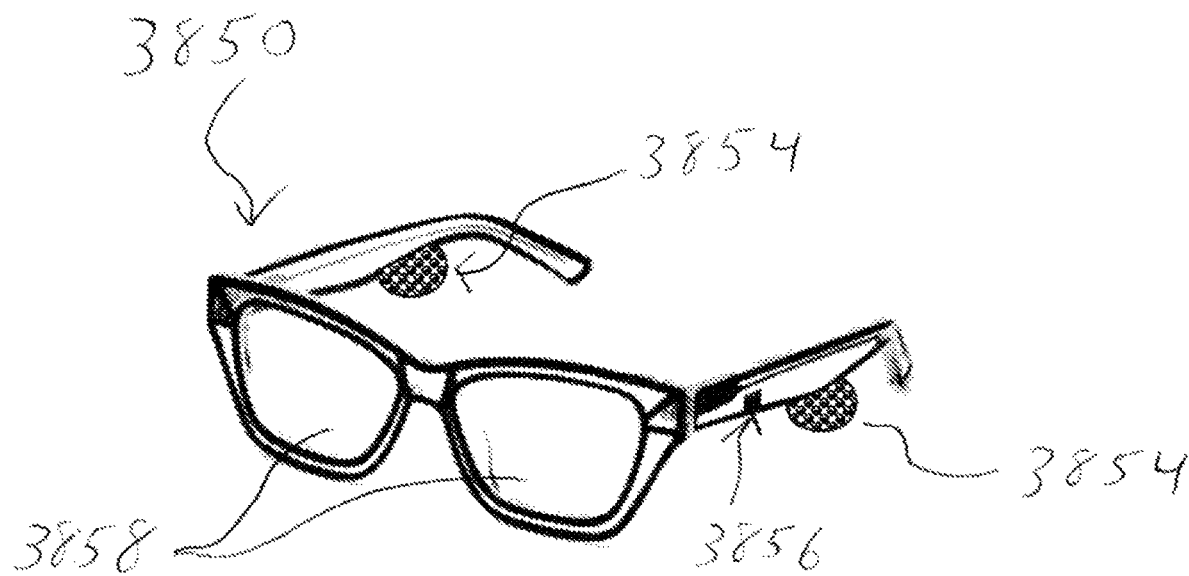
FIGS. 34C and 34D show schematic views of embodiments according to the invention.
Figure 34D:
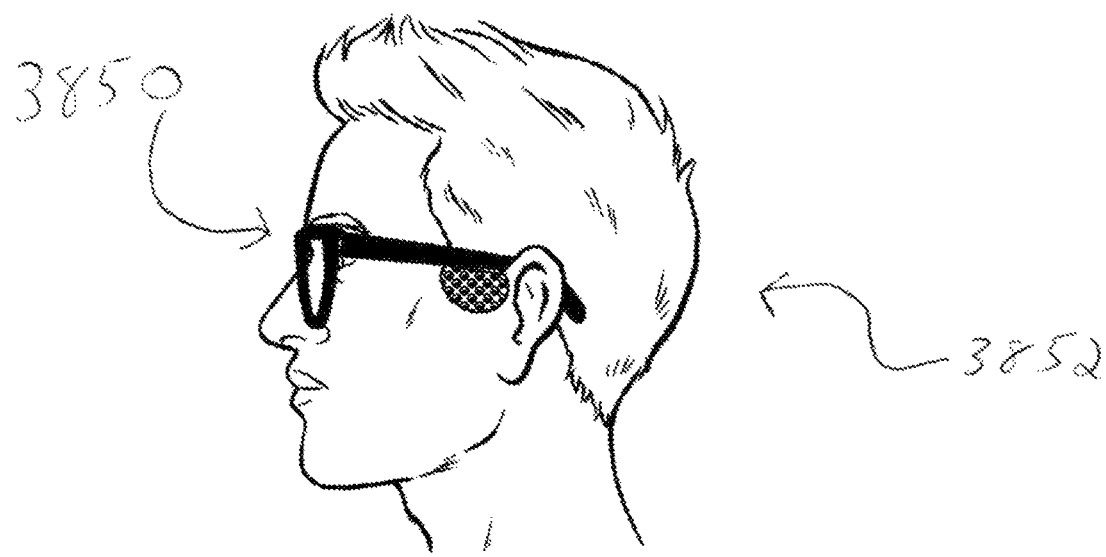

FIGS. 34C and 34D show and describe another example embodiment of an eyewear device 3850 according to the invention. FIG. 34C shows and describes the eyewear device 3850 and FIG. 34D shows the eyewear device 3850 according to the invention being worn by a person 3852. It is contemplated by the inventors that a simpler form of an eyewear device 3801 may be configured to include the combination of at least one bone conduction speaker(s) 3854 and at least one microphone 3856 and/or audio receiver along with lenses 3858 which may be prescription lenses and/or magnification lenses, sunglass lenses and/or smart lenses. The eyewear device 3850 is configured to be a replacement for hearing aids for people that wear eyewear. The microphone may be configured to detect sound like a hearing aid that is then output from the bone conduction speakers. Such an embodiment according to the invention would essentially be a pair of glasses for vision that has at least one integrated hearing aid using bone conduction technology. Such an eyewear device 3850 may further be configured to provide light emission of red and/or IR as described herein and according to the inventions described herein. Eyewear device 3850 may further be configured to include one or more of the other features of eyewear device 3801 including but not limited to a battery, a camera, a USB port, wireless charging features, and/or other features and functionality according to the inventive embodiments described herein.

Figure 35:
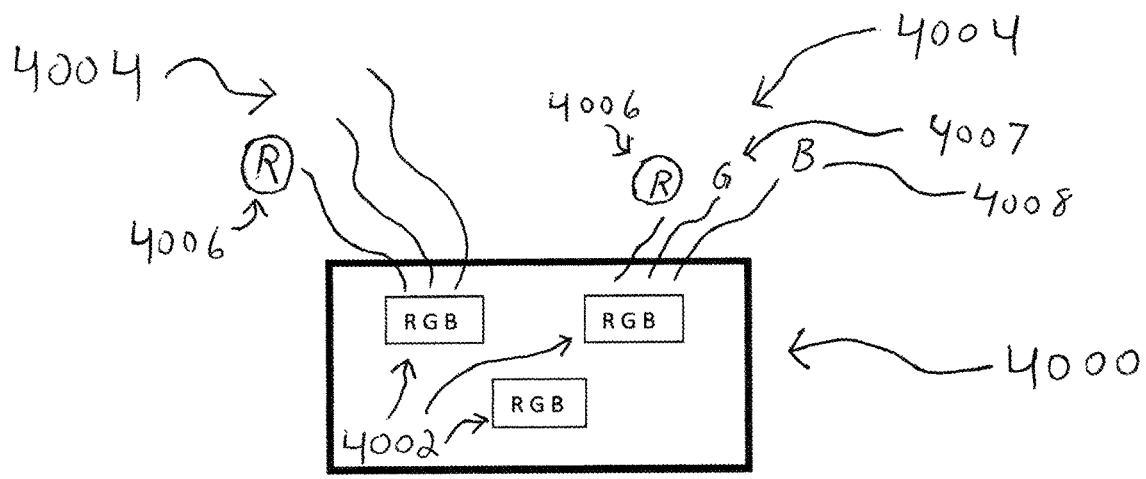
FIG. 35 shows a schematic view of an embodiment according to the invention.
Figure 36:
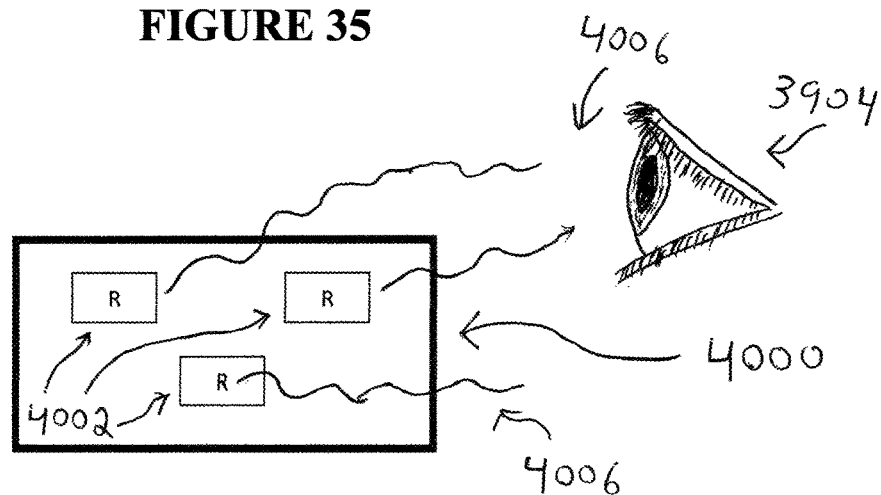
FIG. 36 shows a schematic view of an embodiment according to the invention.

FIGS. 35 and 36 show another example embodiment of a device 4000 according to the invention which may be another example embodiment of any one or more of the example embodiments of devices, including display devices and/or devices with displays according to the inventions disclosed herein. The device 4000 may be the display portion of any video display device and/or device comprising a video display according to the inventions described herein including but not limited to a portable telecommunications device such as a mobile phone, a laptop or desktop computer, an automotive or other transportation vehicle display, a wearable device with a display, an eyewear device including but not limited to the eyewear devices described in FIGS. 33A through 34B, and/or a television display that may be already configured to include multiple RGB light emitters 4002 which may be any size and/or form of LED and/or OLED used as pixels and/or RGB light emitters 4002 to produce RGB wavelength emissions 4004 of the video display images produced from the video display and/or device 4000. The red light emissions 4006 of the RGB light emitters 4002 may be configured to emit red light in the range of 620 nm to 660 nm and more specifically in the range of 630 nm to 650 nm directed towards the eyes 3904 and/or retina of a viewer of the display for providing PBM treatments to improve vision and deliver other health benefits to the body derived from receiving such PBM treatments.

According to this embodiment of the invention as shown and described in FIG. 36, the device 4000 may be configured and controlled to turn off the green light emissions 4007 and blue light emissions 4008 and only emit the red light emissions 4006 such as 630 nm or 650 nm (for example) electromagnetic energy from the RGB light emitters 4002 in the device 4000, or alternately only emit the red light emissions 4006 from a substantial portion of the RGB light emitters 4002 in the device 4000, or alternately only emit the red light emissions 4006 from a specific region of the device 4000.

The device 4000 may be configured to provide such red light emissions 4006 for a specific period of time such as two or three minutes a day for example, each day or every other day for example, at a specific level of energy. It is contemplated by the inventors that a software and/or app update could be provided to update an existing video display device such as a smartphone, PC, TV, or other display device that already includes RGB emitters that are capable of being used for such new health and wellness treatments to the eyes and other parts of the body in addition to providing such emissions for PBM treatments for improved vision along with video display images. As one example, an Apple® I-Phone may be configured to include the functionality of the device 4000 with a simple software update if the RGB light emitters in the video display device (such as the I-Phone) already comprise pixels and or RGB light emitters and/or other light emitters configured to emit such red, near-IR, and IR wavelengths desirable for certain PBM treatments including but not limited to 600 nm to 1060 nm that could be used for treatment of the mitochondria cells in the retina for improved vision and/or other PBM health benefits. It is further contemplated by the inventors that the display device 4000 may further be configured to additionally emit wavelengths of only light in the blue region between 400 nm and 500 nm (and in some cases in combination with red and/or IR emissions) to provide antibacterial light emissions and/or circadian entrainment health benefits and/or effects.

It is contemplated by the inventors that any one or more of the embodiments according to the invention described herein, the visible and non-visible electromagnetic energy wavelengths and/or emissions may be configured to cycle on and off, at various levels of emissions and/or treatments and increase power for a period of time which may be minutes and/or hours in a day to provide various emissions from the device including but not limited to one or more of the wavelengths described in any of the figures according to the inventions described herein with such wavelengths being responsive to the sensors including but not limited to biofeedback sensors, and/or control methods described here. For example a device such as a ceiling light and/or other lighting device having a primary function of delivering general lighting light emissions of white light and/or UV and/or near UV anti-bacterial light emissions of in a room, and draws only 20-40 watts of power to provide such light and/or UV emissions, may further be configured to include the red and/or IR light emission features described here and such red and/or IR emissions could be configured to operate at a specific time for a specific period of time which may cause such a lighting device to increase the amount of power draw from 20-40 watts to more power such as 50-1000+ watts for a controlled period of time in order to at least deliver red and/or IR light emissions for PBM treatments, and possibly and optionally personal space heating to a person and/or living species near the lighting device. As result and by way of example according to the invention, such a device and/or light fixture may be configured to draw 200 watts for only several minutes or hours within a 24 (twenty four) hour period of time (in many cases less than the common toaster oven, space heater, microwave and/or hair dryer) thereby providing the benefits of PBM and personal space heat for only a small increase to the overall expense of power/energy costs.

Figure 37:
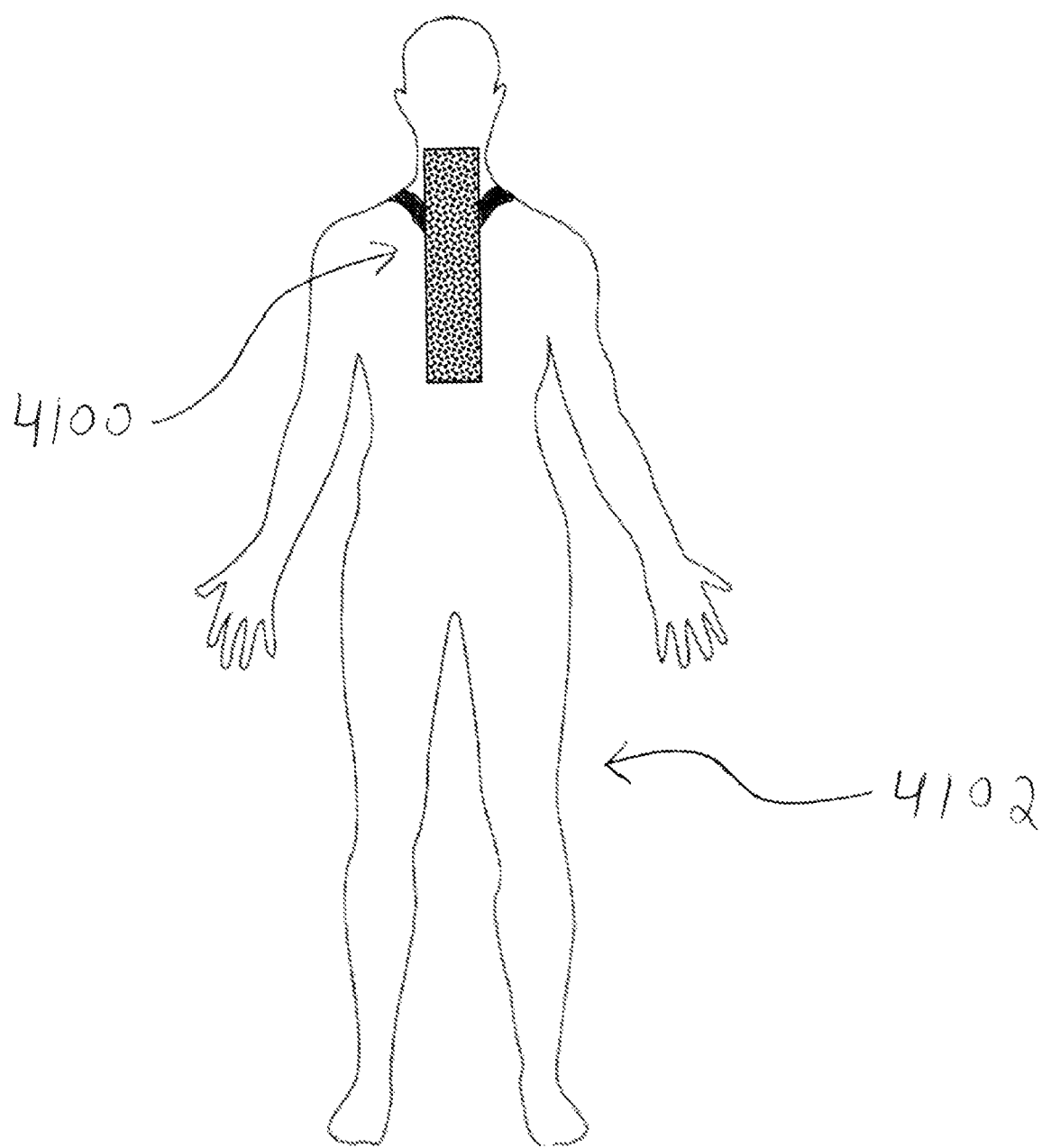
FIG. 37 shows a schematic view of an embodiment according to the invention.

FIG. 37 shows another example embodiment of an AILMD lighting device and/or system 4100 being worn on the upper front body portion of a person and/or living species 4102. The AILMD lighting device 4100 may be configured to include one of more of the features and functionality as the AILMD lighting device described herein in FIG. 5 and/or FIG. 9. The AILMD device 4100 may be configured to be placed onto the upper portion of a person and/or living species neck and/or chest area or hung on the neck to be positioned over the neck and/or chest area. The AILMD device 4100 may be solid, semi-solid, flexible or a combination thereof. The AILMD device 4100 is configured to provide and/or emit at least one or more of UV, near-UV, red, near-IR, mid-IR, and/or far-IR wavelengths of energy into the esophagus of a person and/or living species, or onto the front of the neck, chest, and/or neck and chest of a person and/or living species such that the wavelengths of energy emitted are emitted into the esophagus and/or are emitted to pass onto and through the neck and/or chest area of tissue, tendons, and/or muscle of the person and/or living species to reach the esophagus and provide therapeutic benefits of PBM as well as other benefits including but not limited to anti-inflammatory, vasodilation, localized and/or focused heating which according to the invention may provide benefits for anti-cancer, anti-asthma, chronic obstructive pulmonary disease ("COBD"), chronic cough, and other breathing and/or esophageal type ailments that could be treated with such a wearable anti-infective radiation device according to the invention. Such a device would be configured to include one or more of the other following features including but not limited to: provide different levels of brightness and/or intensities of output wavelengths of visible and/or non-visible light by switching or controlling the wavelengths in response to one or more control devices and/or methods including but not limited to sensors, controllers, microprocessors, biofeedback, integrated circuits and/or other wavelength management and/or control circuitry or user or operator of the device. The sensors can include but not be limited, to sensors capable of sensing one or more of temperature including but not limited to ambient or body temperature, sound, vibration, electrical signals, including but not limited to, a person's electrical signals, the infrared emissions of a person, humidity, blood, blood pressure, blood oxygen levels, microorganisms, organisms, biofeedback, bio-resonance, proximity and/or location of a person and/or device including but not limited to an electronic device, oxygen, enzymes, fluids, and/or minerals.

It is further contemplated by the inventors that one or more of the devices according to the inventions described herein may be configured to comprise a vitamin D3 level bio-sensor configured to measure the active form of vitamin D concentration of 25(OH)D (25-hydroxyvitamin D) in the blood and provide dosimetry data derived from such levels of D3 for control and timing or dosimetry of red, NIR, MIR, and/or FIR PBM treatments and durations of treatment to a living species. It is contemplated by the inventors that such a vitamin D3 level bio-sensor may be configured to measure the production of vitamin D3 from the skin in response to reflection of electromagnetic wavelengths such as red and/or IR into the skin and/or blood to deliver such data back to one or more of the devices according to the inventions described herein.

It is further contemplated by the inventors that a video display device according to the invention and described herein may be configured to comprise a software application configured to control the percentage of red light emitters emitting red light from the video display device, the location of the red light emitters emitting red light from the video display device, the time of day the red light emitters emit red light from the video display device, the duration of time the red light emitters emit red light from the video display device, and the rGB light emitters configured to produce video images from the video display device.

While the foregoing there has set forth embodiments of the invention, it is to be understood that the present invention may be embodied in other forms without departing from the spirit or central characteristics thereof. The present embodiments, therefore, are to be considered in all respects as illustrative and not restrictive, and the invention is not to be limited to the details given herein. While specific embodiments have been illustrated and described, numerous modifications come to mind without significantly departing from the characteristics of the invention and the scope of protection is only limited by the scope of the accompanying claims.

What is claimed is:

1. An electronic device for providing photobiomodulation ("PBM") light therapy towards a face of a person facing the electronic device, the electronic device comprising:
    a housing;
    at least one video display device;
    at least one sensor configured to sense a distance between the electronic device and the face of the person facing the electronic device;
    a first plurality of light emitters configured to receive first control signals that cause the first plurality of light emitters to emit modulated RGB wavelengths of light for producing video images on the at least one video display device; and
    a second plurality of light emitters configured to receive second control signals in response to the at least one sensor sensing the distance between the electronic device and the face of the person, wherein the second control signals cause the second plurality of light emitters to emit PBM wavelengths of light at a first output energy level for a duration of time for providing PBM light therapy towards the face of the person facing the electronic device, wherein the PBM wavelengths of light emitted comprise one or more PBM wavelengths of light within a range of 600 nm to 1400 nm known to stimulate mitochondria cells in a person and cause the mitochondria cells to produce additional adenosine triphosphate ("ATP"),
    wherein the second plurality of light emitters is configured to be controlled to emit the PBM wavelengths of light independent of the first plurality of light emitters being modulated and producing any video images,
    wherein the second plurality of light emitters is further controlled to adjust the first output energy level or the duration of time the PBM wavelengths of light are emitted in response to changes in the distance sensed between the face of the person and the electronic device by the at least one sensor, and
    wherein the second plurality of light emitters is configured to be controlled in response to an output from the at least one sensor and emit light at the first output energy level for the duration of time or a second output energy level or a second duration of time before twelve noon according to a geographical location of the electronic device.

2. The electronic device of claim 1, wherein the second plurality of light emitters is configured to emit the PBM wavelengths of light within the range of 600 nm to 1400 nm towards the face of the person facing the electronic device, wherein the second plurality of light emitters is configured to emit the PBM wavelengths of light for a controlled period of time at a specific time of day, and wherein the controlled period of time totals at least two minutes before noon within a single day.

3. The electronic device of claim 1, wherein the second plurality of light emitters is configured to emit the PBM wavelengths of light within the range of 600 nm to 1400 nm towards the face of the person facing the electronic device, wherein the second plurality of light emitters is configured to emit the PBM wavelengths of light for a controlled period of time at a specific time of day, and wherein the controlled period of time totals at least one consecutive minute before noon within a single day.

4. The electronic device of claim 1, wherein the second plurality of light emitters is integrated into the at least one video display device.

5. The electronic device of claim 1, wherein the second plurality of light emitters is integrated into the housing of the electronic device.

6. The electronic device of claim 1, wherein the second plurality of light emitters is configured to emit two or more controlled wavelengths of light within the range of 600 nm to 1400 nm when the at least one video display device is displaying the video images.

7. The electronic device of claim 1, wherein the second plurality of light emitters is configured to respond to the second control signals that are received in response to at least one camera integrated within the electronic device and cause the PBM wavelengths of light to be emitted through at least one optic that is configured to focus the PBM wavelengths of light onto the face of the person facing the electronic device.

8. The electronic device of claim 1, wherein the second plurality of light emitters is configured to emit the PBM wavelengths of light in response to the electronic device receiving biological information related to the person facing the electronic device, wherein the biological information is received from a remote electronic device.

9. The electronic device of claim 1, wherein at least one of the light emitters of the second plurality of light emitters is configured to be a laser.

10. The electronic device of claim 1, wherein the second plurality of light emitters is configured to respond to a camera integrated within the electronic device, and wherein the camera is configured to impact how the electronic device controls the second plurality of light emitters.

11. The electronic device of claim 1, wherein at least one of the light emitters of the second plurality of light emitters is configured to emit light through an electronically controlled optic that is configured to respond to a camera, and wherein the camera is configured to impact how the electronic device controls the at least one of the light emitters.

12. The electronic device of claim 1, wherein the second plurality of light emitters is configured to emit the PBM wavelengths of light in response to the second control signals received in response to a camera detecting movement of the person facing the electronic device.

13. The electronic device of claim 1, further comprising a camera and at least two phosphor coated LEDs configured to emit two or more color temperatures of white light,
wherein the second plurality of light emitters, the camera, and the at least two phosphor coated LEDs are configured to be independently controlled by the electronic device via a wired or a wireless connection.

14. The electronic device of claim 1, wherein the electronic device is a wearable display.

15. An electronic device for providing photobiomodulation ("PBM") light therapy towards a face of a person facing the electronic device, the electronic device comprising:
at least one video display device;
at least one sensor configured to sense a distance between the electronic device and the face of the person facing the electronic device;
a first plurality of light emitters configured to receive first control signals that cause the first plurality of light emitters to be modulated and emit RGB wavelengths of light for producing video images on the at least one video display device; and
a second plurality of light emitters configured to receive second control signals in response to the at least one sensor sensing the distance between the electronic device and the face of the person, wherein the second control signals cause the second plurality of light emitters to emit PBM wavelengths of light at a first output energy level for a duration of time for providing PBM light therapy towards the face of the person facing the electronic device, wherein the PBM wavelengths of light comprise one or more wavelengths of light within a range of 600 nm to 1400 nm known to stimulate mitochondria cells in a person and cause the mitochondria cells to produce additional adenosine triphosphate ("ATP"),
wherein the second plurality of light emitters is configured to emit the PBM wavelengths of light independent of the first plurality of light emitters emitting any modulated RGB wavelengths of light used to produce the video images on the at least one video display device, and wherein the second plurality of light emitters is configured to emit the PBM wavelengths of light towards the face of the person facing the electronic device for a total of at least one minute before twelve noon within a single day,
wherein twelve noon is determined according to a geographical location of the electronic device, and
wherein the second plurality of light emitters is further configured to be controlled in response to an output from the at least one sensor and to adjust the first output energy level or the duration of time the PBM wavelengths of light are emitted in response to changes in the distance sensed between the face of the person and the electronic device by the at least one sensor.

16. The electronic device of claim 15, wherein the second plurality of light emitters is configured to emit the PBM wavelengths of light within the range of 600 nm to 1400 nm towards the face of the person for a controlled duration of time at a specific time of day, and wherein the controlled duration of time totals at least one minute before noon within a single day.

17. The electronic device of claim 15, wherein the second plurality of light emitters is configured to emit the PBM wavelengths of light within the range of 600 nm to 1400 nm towards the face of the person for a controlled duration of time at a specific time of day in response to the electronic device receiving data wirelessly from a wearable device worn by the person facing the electronic device, and wherein the controlled duration of time totals at least one consecutive minute before noon within a single day.

18. The electronic device of claim 15, wherein the second plurality of light emitters is configured to emit the PBM wavelengths of light within the range of 600 nm to 1400 nm towards the face of the person through at least one optic that is configured to focus the PBM wavelengths of light onto the face of the person facing the electronic device while the person is viewing the video images on the at least one video display device.

19. The electronic device of claim 15, wherein at least 5% of the first plurality of light emitters are configured to only emit red light within a range of 585 nm to 750 nm towards the face of the person for a controlled constant duration of time at a specific time of day before noon.

20. The electronic device of claim 15, wherein the second plurality of light emitters includes micro-LEDs.

21. The electronic device of claim 15, wherein at least one light emitter of the second plurality of light emitters is a laser.

22. The electronic device of claim 15, wherein the second plurality of light emitters is configured to emit the PBM wavelengths of light in response to the electronic device receiving biological information from a second device, wherein the biological information includes information related to the person facing the electronic device and impacts the second control signals received by the second plurality of light emitters emitting the PBM wavelengths of light.

23. The electronic device of claim 15, wherein the electronic device is a wearable electronic device.

24. An electronic device for providing photobiomodulation ("PBM") light therapy towards a face of a person facing the electronic device, the electronic device comprising:
a housing;
at least one video display device integrated within the housing;
at least one sensor configured to sense a distance between the electronic device and the face of the person facing the electronic device;
a first plurality of light emitters integrated within the at least one video display device and configured to be controlled to produce video images by emitting modulated RGB wavelengths of light from the at least one video display device; and
a second plurality of light emitters integrated within the electronic device and configured to emit PBM wavelengths of light towards the face of the person facing the electronic device,
wherein the PBM wavelengths of light are emitted in response to the at least one sensor sensing the distance between the electronic device and the face of the person,
wherein the PBM wavelengths of light are within a range of 600 nm to 1400 nm and emitted through at least one optic that is configured to focus the PBM wavelengths of light towards the face of the person facing the electronic device,
wherein the PBM wavelengths of light are controlled and emitted independent of the modulated RGB wavelengths of light being controlled and emitting any light for the video images,
wherein the second plurality of light emitters is controlled to emit the PBM wavelengths of light at a first energy level for a duration of time that totals at least one minute before twelve noon within a single day,
wherein twelve noon is determined according to a geographical location of the electronic device, and
wherein the second plurality of light emitters is further controlled to adjust the first energy level or the duration of time the PBM wavelengths of light are emitted in response to changes in the distance sensed between the face of the person and the electronic device.

25. The electronic device of claim 24, wherein the second plurality of light emitters is configured to emit the PBM wavelengths of light in response to data provided to the electronic device by a device that provides biofeedback information from the person facing the electronic device, and wherein a camera is configured to impact the control of the emission of the PBM wavelengths of light in response to motion of the person facing the electronic device.

26. The electronic device of claim 24, wherein the at least one optic is configured to have the second plurality of light emitters emit the PBM wavelengths of light, the at least one optic being dynamically controlled and configured to respond to the at least one sensor, and wherein the at least one sensor is configured to impact how the electronic device controls the at least one optic and the emission of the PBM wavelengths of light from the second plurality of light emitters.

27. The electronic device of claim 24, wherein the second plurality of light emitters is configured to emit one or more controlled wavelengths of light within a range of 595 nm to 750 nm when the at least one video display device is displaying the video images.

28. An electronic device with a video display for providing photobiomodulation ("PBM") light therapy, the electronic device comprising:
at least one sensor configured to sense a distance between the electronic device and a face of a person facing the electronic device; and
a plurality of RGB light emitters configured to produce video images by emitting modulated RGB wavelengths of light towards the face of the person facing the electronic device,
wherein a percentage of the plurality of RGB light emitters are configured to only emit PBM wavelengths of light within a range of 585 nm to 750 nm towards the face of the person facing the electronic device, wherein the PBM wavelengths of light are emitted at a first energy level for a duration of time before twelve noon within a single day, and wherein twelve noon is determined according to a geographical location of the electronic device,
wherein the PBM wavelengths of light being emitted at the first energy level and the duration of time are configured to be controlled to adjust at least one of (i) the first energy level of the PBM wavelengths of light, (ii) the percentage of the RGB light emitters configured to only emit the PBM wavelengths of light within the range of 585 nm to 750 nm, or (iii) the duration of time the PBM wavelengths of light are emitted, in response to changes in the distance sensed between the face of the person and the electronic device.

29. The electronic device of claim 28, further comprising a software application configured to control:
the percentage of red light emitters emitting the PBM wavelengths of light,
which of the red light emitters are to emit the PBM wavelengths of light,
the time of day the red light emitters emit the PBM wavelengths of light,
energy levels of the red light emitters that emit the PBM wavelengths of light, and
the duration of time the red light emitters emit the PBM wavelengths of light.

30. The electronic device of claim 28, wherein the electronic device is configured to be wearable and configured to be in wireless communication with another device.

* * * * *